United States Patent
Eberwine et al.

(10) Patent No.: US 11,873,312 B2
(45) Date of Patent: Jan. 16, 2024

(54) TRANSCRIPTOME IN VIVO ANALYSIS (TIVA) AND TRANSCRIPTOME IN SITU ANALYSIS (TISA)

(71) Applicant: The Trustees of the University of Pennsylvania, Philadelphia, PA (US)

(72) Inventors: James Eberwine, Philadelphia, PA (US); Ivan J. Dmochowski, Philadelphia, PA (US); Sean B. Yeldell, Philadelphia, PA (US); Julianne C. Griepenburg, Philadelphia, PA (US); Teresa L. Rapp, Philadelphia, PA (US); Jennifer M. Singh, Havertown, PA (US); Jai-Yoon Sul, Cherry Hill, NJ (US); Jaehee Lee, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 249 days.

(21) Appl. No.: 17/333,376

(22) Filed: May 28, 2021

(65) Prior Publication Data
US 2021/0292352 A1     Sep. 23, 2021

Related U.S. Application Data

(62) Division of application No. 15/501,073, filed as application No. PCT/US2015/043581 on Aug. 4, 2015, now Pat. No. 11,021,502.
(Continued)

(51) Int. Cl.
*C12Q 1/6823*     (2018.01)
*C12Q 1/6825*     (2018.01)
(Continued)

(52) U.S. Cl.
CPC ......... *C07F 15/0053* (2013.01); *B01J 35/004* (2013.01); *C07H 23/00* (2013.01);
(Continued)

(58) Field of Classification Search
CPC ................. B01J 35/004; C12N 15/113; C12N 2310/531; C12Q 1/6818; C12Q 1/6823
See application file for complete search history.

(56) References Cited

U.S. PATENT DOCUMENTS 5,034,506 A   7/1991  Summerton
5,296,566 A   3/1994  Brown-Wensley
(Continued)

FOREIGN PATENT DOCUMENTS

WO   WO-2007107162 A2 *   9/2007  ........... C12N 15/111
WO   WO-2008049078 A1 *   4/2008  ........... A61K 31/713
(Continued)

OTHER PUBLICATIONS

Ruble. "Design and Application of Photoactivatable Oligonucleotides" 2012. Dissertation. University of Pennsylvania. (Year: 2012).*
(Continued)

*Primary Examiner* — Joseph G. Dauner
(74) *Attorney, Agent, or Firm* — Riverside Law LLP

(57) ABSTRACT

Compositions and methods of capturing one or more nucleic acid molecules of a cell or subcellular compartment are described. In certain aspects, the compositions comprise a caged molecule comprising one or more photolinkers and an antisense oligonucleotide, which when uncaged hybridizes to a target nucleic acid molecule.

9 Claims, 42 Drawing Sheets
(34 of 42 Drawing Sheet(s) Filed in Color)
Specification includes a Sequence Listing.

Related U.S. Application Data

(60) Provisional application No. 62/033,007, filed on Aug. 4, 2014, provisional application No. 62/035,410, filed on Aug. 9, 2014.

(51) Int. Cl.

| | | |
|---|---|---|
| C12Q 1/6818 | (2018.01) | |
| C07F 15/00 | (2006.01) | |
| C12N 15/113 | (2010.01) | |
| C07H 23/00 | (2006.01) | |
| C12N 13/00 | (2006.01) | |
| B01J 35/00 | (2006.01) | |

(52) U.S. Cl.
CPC ............ *C12N 13/00* (2013.01); *C12N 15/113* (2013.01); *C12Q 1/6818* (2013.01); *C12Q 1/6823* (2013.01); *C12Q 1/6825* (2013.01); *B01J 2531/821* (2013.01); *C12N 2310/11* (2013.01); *C12N 2310/32* (2013.01); *C12N 2310/3233* (2013.01); *C12N 2310/351* (2013.01); *C12N 2310/3517* (2013.01); *C12N 2310/531* (2013.01)

(56) References Cited

U.S. PATENT DOCUMENTS

| | | | |
|---|---|---|---|
| 5,874,046 | A | 2/1999 | Megerle |
| 9,540,634 | B2 | 1/2017 | Eberwine |
| 9,540,680 | B2 | 1/2017 | Eberwine |
| 2002/0102586 | A1 | 8/2002 | Ju |
| 2003/0201161 | A1 | 10/2003 | Nocera |
| 2012/0028814 | A1 | 2/2012 | Toloue |
| 2013/0066059 | A1 | 3/2013 | Chen |
| 2013/0267678 | A1* | 10/2013 | Eberwine ........... C12N 15/1003 536/25.4 |
| 2013/0273537 | A1 | 10/2013 | Eberwine |
| 2014/0073611 | A1 | 3/2014 | Wang |

FOREIGN PATENT DOCUMENTS

| | | | | |
|---|---|---|---|---|
| WO | WO-2009006438 | A2 * | 1/2009 | ......... C12N 15/1096 |
| WO | WO-2011046983 | A2 * | 4/2011 | ............ A61K 31/712 |
| WO | WO-2011156376 | A1 * | 12/2011 | ......... C12N 15/1003 |
| WO | 2012103309 | A2 | 8/2012 | |
| WO | WO-2013040060 | A2 * | 3/2013 | ............. C12Q 1/707 |

OTHER PUBLICATIONS

Glen Research. Retrieved on Mar. 15, 2023 from the internet: https://www.glenresearch.com/2-f-rna-phosphoramidites/10-3430.html. (Year: 2023).*

Ouyang et al., "Versatile Synthesis and Rational Design of Caged Morpholinos" 2009, J. Am. Chem. Soc. 131:13255-13269.

Ramírez et al., "Role of Ruthenium Oxidation States in Ligand-to-Ligand Charge Transfer Processes" 2012, Inorg. Chem. 51: 1261-1268.

Rial Verde et al., "Photorelease of GABA with visible light using an inorganic caging group" 2008, Front. Neur. Circ. 2 1-8.

Richards et al., "RNA Bandages for Photoregulating In Vitro Protein Synthesis" 2008, J Bioorg Med Chem Lett, 18: 6255-6258.

Richards et al., "Turning the 10-23 DNAzyme On and Off with Light" 2010 ChemBioChem, 11: 320-324.

Rostovtsev et al., "A Stepwise Huisgen Cycloaddition Process: Copper(I)-Catalyzed Regioselective 'Ligation' of Azides and Terminal Alkynes" 2002, Angew. Chem., Int. Ed. Engl. 41:2596-2599.

Ruble et al., "Mismatch discrimination and efficient photomodulation with split 10-23 DNAzymes" 2012, Inorg Chim Acta, 380: 386-391.

Salassa et al., "Ligand-Selective Photodissociation from [Ru(bpy)(4AP)4]2+: a Spectroscopic and Computational Study", 2009, Inorg. Chem.48: 1469-1481.

Salassa et al., "Mechanism of Ligand Photodissociation in Photoactivable [Ru(bpy)2L2]2+ Complexes: A Density Functional Theory Study" 2008, J. Am. Chem. Soc. 130: 9590-9597.

Salierno et al., "Caged Amino Acids for Visible-Light Photodelivery" 2008, Eur. J. Inorg. Chem. 2008:1125-1128.

Sears et al., "Photoinduced ligand exchange and DNA binding of cis-[Ru(phpy)(phen)(CH3CN)2] + with long wavelength visible light" 2013, J. Inorg. Biochem. 121:77-87.

Seward et al., "Cell-compatible, integrin-targeted cryptophane-129XeNMR biosensors" 2011, Chem. Sci., 2: 1103-1110.

Seward et al., "Peptide-Mediated Cellular Uptake of Cryptophane" 2008, Bioconjug. Chem., 19: 2129-2135.

Shestopalov and Chen, "Spatiotemporal Control of Embryonic Gene Expression Using Caged Morpholinos" 2011, Methods Cell Biol. 104:151-172.

Shestopalov et al., "Light-controlled gene silencing in zebrafish embryos" 2007, Nat. Chem. Biol. 3:650-651.

Singh et al., "Photoinitiated DNA Binding by cis-[Ru(bpy)2(NH3)2]2+" 2004, Inorg. Chem. 43: 7260-7262.

Stoien and Wang, "Effect of Near-Ultraviolet and Visible Light on Mammalian Cells in Culture II. Formation of Toxic Photoproducts in Tissue Culture Medium by Blacklight" 1974, Proc. Natl. Acad. Sci. U.S.A. 71:3961-3965.

Sudimack et al., "Targeted drug delivery via the folate receptor" Adv. Drug Deliv. Rev. 2000, 41, 147-162.

Tallafuss et al., "Turning gene function ON and OFF using sense and antisense photo-morpholinos in zebrafish" 2012, Development (Cambridge, England) 139:1691-1699.

Tang and Dmochowski, "Controlling RNA Digestion by RNase H with aLight-Activated DNA Hairpin" 2006, Angew. Chem., Int. Ed. 45:3523-3526.

Tang and Dmochowski, "Regulating gene expression with lightactivated oligonucleotides" 2007, Mol. BioSyst. 3:100-110.

Tang et al., "Photoregulation of DNA polymerase I (Klenow) with caged fluorescent oligodeoxynucleotides" 2005, Bioorg Med Chem Lett, 15: 5303-5306.

Tang et al., "Phototriggering of Caged Fluorescent Oligodeoxynucleotides" 2005, Org Lett, 7: 279-282.

Tang et al., "Regulating gene expression in human leukemia cells using light-activated oligodeoxynucleotides" 2008, Nucl Acids Res, 36: 559-569.

Tang et al., "Regulating Gene Expression in Zebrafish Embryos Using Light-Activated, Negatively Charged Peptide Nucleic Acids" 2007, J. Am. Chem. Soc. 129:11000-11001.

Thierry et al., "Overcoming Multidrug Resistance in Human Tumor Cells Using Free and Liposomally Encapsulated Antisense Oligodeoxynucleotides" Biochem Biophys Res Commun 1993, 190, 952-960.

Tomasini et al., "PhotoMorphsTM: A Novel Light-Activated Reagent forControlling Gene Expression in Zebrafish" 2009, Genesis 47:736-743.

Tornoe et al., "Peptidotriazoles on Solid Phase: [1,2,3]-Triazoles by Regiospecific Copper(I)-Catalyzed 1,3-Dipolar Cycloadditions of Terminal Alkynes to Azides" 2002, J. Org. Chem. 67:3057-3064.

Wahlestedt et al., "Potent and nontoxic antisense oligonucleotides containing locked nucleic acids" Proc. Natl. Acad. Sci. USA 2000, 97, 5633-5638.

Walker et al., "Photolabile 1-(2-Nitrophenyl)ethyl Phosphate Esters of Adenine Nucleotide Analogues. Synthesis and Mechanism of Photolysis" 1988; J am Chem Soc, 110: 7170-7177.

Wang et al., "Manipulation of gene expression in zebrafish using caged circular morpholino oligomers" 2012, Nucleic Acids Res. 40:11155-11162.

Wilker et al., "Substrates for Rapid Delivery of Electrons and Holes to Buried Active Sites in Proteins" 1999, Angew. Chem. Int. Ed. 38: 89-92.

Wu et al. "Caged ciruclar antisense oligonucleotides for photomdulation of RNA digestion and gene expression in cells." Nucleic Acids Research. 2013. 41(1):677-686. (Year: 2013).

Wu et al., "Caged circular antisense oligonucleotides for photomodulation of RNA digestion and gene expression in cells" 2013, Nucleic Acids Res. 41:677-686.

(56) References Cited

OTHER PUBLICATIONS

Yamazoe et al., "Cyclic Caged Morpholinos: Conformationally Gated Probes of Embryonic Gene Function" 2012, Angew. Chem., Int. Ed. 51:6908-6911.
Yamazoe et al., "Sequential Gene Silencing Using Wavelength-Selective CagedMorpholino Oligonucleotides" 2014, Angew. Chem., Int. Ed. 53:10114-10118.
Young and Deiters, "Photochemical control of biological processes" 2007, Org. Biomol. Chem. 5:999-1005.
Zayat et al., "A New Strategy for Neurochemical Photodelivery: Metal-Ligand Heterolytic Cleavage" 2003, J. Am. Chem. Soc. 125:882-883.
Zayat et al., "Ruthenium polypyridyl phototriggers: from beginnings to perspectives" 2013, Philos. Trans. R. Soc., A 371:20120330.
Zayat et al., "Ruthenium(II) Bipyridyl Complexes as Photolabile Caging Groups for Amines" 2006, Inorg. Chem. 45:1728-1731.
Zeng et al., "A protocol for PAIR: PNA-assisted identification of RNA binding proteins in living cell" 2006, J. Nat. Protoc., 1, 920-927.
Zielinski et al., "In vivo identification of ribonucleoprotein-RNA interactions" 2006, J. Proc. Natl. Acad. Sci., U.S.A., 103, 1557-1562.
Albani et al., "New cyclometallated Ru(II) complex for potential application in photochemotherapy?" 2014, Photochem. Photobiol. Sci. 13:272-280.
Albani et al., "Selective Photoinduced Ligand Exchange in a New Tris-Heteroleptic Ru(II) Complex" 2013, J. Phys. Chem. A 117:13885-13892.
Andaloussi et al., "Design of a peptide-based vector, PepFect6, for efficient delivery of siRNA in cell culture and systemically in vivo" 2011, Nucleic Acids Res, 39(9): 3972-3987.
Ando et al., "Photo-mediated gene activation using caged RNA/DNA in zebrafish embryos" 2001, Nat. Genet. 28:317-325.
Araya et al., "Two-Photon Optical Interrogation of Individual Dendritic Spines with Caged Dopamine" 2013, ACS Chem. Neurosci. 4:1163-1167.
Aujard et al., "o-Nitrobenzyl Photolabile Protecting Groups with Red-Shifted Absorption:Syntheses and Uncaging Cross-Sections for One- and Two-Photon Excitation" 2006, Chemistry—Eur. J., 12: 6865-6879.
Badaeva et al., "Effect of deprotonation on absorption and emission spectra of Ru(II)-bpy complexes functionalized with carboxyl groups" 2010, Phys. Chem. Chem. Phys. 12: 8902-8913.
Balzani et al., "Photochemistry and photophysics of Ru(II)polypyridine complexes in the Bologna group. From early studies to recent developments" 2001, Coord. Chem. Rev. 211: 97-115.
Baron et al., "Click Chemistry on a Ruthenium Polypyridine Complex. An Efficient and Versatile Synthetic Route for the Synthesis of Photoactive Modular Assemblies" 2012, Inorg. Chem., 51: 5985-5987.
Blinder et al. "Photoinduced RNA interference using DMNPE-caged 2'-deoxy-2'-fluoro substituted nucleic acids in vitro and in vivo." Mol. BioSyst. 2008. 4:431-440. (Year: 2008).
Boyden et al., "Millisecond-timescale, genetically targeted optical control of neural activity" 2005, Nat. Neurosci. 8:1263-1268.
Bryant and Mayer, "Oxidation of C—H Bonds by [(bpy)2(py)RuIVO]2+ Occurs by Hydrogen Atom Abstraction" 2003, J. Am. Chem. Soc. 125:10351-10361.
Chambers et al., "Cryptophane Xenon-129 Nuclear Magnetic Resonance Biosensors Targeting Human Carbonic Anhydrase" 2009, J. Am. Chem. Soc., 131: 563-569.
Corrie et al., "Photolytic Cleavage of 1-(2-Nitrophenyl)ethyl Ethers Involves Two Parallel Pathways and Product Release Is Rate-Limited by Decomposition of a Common Hemiacetal Intermediate" 2003, J Am Chem Soc, 125: 8546-8554.
Deiters et al., "Photocaged Morpholino Oligomers for the Light-Regulation of Gene Function in Zebrafish and Xenopus Embryos" 2010, J. Am. Chem. Soc. 132:15644-15650.
Del Mármol et al., "A Ruthenium-Rhodamine Complex as an Activatable Fluorescent Probe" 2010, Anal. Chem. 82:6259-6264.
Derossi et al., "The Third Helix of the Antennapedia Homeodomain Translocates through Biological Membrane" 1994, J Biol Chem, 269, 10444-10450.
Dmochowski et al., "Taking control of gene expression with light-activated oligonucleotides" 2007, J Biotechniques, 43:161-171.
Berwine et al., "Analysis of gene expression in single live neurons" Proc Natl Acad Sci U S A 1992, 89, 3010-3014.
Ellis-Davies, "A chemist and biologist talk to each other about caged neurotransmitters" 2013, Beilstein J. Org. Chem. 9:64-73.
Ellis-Davies, "Neurobiology with Caged Calcium" 2008, Chem. Rev. 108:1603-1613.
Filevich and Etchenique, "RuBiGABA-2: a hydrophilic caged GABA with long wavelength sensitivity" 2013, Photochem. Photobiol. Sci. 12:1565-1570.
Fino et al., "RuBi-Glutamate: two-photon and visible-light photoactivation of neurons and dendritic spines" 2009, Front. Neural Circuits 3:1-9.
Furuta et al., "Brominated 7-hydroxycoumarin-4-ylmethyls: Photolabile protecting groups with biologically useful cross-sections for two photon photolysis" 1999, Proc. Natl. Acad. Sci. U.S.A. 96:1193-1200.
Garner et al., "[Ru(bpy)2(5-cyanouracil)2]2+ as a Potential Light-Activated Dual-Action Therapeutic Agent" 2011, Inorg. Chem. 50:9213-9215.
Garner et al., "Effect of Electronic Structure on the Photoinduced Ligand Exchange of Ru(II) Polypyridine Complexes" 2011, Inorg. Chem. 50:4384-4391.
Gatterdam et al., "Three-Dimensional Protein Networks Assembled by Two-PhotonActivation" 2014, Angew. Chem. Int. Ed. Engl. 53:5680-5684.
Griepenberg., "Regulating Gene Expression with Light-Activated Oligonucleotides.", 2014, 6 pages.
Griepenburg et al. "Caged oligonucleotides for bidirectional photomodulation of let-7 miRNA in zebrafish embryos." Bioorganic & Medicinal Chemistry. 2013. 21:6198-6204. (Year: 2013).
Griepenburg et al., "Caged oligonucleotides for bidirectional photomodulation of let-7 miRNA in zebrafish embryos" 2013, Bioorg Med Chem Lett, 21(20): 6198-6204.
Grzybowski et al., "Synthesis and antibody-mediated detection of oligonucleotides containing multiple 2,4-dinitrophenyl reporter groups" Nucl. Acids Res. 1993, 21, 1705-1712.
Guttman et al., "Chromatin signature reveals over a thousand highly conserved large non-coding RNAs in mammals" 2009, Nature, 458: 223-227.
Hill et al., "Substituent Effects on Xenon Binding Affinity and Solution Behavior of Water-Soluble Cryptophanes" 2009, J. Am. Chem. Soc., 131, 3069-3077.
Hill et al., "Thermodynamics of Xenon Binding to Cryptophane in Water and Human Plasma" 2007, J. Am. Chem. Soc. 129: 9262-9263.
Il'ichv et al., "Photochemical Reaction Mechanisms of 2-Nitrobenzyl Compounds: Methyl Ethers and Caged ATP" 2004, J Am Chem Soc, 126: 4581-4595.
Jayakumar et al., "Remote activation of biomolecules in deep tissues using near-infrared-to-UV upconversion hanotransducers" 2012, Proc. Natl. Acad. Sci. U.S.A. 8483-8488.
Juliano et al., "Mechanisms and strategies for effective delivery of antisense and siRNA oligonucleotides" Nucl. Acids. Res. 2008, 36, 4158-4171.
Kanemoto et al., "Spatial Distributions of GABA Receptors and Local Inhibition of Ca2+ Transients Studied with GABA Uncaging in the Dendrites of CA1 Pyramidal Neurons" 2011, PLoS ONE, 6: e22652.
Klan et al., "Photoremovable Protecting Groups in Chemistry and Biology : Reaction Mechanisms and Efficacy", Chemical Reviews, (2013), vol. 113, doi:doi: 10.1021/cr300177k, pp. 119-191, XP055049223.
Kolb et al., "Click Chemistry: Diverse Chemical Function from a Few Good Reactions" 2001, Angew Chem Int Ed., 40: 2004-2021.
Kumar et al., "Transvascular delivery of small interfering RNA to the central nervous system" Nature 2007, 448, 39-43.
Li et al., "Folate-Mediated Targeting of Antisense Oligodeoxynucleotides to Ovarian Cancer Cells" Pharm Res. 1998, 10, 1540-1545.

(56) References Cited

OTHER PUBLICATIONS

Lovatt et al., "Transcriptome In Vivo Analysis (TIVA) of spatially defined single cells in intact live mouse and human brain tissue" 2014, Nat Methods, 11(2): 190-196.

Matsuzaki et al., "Two-photon uncaging of γ-aminobutyric acid in intact brain tissue" 2010, Nat Chem Biol, 6: 255-257.

McCray et al., "A New Approach to Time-Resolved Studies of ATP-Requiring Biological Systems: Laser Flash Photolysis of Caged ATP" 1980, Proc Natl Acad Sci USA, 77: 7237-7241.

Morris et al., "Transcriptome Analysis of Single Cells" J. Vis. Exp. 2011, 50, e2634.

Nikolenko et al, "Two-Photon Mapping of Neural Circuits" 2011, Cold Spring Harbor Protocols, 2011: 496-498.

Nikolenko et al., "Two-photon uncaging of neurochemicals using inorganic metal complexes" 2005, Chem. Commun. 2005: 1752-1754.

O'Connor et al., "A covalently linked phenanthridine-ruthenium(II) complex as a RNA probe", Chemical Communications, (2009), vol. 19, pp. 2640-2642.

O'Dell et al., "Amplification of mRNAs from Single, Fixed, TUNEL-Positive Cells", BioTechniques, (1998), vol. 25, No. 4, pp. 566-568, 570, XP001042378.

* cited by examiner

Figure 36A Photolysis – uncaging of TISA

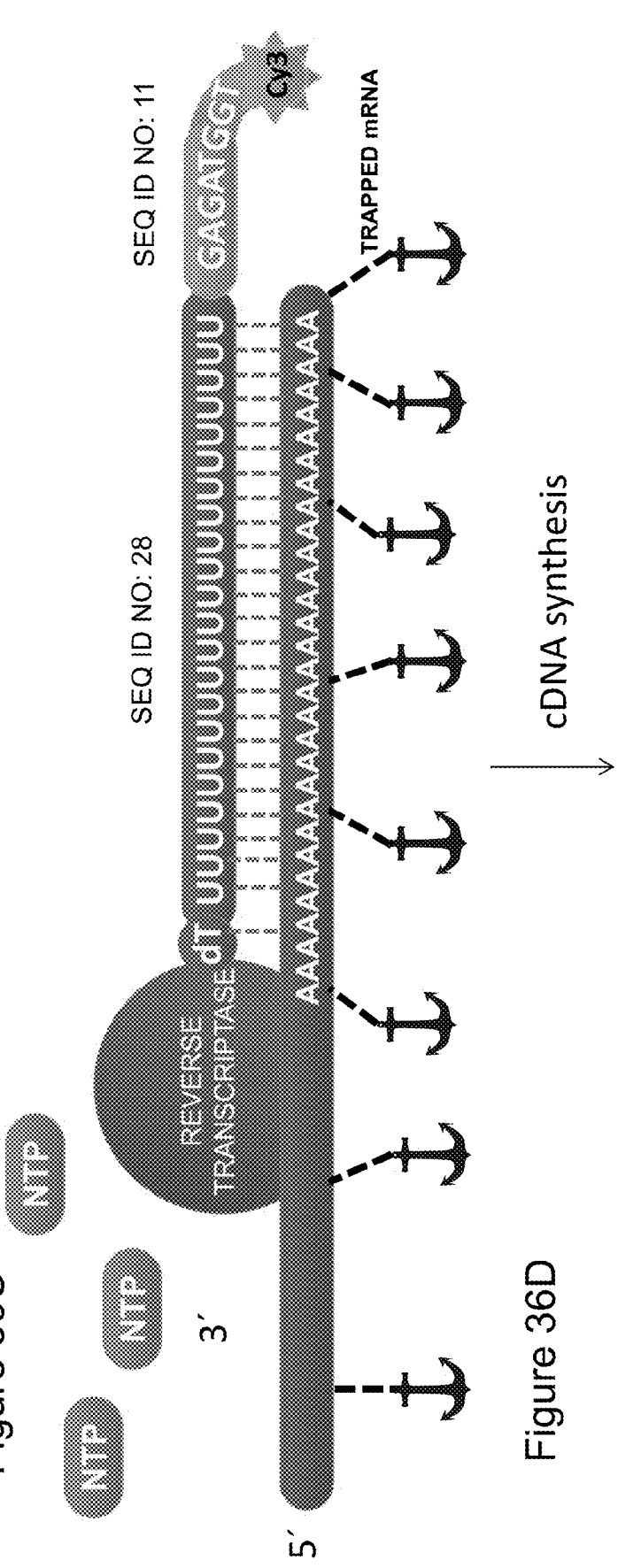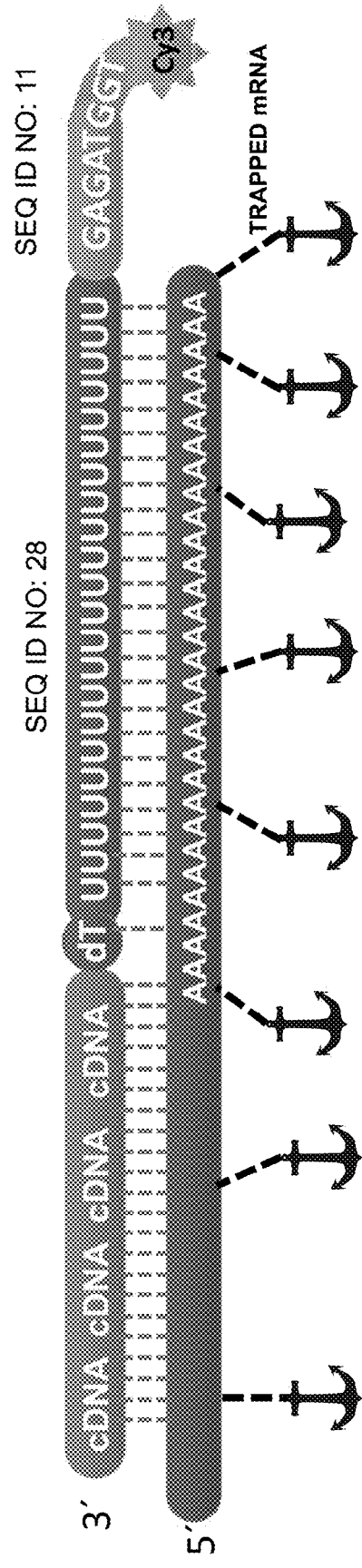
Figure 36C
Figure 36D

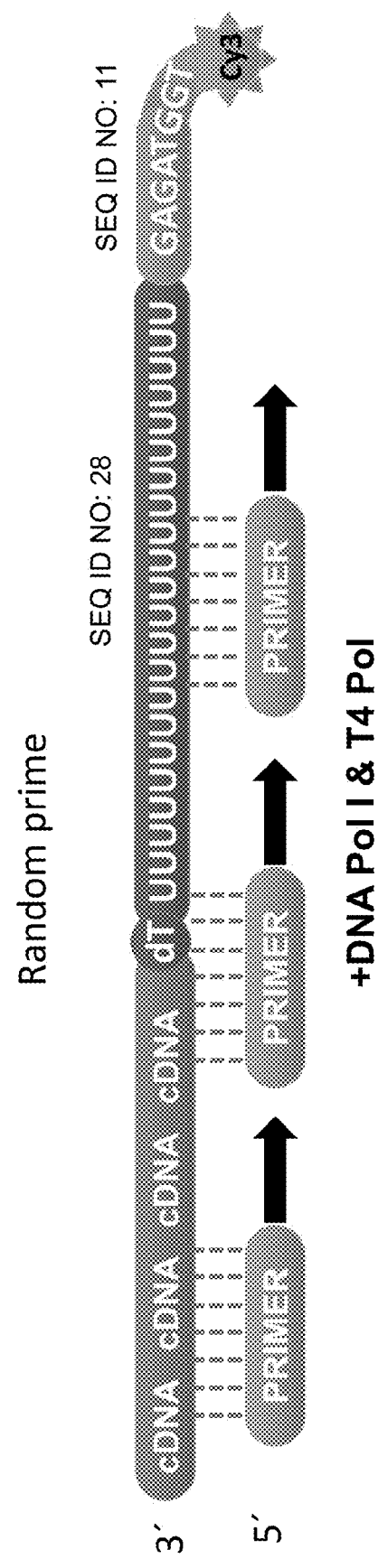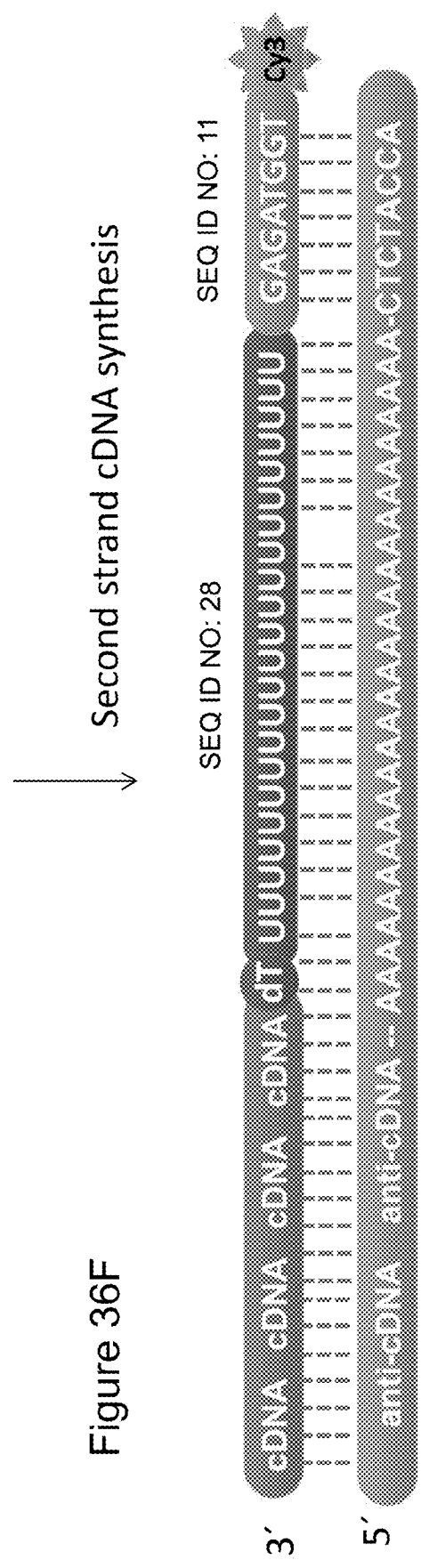
Figure 36E
Figure 36F

Figure 36G

Bind index-T7 oligo

SEQ ID NO: 41
SEQ ID NO: 11
T7 promoter
SEQ ID NO: 42

+DNA Pol I & T4 Pol

Production of ds-cDNA which includes T7 promoter

Figure 36H

SEQ ID NO: 41
SEQ ID NO: 11
SEQ ID NO: 42

IVT

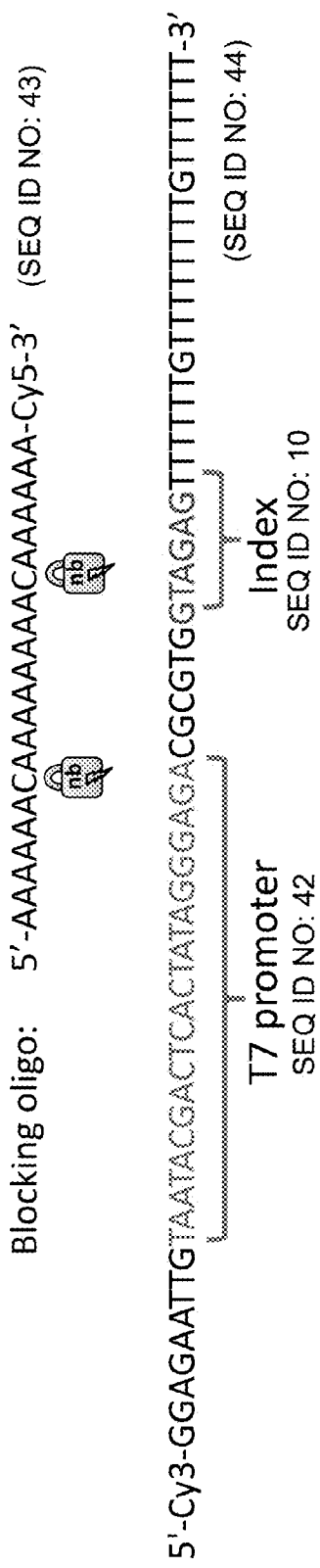
Figure 38A
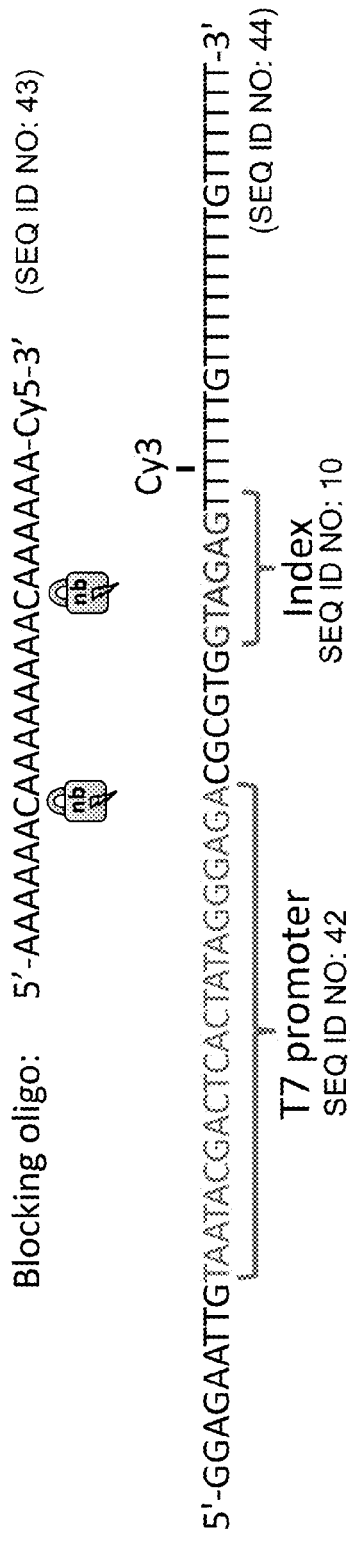
Figure 38B
Figure 38

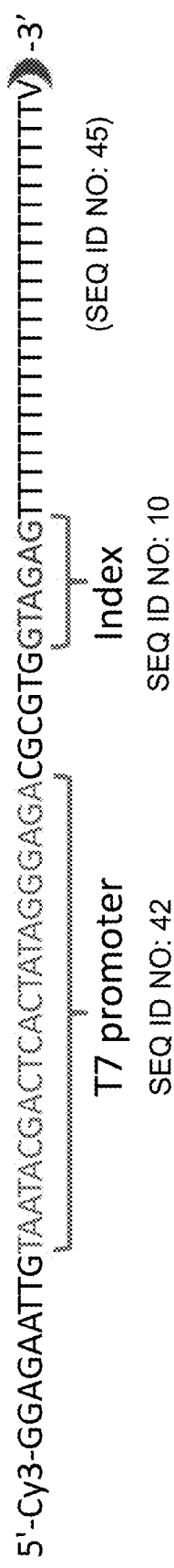
Figure 39A
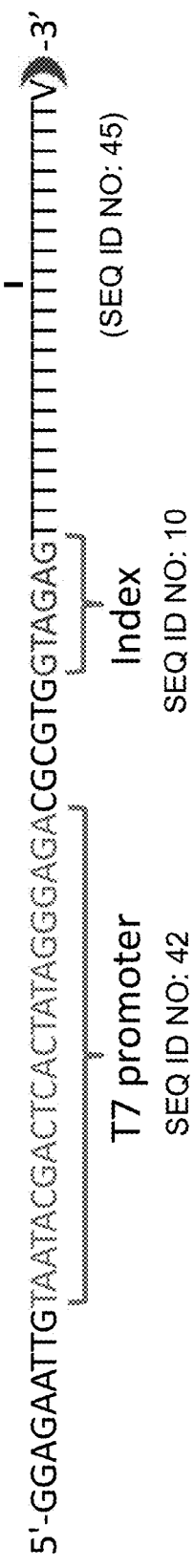
Figure 39B
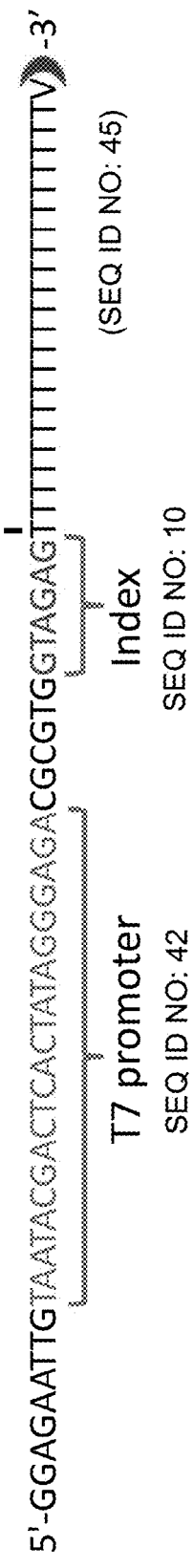
Figure 39C
Figure 39

SEQUENCE LISTING

```
<160> NUMBER OF SEQ ID NOS: 45

<210> SEQ ID NO 1
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 2

Gly Arg Lys Lys Arg Arg Gln Arg Arg Arg Pro Pro Gln
1               5                   10

<210> SEQ ID NO 3
<211> LENGTH: 27
<212> TYPE: PRT
<213> ORGANISM: Artificial Sequence
<220> FEATURE:
<223> OTHER INFORMATION: Chemically Synthesized

<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 4

Arg Arg Arg Arg Arg Arg Arg Arg Arg
1               5

<210> SEQ ID NO 5
```

-continued

```
<211> LENGTH: 24
<212> TYPE: PRT
<213> ORGANISM: Artificial Sequence
<220> FEATURE:
<223> OTHER INFORMATION: Chemically Synthesized

<400> SEQUENCE: 5

Gly Ala Leu Phe Leu Gly Trp Leu Gly Ala Ala Gly Ser Thr Met Gly
1               5                   10                  15

Ala Pro Lys Lys Lys Arg Lys Val
            20

<210> SEQ ID NO 6
<211> LENGTH: 30
<212> TYPE: PRT
<213> ORGANISM: Artificial Sequence
<220> FEATURE:
<223> OTHER INFORMATION: Chemically Synthesized

<400> SEQUENCE: 6

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 7
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 7

Asp Tyr Lys Asp Asp Asp Asp Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 8

Tyr Pro Tyr Asp Val Pro Asp Tyr Ala
1               5

<210> SEQ ID NO 9
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 9

Glu Gln Lys Leu Ile Ser Glu Glu Asp Leu
1               5                   10

<210> SEQ ID NO 10
<211> LENGTH: 6
<212> TYPE: DNA
<213> ORGANISM: Artificial Sequence
<220> FEATURE:
<223> OTHER INFORMATION: Chemically Synthesized

<400> SEQUENCE: 10
``` gtagag                                                                          6

<210> SEQ ID NO 11
<211> LENGTH: 8
<212> TYPE: DNA
<213> ORGANISM: Artificial Sequence
<220> FEATURE:
<223> OTHER INFORMATION: Chemically Synthesized

<400> SEQUENCE: 11 tggtagag                                                                        8

<210> SEQ ID NO 12
<211> LENGTH: 12
<212> TYPE: DNA
<213> ORGANISM: Artificial Sequence
<220> FEATURE:
<223> OTHER INFORMATION: Chemically Synthesized

<400> SEQUENCE: 12
uuuuuuuuuu uu                                                                  12

<210> SEQ ID NO 13
<211> LENGTH: 12
<212> TYPE: DNA
<213> ORGANISM: Artificial Sequence
<220> FEATURE:
<223> OTHER INFORMATION: Chemically Synthesized

<400> SEQUENCE: 13
aaaaaaaaaa aa                                                                  12

<210> SEQ ID NO 14
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 14
gacttgaggc aggcatattt ccgat                                                    25

<210> SEQ ID NO 15
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 15
gaaauaugcc ugccucaagu c                                                        21

<210> SEQ ID NO 16
<211> LENGTH: 18
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(18)
<223> OTHER INFORMATION: 2' Fluoro-uridine

<400> SEQUENCE: 16
uuuuuuuuuu uuuuuuuu                                                            18

```
<210> SEQ ID NO 17
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 17
atcgatcgat cgatcgat                                                 18

<210> SEQ ID NO 18
<211> LENGTH: 30
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(1)
<223> OTHER INFORMATION: dT-amine
<220> FEATURE:
<221> NAME/KEY: modified_base
<222> LOCATION: (7)..(24)
<223> OTHER INFORMATION: 2' Fluoro-uridine
<220> FEATURE:
<221> NAME/KEY: modified_base
<222> LOCATION: (30)..(30)
<223> OTHER INFORMATION: dT-amine

<400> SEQUENCE: 18
taagaauuuu uuuuuuuuuu uuuuuucuut                                    30

<210> SEQ ID NO 19
<211> LENGTH: 26
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(1)
<223> OTHER INFORMATION: dT-amine
<220> FEATURE:
<221> NAME/KEY: misc_feature
<222> LOCATION: (5)..(22)
<223> OTHER INFORMATION: n is a, c, g, t or u
<220> FEATURE:
<221> NAME/KEY: modified_base
<222> LOCATION: (26)..(26)
<223> OTHER INFORMATION: dT-amine

<400> SEQUENCE: 19
tgcgnnnnnn nnnnnnnnnn nncgct                                        26

<210> SEQ ID NO 20
<211> LENGTH: 24
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(21)
<223> OTHER INFORMATION: n is a, c, g, t or u

<400> SEQUENCE: 20
gcgnnnnnnn nnnnnnnnnn ncgc                                          24

<210> SEQ ID NO 21
<211> LENGTH: 34
<212> TYPE: DNA
```

```
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(1)
<223> OTHER INFORMATION: dT-amine
<220> FEATURE:
<221> NAME/KEY: misc_feature
<222> LOCATION: (9)..(26)
<223> OTHER INFORMATION: n is a, c, g, t or u
<220> FEATURE:
<221> NAME/KEY: modified_base
<222> LOCATION: (34)..(34)
<223> OTHER INFORMATION: dT-amine

<400> SEQUENCE: 21
tggtagagnn nnnnnnnnnn nnnnnnctct acct                                  34

<210> SEQ ID NO 22
<211> LENGTH: 20
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(3)
<223> OTHER INFORMATION: n is a, c, g, t or u
<220> FEATURE:
<221> NAME/KEY: modified_base
<222> LOCATION: (4)..(4)
<223> OTHER INFORMATION: dT-amine
<220> FEATURE:
<221> NAME/KEY: misc_feature
<222> LOCATION: (5)..(16)
<223> OTHER INFORMATION: n is a, c, g, t or u
<220> FEATURE:
<221> NAME/KEY: modified_base
<222> LOCATION: (17)..(17)
<223> OTHER INFORMATION: dT-amine
<220> FEATURE:
<221> NAME/KEY: misc_feature
<222> LOCATION: (18)..(20)
<223> OTHER INFORMATION: n is a, c, g, t or u

<400> SEQUENCE: 22
nnntnnnnnn nnnnnntnnn                                                  20

<210> SEQ ID NO 23
<211> LENGTH: 7
<212> TYPE: DNA
<213> ORGANISM: Artificial Sequence
<220> FEATURE:
<223> OTHER INFORMATION: Chemically Synthesized

<400> SEQUENCE: 23 aaaaaaa                                                                 7

<210> SEQ ID NO 24
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 24
uuuuuuuuuu uuuuuuut                                                    18

<210> SEQ ID NO 25
<211> LENGTH: 26
```

```
<212> TYPE: RNA
<213> ORGANISM: Artificial Sequence
<220> FEATURE:
<223> OTHER INFORMATION: Chemically Synthesized

<400> SEQUENCE: 25
aucgaucgaa aaaaaaaaaa aaaaaa                                          26

<210> SEQ ID NO 26
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 26
uuuuuuuuuu uuuuuuutcg atcgat                                          26

<210> SEQ ID NO 27
<211> LENGTH: 9
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(9)
<223> OTHER INFORMATION: 2'-O-Methyl-A

<400> SEQUENCE: 27 aaaaaaaaa                                                              9

<210> SEQ ID NO 28
<211> LENGTH: 22
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(22)
<223> OTHER INFORMATION: 2' Fluoro-uridine

<400> SEQUENCE: 28
uuuuuuuuuu uuuuuuuuuu uu                                              22

<210> SEQ ID NO 29
<211> LENGTH: 12
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(12)
<223> OTHER INFORMATION: 2' O-Methyl-A

<400> SEQUENCE: 29
aaaaaaaaaa aa                                                         12

<210> SEQ ID NO 30
<211> LENGTH: 10
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(7)
```

```
<223> OTHER INFORMATION: 2' O-Methyl-A

<400> SEQUENCE: 30
aaaaaaactc                                                            10

<210> SEQ ID NO 31
<211> LENGTH: 8
<212> TYPE: DNA
<213> ORGANISM: Artificial Sequence
<220> FEATURE:
<223> OTHER INFORMATION: Chemically Synthesized

<400> SEQUENCE: 31 tgagttcc                                                               8

<210> SEQ ID NO 32
<211> LENGTH: 8
<212> TYPE: DNA
<213> ORGANISM: Artificial Sequence
<220> FEATURE:
<223> OTHER INFORMATION: Chemically Synthesized

<400> SEQUENCE: 32 tgggtagc                                                               8

<210> SEQ ID NO 33
<211> LENGTH: 8
<212> TYPE: DNA
<213> ORGANISM: Artificial Sequence
<220> FEATURE:
<223> OTHER INFORMATION: Chemically Synthesized

<400> SEQUENCE: 33 tgatgagc                                                               8

<210> SEQ ID NO 34
<211> LENGTH: 11
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(8)
<223> OTHER INFORMATION: 2'-O-Methyl-A

<400> SEQUENCE: 34
aaaaaaaact c                                                          11

<210> SEQ ID NO 35
<211> LENGTH: 8
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(8)
<223> OTHER INFORMATION: 2' Fluoro-uridine

<400> SEQUENCE: 35 uuuuuuuu                                                               8

<210> SEQ ID NO 36
<211> LENGTH: 14
<212> TYPE: DNA
<213> ORGANISM: Artificial Sequence
```

```
<220> FEATURE:
<223> OTHER INFORMATION: Chemically Synthesized
<220> FEATURE:
<221> NAME/KEY: modified_base
<222> LOCATION: (1)..(14)
<223> OTHER INFORMATION: 2' Fluoro-uridine

<400> SEQUENCE: 36
uuuuuuuuuu uuuu                                                         14

<210> SEQ ID NO 37
<211> LENGTH: 11
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(11)
<223> OTHER INFORMATION: 2'-O-Methyl-A

<400> SEQUENCE: 37
aaaaaaaaaa a                                                            11

<210> SEQ ID NO 38
<211> LENGTH: 10
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(10)
<223> OTHER INFORMATION: 2'-O-Methyl-A

<400> SEQUENCE: 38
aaaaaaaaaa                                                              10

<210> SEQ ID NO 39
<211> LENGTH: 24
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(24)
<223> OTHER INFORMATION: 2'-Fluoro-uridine

<400> SEQUENCE: 39
uuuuuuuuuu uuuuuuuuuu uuuu                                              24

<210> SEQ ID NO 40
<211> LENGTH: 7
<212> TYPE: DNA
<213> ORGANISM: Artificial Sequence
<220> FEATURE:
<223> OTHER INFORMATION: Chemically Synthesized
<220> FEATURE:
<221> NAME/KEY: modified_base
<222> LOCATION: (1)..(7)
<223> OTHER INFORMATION: 2'-O-Methyl-A

<400> SEQUENCE: 40 aaaaaaa                                                                  7

<210> SEQ ID NO 41
<211> LENGTH: 8
<212> TYPE: DNA
```

```
<213> ORGANISM: Artificial Sequence
<220> FEATURE:
<223> OTHER INFORMATION: Chemically Synthesized

<400> SEQUENCE: 41 ctctacca                                                                 8

<210> SEQ ID NO 42
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 42
taatacgact cactataggg aga                                               23

<210> SEQ ID NO 43
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 43
aaaaaacaaa aaaaacaaaa aa                                                22

<210> SEQ ID NO 44
<211> LENGTH: 66
<212> TYPE: DNA
<213> ORGANISM: Artificial Sequence
<220> FEATURE:
<223> OTHER INFORMATION: Chemically Synthesized

<400> SEQUENCE: 44
ggagaattgt aatacgactc actataggga gacgcgtggt agagtttttt gtttttttg        60 tttttt                                                                  66

<210> SEQ ID NO 45
<211> LENGTH: 67
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (67)..(67)
<223> OTHER INFORMATION: photoactivatable dideoxynucleotide

<400> SEQUENCE: 45
ggagaattgt aatacgactc actataggga gacgcgtggt agagtttttt tttttttttt       60 tttttv                                                                  67
```

TRANSCRIPTOME IN VIVO ANALYSIS (TIVA) AND TRANSCRIPTOME IN SITU ANALYSIS (TISA)

CROSS-REFERENCE TO RELATED APPLICATIONS

This application is a divisional of U.S. patent application Ser. No. 15/501,073, filed Feb. 1, 2017, which is a U.S. national phase application filed under 35 U.S.C. § 371 claiming priority to International Patent Application No. PCT/US2015/043581, filed Aug. 4, 2015, which is entitled to priority under 35 U.S.C. § 119(e) to U.S. Provisional Patent Application Nos. 62/033,007, filed Aug. 4, 2014, and 62/035,410, filed Aug. 9, 2014, each of which applications is hereby incorporated herein by reference in its entirety.

STATEMENT REGARDING FEDERALLY SPONSORED RESEARCH OR DEVELOPMENT

This invention was made with government support under R01 GM083030 and U01MH098953 awarded by the National Institute of Health. The government has certain rights in the invention.

BACKGROUND OF THE INVENTION

Single cells are the building blocks upon which complex tissue and biological systems are developed. It is believed that a detailed molecular fingerprint of individual cells in the context of the other cells within the system would provide a blueprint for manipulation of the system in an effort to produce predictable outcomes.

It has been possible to isolate and analyze the mRNA complement from individual cells for several years, in particular with regard to dispersed cells in culture. This information is intriguing but lacks the "systemic" regulation component associated with the cell being in intact live tissue.

While several tools have been developed to isolate mRNA from target cells, these tools have lacked the ability to effectively detect or compare nucleic acid molecules longitudinally or among different cells or subcellular compartments (e.g., multiplex). Further, the ability to effectively capture all RNA, and not just polyA+ mRNA has remained elusive.

Fixed tissue samples remain popular for various types of molecular or biochemical investigations. However, the ability to fully analyze their RNA fingerprint is compromised due to the crosslinking of the RNA within the sample.

There is a need in the art for improved compositions and methods to detect the nucleic acid fingerprint of single cells in live and fixed tissue samples. The present invention satisfies this need.

SUMMARY OF THE INVENTION

In one aspect, the present invention provides a caged molecule for capturing one or more nucleic acid molecules. In one embodiment, the caged molecule comprises an antisense oligonucleotide linked to a ruthenium-based photolinker compound of formula (II):

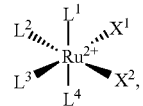

wherein in formula (II): $L^1$, $L^2$, $L^3$, and $L^4$ are each independently a ligand; and $X^1$ and $X^2$ are each independently a photolabile ligand having a reactive moiety.

In one embodiment, the molecule further comprises a label for isolating nucleic acids. In one embodiment, the molecule further comprises a cell penetrating domain.

In one embodiment, the antisense oligonucleotide is at least an 18mer 2'fluoro oligonucleotide having a nucleic acid sequence that is substantially complementary to the polyA tail of an mRNA.

In one embodiment, the molecule is a circular caged molecule wherein a first end of the antisense oligonucleotide is directly or indirectly linked to a first photolabile ligand of the ruthenium-based photolinker and a second end of the antisense oligonucleotide is directly or indirectly linked elsewhere on the compound. In one embodiment, the second end of the antisense oligonucleotide is directly or indirectly linked to a second photolabile ligand of the ruthenium-based photolinker.

In one embodiment, the molecule further comprises one or more fluorophores. In one embodiment, the one or more molecules is a FRET pair.

In one embodiment, the antisense oligonucleotide comprises a randomized nucleotide sequence.

In one embodiment, irradiation of ruthenium-based photolinker exposes the antisense oligonucleotide thereby allowing the antisense oligonucleotide to hybridize with a nucleic acid.

In one embodiment, the molecule is a hairpin caged molecule comprising a stem and a loop, wherein the molecule comprises a first stem-forming oligonucleotide and a second stem-forming oligonucleotide, wherein the first stem-forming oligonucleotide and a second stem-forming oligonucleotide hybridize to form the stem and wherein the loop comprises the antisense oligonucleotide. In one embodiment, a first end of the first stem-forming oligonucleotide is directly or indirectly linked to a first photolabile ligand of the ruthenium-based photolinker and wherein a first end of the second stem-forming oligonucleotide is directly or indirectly linked to a second photolabile ligand of the ruthenium-based photolinker.

In one aspect, the invention provides a method of capturing nucleic acid in a cell. In one embodiment, the method comprises administering to the cell a composition comprising a caged molecule comprising an antisense oligonucleotide conjugated to the at least one ruthenium-based photolinker compound of formula (II):

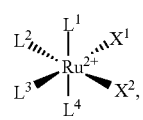

wherein in formula (II): $L^1$, $L^2$, $L^3$, and $L^4$ are each independently a ligand; and $X^1$ and $X^2$ are each independently a photolabile ligand having a reactive moiety.

In one embodiment, the method further comprises irradiating the cell thereby cleaving the ruthenium-based photolinker compound and exposing the antisense oligonucleotide under conditions suitable for binding of the antisense oligonucleotide to a nucleic acid of the cell, thereby forming a complex. In one embodiment, the method further comprises isolating the complex. In one embodiment, irradiating the cell comprises administering light at a wavelength in the range of about 350-1500 nm. In one embodiment, irradiating the cell comprises exposing the cell to two-photon excitation of near-infrared or infrared light.

In one embodiment, the caged molecule is complexed with at least one selected from the group of a lipid, liposome, micelle, and a nanoparticle, to allow entry of the caged molecule to the cell.

In one embodiment, the method comprises administering to the cell a plurality of caged molecules, each molecule comprising an antisense oligonucleotide comprising a random nucleotide sequence conjugated to a ruthenium-based photolinker. In one embodiment, the method comprises irradiating the cell, thereby exposing the antisense oligonucleotides of all of the plurality of molecules and thereby capturing substantially all of the RNA of the cell. In one embodiment, the captured RNA includes microRNAs, lincRNAs, piwi-interacting RNAs, intron-containing RNAs, hnRNAs, poly-A+ mRNA and poly-A− mRNA.

In one aspect, the invention provides a caged nucleic acid molecule comprising: a first, second, and third oligonucleotide, wherein the first oligonucleotide is linked to the second oligonucleotide through a first photocleavable linker and the second oligonucleotide is linked to the third oligonucleotide through a second photocleavable linker, wherein the first oligonucleotide comprises one or more terminal deoxynucleotides. In one embodiment, the second oligonucleotide and third oligonucleotide each comprise a nucleotide sequence that is complementary to the first oligonucleotide, thereby forming a hairpin where the first oligonucleotide hybridizes to both the second oligonucleotide and third oligonucleotide.

In one embodiment, the first oligonucleotide comprises an antisense oligonucleotide comprising a nucleic acid sequence that is substantially complementary to the polyA tail of an mRNA. In one embodiment, the first oligonucleotide comprises a 22mer 2'-fluoro uridine. In one embodiment, the one or more terminal deoxynucleotides comprises one or more thymidines.

In one embodiment, the molecule further comprises an index oligonucleotide. In one embodiment, the molecule further comprises one or more fluorophores. In one embodiment, the one or more fluorophores is a FRET pair.

In one embodiment, irradiation of photocleavable linkers exposes the antisense oligonucleotide thereby allowing the antisense oligonucleotide to hybridize with a target nucleic acid. In one embodiment, the first photocleavable linker and the second photocleavable linker comprise nitrobenzyl. In one embodiment, the first oligonucleotide and one or more deoxynucleotides serve as a primer to synthesize cDNA from the target nucleic acid.

In one aspect, the invention provides a method of detecting a nucleic acid molecule from a cell, the method comprising the steps of: introducing a hybrid nucleic acid molecule into the cell, the hybrid nucleic acid molecule comprising a first, second, and third oligonucleotide, wherein the first oligonucleotide is linked to the second oligonucleotide through a first photocleavable linker and the second oligonucleotide is linked to the third oligonucleotide through a second photocleavable linker, wherein the first oligonucleotide comprises one or more terminal deoxynucleotides and an antisense oligonucleotide comprising a nucleic acid sequence that is substantially complementary to a target nucleic acid molecule of the cell; activating the molecule under conditions suitable for binding of the first oligonucleotide to the target nucleic acid molecule of the cell, wherein the activation cleaves the photocleavable linkers in the molecule; allowing the formation of a complex comprising the target nucleic acid molecule hybridized to the first oligonucleotide; and synthesizing cDNA from the target nucleic acid molecule, using the first oligonucleotide and one or more terminal deoxynucleotides as a primer.

In one embodiment, the antisense oligonucleotide comprises a nucleic acid sequence that is substantially complementary to the polyA tail of an mRNA, and where the method detects the mRNA transcriptome of the cell.

In one embodiment, the molecule further comprises an index oligonucleotide. In one embodiment, the method comprises administering to the cell a plurality of molecules, each molecule comprising a different index oligonucleotide.

In one embodiment, the method further comprises processing the synthesized cDNA to generate a double-stranded cDNA comprising the index oligonucleotide and a promoter region.

In one embodiment, the cell is fixed. In one embodiment, the cell is in a fixed tissue sample. In one embodiment, the fixed tissue sample is immunostained to distinguish between two or more cell types. In one embodiment, the fixed tissue sample is stained to distinguish between two or more subcellular compartments.

In one embodiment, activation of the molecule comprises administering ultraviolet light to the cell. In one embodiment, activation of the molecule comprises administering light to the cell, wherein the light has a wavelength of about 350 nm-1500 nm. In one embodiment, activation of the molecule comprises exposing the cell to two photon excitation of near-infrared or infrared light.

In one aspect, the present invention provides a hybrid nucleic acid molecule comprising: a first oligonucleotide and a second oligonucleotide, wherein the first oligonucleotide comprises an antisense oligonucleotide that is substantially complementary to a target nucleic acid molecule, wherein the second oligonucleotide comprises a nucleotide sequence that is substantially complementary to the antisense oligonucleotide of the first oligonucleotide, and wherein the second oligonucleotide comprises one or more photocleavable linkers.

In one embodiment, the first oligonucleotide comprises an index oligonucleotide. In one embodiment, the first oligonucleotide comprises a promoter region. In one embodiment, irradiation of photocleavable linkers exposes the antisense oligonucleotide thereby allowing the antisense oligonucleotide to hybridize with a target nucleic acid.

In one aspect, the present invention provides a method of detecting a nucleic acid molecule from a cell, the method comprising the steps of: introducing a hybrid nucleic acid molecule into the cell, the hybrid nucleic acid molecule comprising: a first oligonucleotide and a second oligonucleotide, wherein the first oligonucleotide comprises an antisense oligonucleotide that is substantially complementary to a target nucleic acid molecule, wherein the second oligonucleotide comprises a nucleotide sequence that is substantially complementary to the antisense oligonucleotide of the first oligonucleotide, and wherein the second oligonucleotide comprises one or more photocleavable linkers; activating the molecule under conditions suitable for binding of the first oligonucleotide to the target nucleic acid molecule of the cell, wherein the activation cleaves the photocleavable linkers in the molecule; allowing the formation of a complex comprising the target nucleic acid molecule hybridized to the first oligonucleotide; and synthesizing cDNA from the target nucleic acid molecule, using the first oligonucleotide as a primer.

In one embodiment, the method comprises administering to the cell a plurality of molecules, each molecule comprising a different index oligonucleotide.

In one embodiment, the method further comprises processing the synthesized cDNA to generate a double-stranded cDNA comprising the index oligonucleotide and a promoter region.

In one embodiment, the cell is fixed. In one embodiment, the cell is in a fixed tissue sample. In one embodiment, the fixed tissue sample is immunostained to distinguish between two or more cell types. In one embodiment, the fixed tissue sample is stained to distinguish between two or more subcellular compartments.

In one embodiment, activation of the molecule comprises administering ultraviolet light to the cell. In one embodiment, activation of the molecule comprises administering light to the cell, wherein the light has a wavelength of about 350 nm-1500 nm. In one embodiment, activation of the molecule comprises exposing the cell to two photon excitation of near-infrared or infrared light.

In one aspect, the present invention provides a hybrid nucleic acid molecule comprising: a first oligonucleotide, wherein the first oligonucleotide comprises an antisense oligonucleotide that is substantially complementary to a target nucleic acid molecule and a terminal photoactivatable dideoxynucleotide.

In one embodiment, the first oligonucleotide comprises an index oligonucleotide. In one embodiment, the first oligonucleotide comprises a promoter region. In one embodiment, the irradiation of the photoactivatable dideoxynucleotide allows cDNA synthesis of a target nucleic acid molecule hybridized to the antisense oligonucleotide.

In one aspect, the present invention provides a method of detecting a nucleic acid molecule from a cell, the method comprising the steps of: introducing a hybrid nucleic acid molecule into the cell, the hybrid nucleic acid molecule comprising: a first oligonucleotide, wherein the first oligonucleotide comprises an antisense oligonucleotide that is substantially complementary to a target nucleic acid molecule and a terminal photoactivatable dideoxynucleotide; allowing the formation of a complex comprising the target nucleic acid molecule hybridized to the first oligonucleotide; activating the molecule; and synthesizing cDNA from the target nucleic acid molecule.

In one embodiment, the first oligonucleotide comprises an index oligonucleotide. In one embodiment, the first oligonucleotide comprises a promoter region. In one embodiment, activating the molecule comprises photoactivation of the photoactivatable dideoxynucleoitde, which converts the dideoxynucleotide into a deoxynucleotide, thereby allowing for cDNA synthesis from the target nucleic acid molecule In one embodiment, the method comprises administering to the cell a plurality of molecules, each molecule comprising a different index oligonucleotide.

In one embodiment, the method further comprises processing the synthesized cDNA to generate a double-stranded cDNA comprising the index oligonucleotide and a promoter region.

In one embodiment, the cell is fixed. In one embodiment, the cell is in a fixed tissue sample. In one embodiment, the fixed tissue sample is immunostained to distinguish between two or more cell types. In one embodiment, the fixed tissue sample is stained to distinguish between two or more subcellular compartments.

In one embodiment, activation of the molecule comprises administering ultraviolet light to the cell. In one embodiment, activation of the molecule comprises administering light to the cell, wherein the light has a wavelength of about 350 nm-1500 nm. In one embodiment, activation of the molecule comprises exposing the cell to two photon excitation of near-infrared or infrared light.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4A and FIG. 4B, depict the characterization of circular Ru-oligonucleotide constructs. FIG. 4A is an illustration of circular Ru-TIVA with $Ru(bpy)_2X_2$ photocleavable linker, showing Cy3, Cy5, CPP, biotin. FIG. 4B is an image of a gel monitoring the click reaction of the joining of the two ends of a 25mer oligo to the Ru linker.

FIG. 36, comprising FIG. 36A through FIG. 36H, are a set of schematic illustrations of an exemplary TISA procedure. Upon loading of the caged molecule, photolysis of the photolinkers uncages the molecule (FIG. 36A) allowing the capture strand (antisense oligonucleotide) to bind to its mRNA target (FIG. 36B). Reverse transcriptase and dNTPs are added to the sample (FIG. 36C) which, using the terminal dT to initiate, results in the in situ synthesis of cDNA from the captured mRNA (FIG. 36D). Administering random primers and DNA Pol I and T4 Pol (FIG. 36E) results in the synthesis of second strand cDNA (FIG. 36F). An index-T7 oligonucleotide is administered to bind to the polyA stretch and anti-index of the second strand cDNA (FIG. 36G) which produces double stranded cDNA having the T7 promoter.

FIG. 38, comprising FIG. 38A and FIG. 38B, depict exemplary TISA-bandaid tags, where the capture strand comprises an antisense oligonucleotide, index, and promoter region. The Cy3 fluorophore may be placed at the 5' end of the capture strand (FIG. 38A) or internally within the capture strand (FIG. 38B).

FIG. 39, comprising FIG. 39A through FIG. 39C, depicts an exemplary single strand photoactivatable chain terminator TISA-tag, comprising an antisense oligonucleotide and a terminal photoactivatable dideoxynucleotide that prevents cDNA synthesis until photoactivated. A fluorophore may be placed at the 5' end of the oligonucleotide (FIG. 39A), internally within the antisense oligonucleotide (FIG. 39B), or at the 5' end of the antisense oligonucleotide (FIG. 39C).

DETAILED DESCRIPTION

Figure 1:
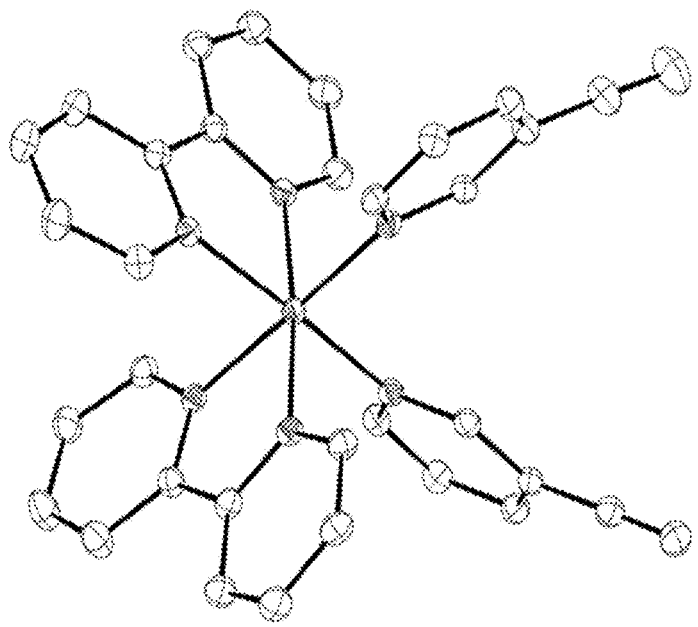
FIG. 1 depicts the crystal structure of RuBEP.

In one embodiment, the invention provides compositions and methods of capturing nucleic acid molecules from a cell or subcellular compartment. In certain embodiments, the invention is used to capture an mRNA transcriptome from a cell. In certain embodiments, the invention is used to capture total RNA from a cell or subcellular compartment. In certain embodiments, the invention is used to capture and compare nucleic acid molecules across multiple single cells or across multiple subcellular compartments.

In one embodiment, the compositions comprise a caged molecule comprising one or more photolinkers and an antisense oligonucleotide. In certain embodiments, irradiation of the photolinker exposes the antisense oligonucleotide, thereby allowing the antisense oligonucleotide to hybridize to one or more target nucleic acid molecules.

In certain embodiments, the invention is used to detect nucleic acid molecules from live cells. In certain embodiments, the invention is used to detect nucleic acid molecules from single cells or subcellular compartments within a fixed tissue sample.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

"Amplification" refers to any means by which a polynucleotide sequence is copied and thus expanded into a larger number of polynucleotide molecules, e.g., by reverse transcription, polymerase chain reaction, and ligase chain reaction, among other methods.

"Antisense" refers to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Binding" is used herein to mean that a first moiety interacts with a second moiety.

"Biological sample," as that term is used herein, means a sample obtained from a single-cellular or multi-cellular organism that can be used to assess the level of expression of a nucleic acid, the level of a protein present, or both. Such a sample includes, but is not limited to, a cell, a blood sample, a neural tissue sample, a brain sample, and a cerebrospinal fluid sample.

As used herein, a "pathological sample" is a biological sample from a subject having or suspected of having a disease, disorder or condition. Pathological specimens, include, but are not limited to, histological tissue sections and/or other biological preparations such as tissue culture cells and PAP smears. Pathological samples are commonly used in diagnostic pathology.

As used herein, a "fixed sample" is a sample that has been treated so as to preserve the structural organization of cells and tissues in the sample in as close a life-like state as possible for subsequent examination, for instance, by light or electron microscope. Fixation typically arrests autolysis and bacterial decomposition and stabilizes the structural organization of cellular and tissue constituents so that they withstand the subsequent stages of tissue processing.

"Caged" is used herein to describe a molecule that is in an inactive state. For example, in certain embodiments, a caged molecule has a conformation that prevents the activity of the molecule. In contrast, an "uncaged" molecule describes a molecule in an active state. In certain embodiments, an uncaged molecule has a conformation that allows the activity of the molecule. In certain embodiments, an uncaged molecule is generated from a corresponding caged molecule. For example, in one embodiment, a caged molecule is activated to become an uncaged molecule.

A "cell penetrating domain" is used herein to refer to a domain that facilitates the entry of said domain, along with any molecule associated with the domain, across one or more membranes to the interior of a cell.

A "cell penetrating peptide" is used herein to refer to a polypeptide that facilitates the entry of said polypeptide, along with any molecule associated with the polypeptide, across one or more membranes to the interior of a cell.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

As used herein, a "degenerate sequence" refers to sequence in which at one or more of the nucleotide positions, there are two or more types of nucleotides.

A "fluid medium" or "fluid media" is used herein to refer to a form of matter, such as air, liquid, solid or plasma, preferably liquid, that is capable of flowing.

An "isolated cell" refers to a cell which has been separated from other components and/or cells which naturally accompany the isolated cell in a tissue or organism.

An "isolated nucleic acid" refers to a nucleic acid (or a segment or fragment thereof) which has been separated from sequences which flank it in a naturally occurring state, e.g., a RNA fragment which has been removed from the sequences which are normally adjacent to the fragment. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

"Linker" refers to one or more atoms comprising a chain connecting a nucleic acid analog to a moiety such as a peptide, nucleotide, label, modifier, stabilizing group, or the like.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

"Nucleic acid analogs" are structurally modified, polymeric analogs of DNA and RNA made by chemical synthesis from monomeric nucleotide analog units, and possessing some of the qualities and properties associated with nucleic acids. PNA and phosphorothioate oligonucleotides are examples of two of many nucleic acid analogs known in the art. "Watson/Crick base-pairing" and "Watson/Crick complementarity" refer to the pattern of specific pairs of nucleotides, and analogs thereof, that bind together through hydrogen bonds, e.g. A pairs with T and U, and G pairs with C. The act of specific base-pairing is "hybridization" or "hybridizing". A hybrid forms when two, or more, complementary strands of nucleic acids or nucleic acid analogs undergo base-pairing.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

As used herein, a "permeabilization agent" is a chemical that enables a probe access to the intracellular constituents of a cell.

A "photoreactive label" refers to a label that becomes chemically active upon irradiation of the label with light energy. Light energy useful for activating such labels includes, but is not limited to, visible light, ultraviolet (UV) light, infrared (IR) light, among others. An activated label may contain a free radical, or other highly reactive group, and may be reactive with an adjacent molecule. A photoreactive label is "incorporated into" a nucleic acid analog or a cell-penetrating peptide when the label is attached to, incorporated within, integrated into, or linked to the nucleic acid analog or the cell-penetrating peptide. This includes coupling of a label to the terminus of a nucleic acid analog or a cell-penetrating peptide as well as incorporating the label into a nucleic acid analog or a cell-penetrating peptide by including a nucleobase or amino acid analog that contains such a label.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As applied to a protein, a "fragment" of a polypeptide, protein or an antigen, is about 6 amino acids in length. More preferably, the fragment of a protein is about 8 amino acids, even more preferably, at least about 10, yet more preferably, at least about 15, even more preferably, at least about 20, yet more preferably, at least about 30, even more preferably, about 40, and more preferably, at least about 50, more preferably, at least about 60, yet more preferably, at least about 70, even more preferably, at least about 80, and more preferably, at least about 100 amino acids in length amino acids in length, and any and all integers there between.

A "genomic DNA" is a DNA strand which has a nucleotide sequence homologous with a gene as it exists in the natural host. By way of example, a fragment of a chromosome is a genomic DNA.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5' TATGGC3' share 50% homology.

In addition, when the terms "homology" or "identity" are used herein to refer to the nucleic acids and proteins, it should be construed to be applied to homology or identity at both the nucleic acid and the amino acid sequence levels.

"Conjugate" or "conjugated" refer to a covalent, ionic, or hydrophobic interaction whereby the moieties of a molecule are held together and preserved in proximity.

"Chimera" as used herein refers to an oligonucleotide including one or more nucleotide and one or more nucleotide analog units. The monomer units are linked through phosphodiester and phosphodiester analog linkages.

"Phosphodiester analog" or "internucleotide analog" refer to analogs of natural phosphodiester 3',5'-internucleotide linkages differing in their composition and/or location of attachment to a nucleotide, including but not limited to 2',5'-linkage, 3',3'-linkage, 5',5' linkage, methyl phosphonate, alkylated phosphotriester, 3'-N-phosphoramidate, and non-bridging N-substituted phosphoramidate.

The term "2'-modified RNA" means a nucleic acid analog containing one or more ribonucleotides in which a 2' position on a sugar bears a substituent replacing a hydroxyl. As an example, 2'-O-alkyl RNA comprises a nucleic acid analog containing one or more ribonucleotides in which a 2' position on a sugar consists of the moiety —OR where R is lower alkyl, such as, but not limited to, a methyl or ethyl moiety (Sproat, 1994, Protocols for Oligonucleotides and Analogs, Humana Press).

The terms "permeant" and "permeable" refer to the ability of a construct of the present invention to pass through a cellular membrane, a cell compartment membrane, or a nuclear membrane, or ascribed as characteristics of the susceptibility of membranes to have constructs pass through them (Alberts et al., 1989, Molecular Biology of the Cell, 2nd Ed., Garland Publishing, New York).

"Detection" refers to detecting, observing, or measuring a construct on the basis of the properties of a detection label.

The term "labile" refers to a bond or bonds in a molecule with the potentiality of being cleaved by reagents, enzymes, or constituents of a cell.

The term "ligand" as used herein means a molecular group that is associated with a central metal atom.

As used herein, a "solvate" of a molecule refers to a complex between the molecule and a finite number of solvent molecules. In one embodiment, the solvate is a solid isolated from solution by precipitation or crystallization. In another embodiment, the solvate is a hydrate.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In one embodiment, the invention provides compositions and methods of capturing one or more nucleic acid molecules of a cell or subcellular compartment. In one embodiment, the compositions comprise a caged molecule comprising one or more photolinkers and an antisense oligonucleotide. In certain embodiments, irradiation of the photolinker exposes the antisense oligonucleotide, thereby allowing the antisense oligonucleotide to hybridize to one or more target nucleic acid molecules.

In one embodiment, the caged molecule comprises a label or affinity tag that allows for isolation of the antisense oligonucleotide-target nucleic acid molecule complex.

In one embodiment, the caged molecule comprises a Ruthenium (Ru)-based photolinker. Ru-based photolinkers are ultrafast photolinkers that are able to release or expose the antisense nucleotide faster than about 20 ns after irradiation. Further, Ru-based photolinkers can be uniquely designed for the development of various Ru-based photolinkers having photosensitivity to varied wavelengths, thereby allowing for multiplexed or longitudinal uses. Further, Ru-based photolinkers allow for the development of circular caged compounds or hairpin caged compounds where an oligonucleotide can be conjugated at its first end to a first photolabile ligand of the Ru-based photolinker and be conjugated at its second end to a second photolabile ligand of the Ru-based photolinker.

In one embodiment, the caged molecule comprises used to prime transcription or reverse transcription of the captured nucleic acid molecule for in situ synthesis of cDNA. For example, in one embodiment, the caged molecule comprises one or more terminal deoxynucleotides to initiate cDNA synthesis. For example, in one embodiment the caged molecule comprises an antisense oligonucleotide comprising a polyU stretch and one or more terminal deoxynucleotides. In one embodiment, the caged molecule comprises a single-strand oligonucleotide comprising an antisense oligonucleotide and a terminal photoactivatable dideoxynucleotide, where activation of the terminal photoactivatable dideoxynucleotide allows for the synthesis of cDNA.

The present invention also provides methods of detecting or capturing one or more nucleic acid molecules of a cell or subcellular compartment comprising administering to the cell or subcellular compartment a caged molecule comprising a photolinker and an antisense oligonucleotide. In certain embodiments, the methods may be used to detect or capture one or more nucleic acids from live cells, including from specific cells in a living organism.

In one embodiment, the method comprises activating the caged molecule irradiating the photolinker in the cell or subcellular compartment, thereby exposing the antisense oligonucleotide. The exposed antisense oligonucleotide hybridizes to a nucleic acid molecule of the cell or cell compartment to form a complex.

In one embodiment, the method comprises isolating the complex from the cell or subcellular compartment using, for example, a label or affinity tag.

In one embodiment, the method comprises amplifying the captured nucleic acid molecule, for example using antisense RNA (aRNA) amplification. For example, in one embodiment, the method comprises administering a caged compound to a fixed sample to detect one or more nucleic acid molecules in a cell or subcellular compartment of the sample. In certain embodiments, the method comprises administering dNTPs and a reverse transcriptase to the fixed sample to synthesize cDNA from the captured nucleic acid molecule.

In certain embodiments, the method is used to capture a specific target nucleic acid, as defined by the sequence of the antisense oligonucleotide. In one embodiment, the method is used to capture all mRNA by allowing the antisense oligonucleotide to bind to the polyA tails of mRNA. In one embodiment, by utilizing a plurality of caged molecules each comprising an antisense oligonucleotide comprising a random degenerate sequence, the method is used to capture all RNA species, including but not limited to, microRNAs, lincRNAs, piwi-interacting RNAs, intron-containing RNAs, hnRNAs, poly-A+ mRNA and poly-A– mRNA.

In certain embodiments, the methods described herein may be used for the multiplexed detection of one or more nucleic acid molecules. For example, the methods may be used to detect one or more nucleic acid molecules from different cells or in longitudinal studies. In one embodiment, multiplexing comprises administering a plurality of caged molecules, where the photolinkers of the different caged molecules have different wavelength sensitivity. In one embodiment, multiplexing comprises administering a plurality of caged molecules, where the molecules comprise different index oligonucleotides.

In certain embodiments, the compositions and methods are used in living cells or tissue in a procedure known as transcriptome in vivo analysis (TIVA) and where the compounds are referred to herein as TIVA-tags.

In certain embodiments, the compositions and methods are used in fixed or frozen cells or tissue in a procedure known as transcriptome in situ analysis (TISA) and where the compounds are referred to herein as TISA-tags.

Compositions

In one embodiment, the present invention provides a caged molecule for detecting and capturing nucleic acid molecules in a cell or subcellular compartment. In one embodiment, the caged molecule comprises a photolinker and an antisense oligonucleotide having a nucleic acid sequence substantially complementary to a target nucleic acid. In certain instances, the antisense oligonucleotide is referred to herein as a capture strand or a capture region.

The target nucleic acid may be, for example, messenger RNA (mRNA), cDNA, genomic DNA, mitochondrial DNA, fragmented RNA, fragmented DNA, intronic RNA, exonic RNA, microRNA, lincRNAs, piwi-interacting RNAs, hnRNAs, poly-A+ mRNA and poly-A– mRNA, and the like.

In another embodiment of the present invention, the antisense oligonucleotide is a nucleic acid analog. In one aspect, a sugar moiety of at least one of the nucleotides of a nucleic acid analog is modified. In one embodiment, the 2'-position of a nucleoside is modified. Oligonucleotides bearing 2'-modified nucleosides have been studied as ribozymes, nuclease-resistance antisense analogs, and other cellular mechanism probes (Lamond, A., et al., Cell, 58:383-90 (1989); (Goodchild, J., Nucleic Acids Research, 20:4607-12 (1992)). Desirable features of 2'-O-alkyl-oligoribonucleosides include high chemical stability, substantial RNA- and DNA-nuclease resistance (including RNaseH), and increased thermal duplex stability (Ohtsuka, E., et al., U.S. Pat. No. 5,013,830).

In another embodiment, a fraction of the ribonucleotides of a nucleic acid analog are 2'-O-alkylribonucleotides, preferably 2'-O-methyl-ribonucleotides. Additional preferred modified ribonucleotides include 2'-O-allyl-ribonucleotides, ribonucleotides, 2'-halo-ribonucleotides, 2'-O-methoxy-ethyl-ribonucleotides, 2'-branching group-ribonucleotides, and 2'-O-branching group-ribonucleotides. In certain embodiments, the antisense oligonucleotide is 2'fluoro RNA.

As would be understood by those skilled in the art, the antisense oligonucleotide is of any suitable length necessary to bind to a target nucleotide. In certain embodiments, the antisense oligonucleotide comprising 1 or more, 2 or more, 5 or more, 10 or more, 15 or more, 20 or more, 30, or more, or 50 or more nucleotide bases. In certain embodiments, antisense oligonucleotide is divided into one, two or more parts, each separated by a photocleavable linker. Each portion of the divided antisense oligonucleotide is of any suitable length. In certain embodiments, each portion of the divided antisense oligonucleotide is a oligonucleotide comprising for more, 2 or more, 5 or more, 10 or more, 15 or more, 20 or more, 30, or more, or 50 or more nucleotide bases.

In one embodiment, the antisense oligonucleotide comprises a specific sequence that is substantially complementary to a specific region of a nucleic acid molecule of interest. For example, in certain embodiments, the antisense oligonucleotide comprises a sequence that is complementary to a nucleotide sequence is a specific target molecule. In one embodiment, the antisense oligonucleotide comprises a nucleotide sequence that is substantially complementary to a set of nucleic acids. For example, in one embodiment, the antisense oligonucleotide comprises a nucleotide sequence that is substantially complementary to the polyA tail of mRNA, thereby allowing for the capture of all mRNA in the cell or subcellular compartment. For example, in one embodiment, the antisense oligonucleotide comprises a polyT sequence. In one embodiment, the antisense oligonucleotide comprises a polyU sequence. In one embodiment, the antisense oligonucleotide comprises 2'F polyU. In some instances, the oligonucleotide comprises of 2'-OMe RNA, which serves to increase thermal stability and nuclease resistance of the molecule.

In one embodiment, the caged molecule comprises one or more photolinkers. The one or more photolinkers may be positioned in any suitable location within the caged molecule, such that photolysis of the photolinker results in the release or exposure of the antisense nucleotide. In one embodiment, the caged molecule comprises one or more nitrobenzyl (nb) photocleavable linker. Exemplary nitrobenzyl-based photocleavable linkers include those comprising 2-nitrobenzyl and o-nitrobenzyl. Exemplary nitrobenzyl-based photolinkers can be obtained from Glen Research, Corporation. In certain embodiments, the caged molecule comprises one or more Ru-based photolinkers, described elsewhere herein.

In one embodiment, the caged molecule is a circular caged molecule, wherein the first and second ends of an oligonucleotide, which comprises the antisense oligonucleotide, are each directly or indirectly conjugated to the photolinker. For example, in one embodiment, each of the first and second ends of the oligonucleotide are directly or indirectly conjugated to a photolabile ligand of the photolinker. Photolysis of the linker thus results in the linearization of the molecule thereby exposing the antisense oligonucleotide. In one embodiment, the photolinker is a Ruthenium-based photolinker, which in certain instances allows for circularization of the oligonucleotide.

In one embodiment, the caged molecule is a hairpin caged molecule comprising the antisense oligonucleotide having a first end directly or indirectly conjugated to the photolinker and a blocking oligonucleotide having a first end directly or indirectly conjugated to the photolinker. In the hairpin molecule, the antisense oligonucleotide comprises a nucleotide sequence that is substantially complementary to the blocking oligonucleotide. Photolysis of the linker results in dehybridization of the antisense oligonucleotide from the blocking oligonucleotide, thereby exposing the antisense oligonucleotide.

The blocking strand of the invention is of any suitable length to hybridize to the antisense strand. In certain embodiments, the antisense strand is an oligonucleotide comprising 1 or more, 2 or more, 5 or more, 10 or more, 15 or more, 20 or more, 30, or more, 50 or more, or 100 or more nucleotide bases. In certain embodiments, the blocking strand is divided into one, two or more parts, each separated by a photocleavable linker. Each portion of the divided blocking strand is of any suitable length. In certain embodiments, each portion of the divided blocking strand is an oligonucleotide comprising for more, 2 or more, 5 or more, 10 or more, 15 or more, 20 or more, 30, or more, 50 or more, or 100 or more nucleotide bases.

In one embodiment, the caged molecule comprises a hairpin caged molecule where the loop of the hairpin comprises the antisense oligonucleotide. In one embodiment, the hairpin caged molecule further comprises two stem-forming nucleotide regions, where the two stem-forming regions are complementary to one another such that they hybridize to form a stem. Each stem-forming region may comprise 1 or more, 2 or more, 3 or more, 5 or more, 10 or more, 15 or more, 20 or more, 30, or more, 50 or more, or 100 or more nucleotide bases. Thus, the stem of the hairpin caged molecule may be a double-stranded region of 1 or more, 2 or more, 3 or more, 5 or more, 10 or more, 15 or more, 20 or more, 30, or more, 50 or more, or 100 or more basepairs.

In one embodiment, the caged molecule comprises an index or barcode region. In one embodiment the index comprises a nucleotide sequence that uniquely identifies the molecule and any resultant amplified captured molecules. The index may comprise 1 or more, 2 or more, 3 or more, 5 or more, 10 or more, 15 or more, 20 or more, 30, or more, 50 or more, or 100 or more nucleotide bases.

In one embodiment, the caged molecule comprises a hairpin caged molecule comprising an index oligonucleotide positioned between the antisense oligonucleotide and the blocking oligonucleotide. In certain embodiments, the blocking oligonucleotide comprises one or more nucleotides that are complementary to the index oligonucleotide, such that the blocking oligonucleotide hybridizes to both the antisense oligonucleotide and to at least a portion of the index oligonucleotide. The region of the blocking oligonucleotide that is complementary to the index oligonucleotide may comprise 1 or more, 2 or more, 3 or more, 5 or more, 10 or more, 15 or more, 20 or more, 30, or more, 50 or more, or 100 or more nucleotide bases. In one embodiment, the region is complementary to the entirety of the index oligonucleotide. In another embodiment, the region is complementary to less than the entirety of the index oligonucleotide. For example, in certain embodiments, the region is complementary to 1 or more, 2 or more, 3 or more, 5 or more, 10 or more, 15 or more, 20 or more, 30, or more, 50 or more, or 100 or more of the nucleotides of the index oligonucleotide.

In certain embodiments, the index oligonucleotide comprises a nucleotide sequence that is not commonly found endogenously, thereby allowing for easy discrimination of the index from endogenous sequences. In one embodiment, the index allows for multiplexing. For example, by using a plurality of caged molecules, each comprising a unique index, it is possible to capture nucleic acid molecules from multiple cells and/or subcellular compartments. In one embodiment, the index can be used as an affinity tag, in order to purify or sort captured nucleic acid molecules based on the presence and/or identity of the index. In another embodiment, the index becomes incorporated into amplified products of the captured nucleic acid molecules, thereby allowing for sorting of amplified products based on the presence and/or identity of the index.

In another embodiment of the invention, at least two of the nucleotides making up the nucleic acid analog moiety are linked through nonstandard internucleotide linkages. By way of a non-limiting example, nonstandard internucleotide linkages include 2'-5'-linkages, inverted 3'-3' and 5'-5' linkages, methyl phosphonate, non-bridging N-substituted phosphoramidate, alkylated phosphotriester branched structures, 3'-N-phosphoramidate, peptide nucleic acid (PNA), and a non-nucleosidic polymer, among others. The term "non-nucleosidic polymer" refers to a polymer which is not a polynucleotide, e.g., polyethylene oxide, polypeptide, polyacrylamide, and polycarbohydrate.

In yet another embodiment of the present invention, at least one of the nucleotides in the nucleic acid analogs include modified nucleobases. Nucleobase modifications of the invention include, but are not limited to, C-5-alkyl pyrimidine, 2,6-diaminopurine, 2-thiopyrimidine, C-5-propyne pyrimidine, 7-deazapurine, isocytosine and isoguanine, and universal base, which shows diminished base-specific discrimination in a Watson/Crick, base-pairing hybridization interaction, e.g., 3-nitropyrrole (Nichols, R., et al., Nature, 369:492-3 (1994)) and 5-nitroindole (Loakes, D., et al., Nucleic Acids Research, 22:4039-43 (1994)).

In certain embodiments, the molecule described herein comprises a cell-penetrating domain (CPD). As will be understood by one of skill in the art, a CPD has the ability to permeate a cell membrane, or be transported across a cell membrane. In some embodiments, a CPD has the ability to permeate a nuclear membrane, or be transported across a nuclear membrane. Further, as described elsewhere herein, a CPD has the ability to carry a cargo across a cell membrane. Examples of cargo include, but are not limited to, a peptide, a nucleic acid, and a photoreactive label. Other properties of CPDs include, but are not limited to, the ability to induce endocytosis of a cargo into a cell.

In certain embodiments, the molecule does not comprise a CPD. For example, in certain embodiments, the molecule described herein can be delivered to a cell or cell compartment using other standard methodology known in the art. In certain embodiment, the molecule is delivered to a cell or cell compartment via microinjection. For example, in certain embodiments, the molecule is deliverable upon forming a nanoparticle with a liposome, micelle, or other delivery vehicle. In one embodiment, the molecule is complexed with PefFect6 (PF6), derived from the known TP10 cell-penetrating peptide (Andaloussi et al., 2011, Nucleic Acids Res, 39(9): 3972-3987).

In certain embodiments, the molecule can enter the cell without the use of a CPD. For example, in certain embodiments, the cell membrane of the cell is permeabilized, using standard reagents and procedures known in the art, which thus allows for entry of molecule. For example, in certain embodiments, the cell is fixed and thus comprises permeabilized membrane to allow for entry of the molecule into the cell.

The skilled artisan, when armed with the disclosure set forth herein, will know how to identify a CPD useful in the present invention. Briefly, a CPD useful in the present invention is one that can form a membrane-permeable construct when coupled with or non-covalently associated with a nucleic acid analog of the invention. That is, any CPD that confers the property of membrane permeability upon a CPD-nucleic acid analog construct is encompassed by the present invention. A CPD useful in the present invention can be any natural or synthetic compound found in the art. For example, a CPD useful in the present invention includes, but is not limited to, nucleic acids, peptides, proteins, small molecules, polysaccharides, organic compounds, and inorganic compounds.

However, a CPD useful in the present invention should not be limited to those disclosed herein. Rather, the skilled artisan, when armed with the present disclosure, will understand that any CPD that can transport a nucleic acid analog into a cell, known now or yet to be discovered, should be construed to be encompassed by the present invention.

In one embodiment, the CPD is folate. In another embodiment, a CPD is a cell penetrating peptide (CPP). The extensive disclosure provided in U.S. Patent Application Publication Nos. 20080199854 and 20100041025 directed to CPP are incorporated by reference as if set forth in their entirety herein. For example, the CPP can comprise an amino acid sequence that confers cell-penetrating properties upon the CPP.

The present invention also provides analogs of proteins or peptides which comprise a CPP as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:
glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "derivatives," and "variants" of the peptides of the invention (or of the DNA encoding the same) which derivatives and variants are a CPP which has been altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of a CPP of the present invention. For example, a derivative of the CPP transportan may have one or more additional amino acids added to either end of the peptide. Such biological/biochemical properties include, but are not limited to, the transport of a cargo across a cell membrane.

In one embodiment, the CPD of the molecule allows entry of the molecule into a target cell population. This target cell population can be defined by its cell type, age, metabolic activity, specific protein expression, specific receptor expression, and the like. For example, in one embodiment, the CPD is designed to target entry of the TIVA-tag specifically into cells expressing a particular receptor. In one embodiment, a TIVA-tag wherein the CPD is folate (Folate TIVA-tag) binds to a folate receptor (FR) on a cell that expresses FR on the cell surface. Other non-limiting examples of cell surface receptors in which the molecule can be directed to enter a target cell population include HER2, EGFR, transferrin receptor, chemokine receptor, asialoglycoprotein receptor, TrkA, and p75NTR. In one embodiment, the identity of the CPD directs the molecule to a target cell population. Non-limiting examples of CPDs used to direct the molecule to a target cell population include folate, EGF, transferrin, NGF, chemokines, asialoglycoprotein, riboflavin, RGD sequence, ICAM-1 antibody, LDL, cholera toxin B, Mannose-6-phosphate, nicotinic acid, or portions thereof. In some embodiments, the target cell expressing a particular cell surface receptor is a tumor cell. In some embodiments, the CPD of the molecule allows entry of the molecule into any cell type. Thus, in certain embodiments, the molecule of the invention is not targeted to any particular cell type.

In one embodiment, the molecule of the invention enters and may be activated in a subcellular compartment of a cell. Activation of the molecule in a subcellular compartment can be achieved by focusing a suitable light source with sufficient resolution to irradiate only the desired compartment of the cell. Activation of the molecule in the subcellular compartment allows isolation of polynucleotides in that compartment. Non-limiting subcellular compartments where the molecule can enter and be activated include the nucleus, nucleosome, mitochondria, chloroplast, dendrite, soma, and lysosome. In one embodiment, the CPD is directed to distinct subcellular sites. For example, in certain embodiments, the CPD can include a nuclear localization sequence to allow entry of the molecule to the nucleus. In another embodiment, the molecule enters a subcellular compartment, for example the nucleus, independent of the CPD. For example, in certain embodiments the CPD does not specifically direct the molecule into any compartment; rather the molecule enters the compartment through other mechanisms. In one embodiment, activation of the molecule in the nucleus allows hybridization and enrichment of newly transcribed mRNA transcripts.

In one embodiment, a detectable label can be incorporated on the molecule. For example, in certain embodiments, a fluorophore is incorporated on the molecule. In one embodiment, a FRET pair can be incorporated on the molecule. A FRET pair allows for monitoring the dissociation of the two strands of the molecule of the invention upon photolysis. A non-limiting example of a FRET pair is the Cy3/Cy5 fluorophores. Another example is the Cy5/Cy5.5 pair. In one embodiment, the molecule comprises a Cy3, Cy5, and a Cy5.5 fluorophore. The fluorophores may be conjugated to any region of the molecule, including, for example, to a photolinker, blocking strand, capture strand, 5'-end, or 3'-end of the molecule.

In one embodiment, a first member the FRET pair is conjugated to a first photolabile ligand of the photolinker and a second member of the FRET pair is conjugated to a second photolabile ligand of the photolinker. In one embodiment, the first member of the FRET pair is conjugated to a first end of the oligonucleotide and the second member of the FRET pair is conjugated to a second end of the oligonucleotide.

In one embodiment, the molecule comprises one or more dark quenchers. For example, in one embodiment, the molecule comprises a fluorophore and a dark quencher. In one embodiment, the molecule comprises a Cy5 fluorophore and a dark quencher.

However, the molecule is not limited to the inclusion of a fluorophore, FRET pair, or any detectable label. That is, in certain embodiments, the molecule does not comprise a detectable label for visualizing the molecule.

The present invention also includes peptides to which one or more labels have been added. A label may be used for the identification and/or purification of the peptide, or for the identification of the biological role or biological interactions of the peptide. A label useful in the present invention should have a unique or identifiable property, such as fluorescence, radioactive signal, light emission, phosphorescence, paramagnetism, and the like, which may be detectable using any spectroscopic or spectrophotometric technique known in the art. Protein labels useful in the present invention includes, but should not be limited to, biotin, dinitrophenyl, acridine, fluorescein, rhodamine, cyanine (such as Cy3 and Cy5, among others), digoxigenin, an intercalator, a minor-groove binder, a chemiluminescent precursor, selenium, cadmium, labels useful in quantum dot technology, and the like.

In one embodiment, the 2'-fluoro RNA is designed to bind the polyA tails of all mRNAs in a photolyzed cell and, after lysis, the hybridized 2'-fluoro RNA/mRNA can be isolated using standard techniques such as being affinity-purified using magnetic streptavidin beads.

In one embodiment, the molecule does not comprise a label for isolation. Rather, in certain embodiments, the antisense oligonucleotide, upon hybridization to its target, acts as a primer for use in subsequent in situ DNA polymerase-mediated cDNA production. In certain embodiments, the antisense oligonucleotide comprises a terminal DNA nucleotide (e.g., a thymine) at the 3' end, which allows for the in situ cDNA production.

The general conjugation strategy to prepare the hybrid nucleic acid molecule of the invention is to synthesize the nucleic acid analog and the other moieties separately. Reagents and automated synthesizers are commercially available for the synthesis of nucleic acid analogs. Each moiety can be further derivatized to contain reactive functionality to form a linkage. Nucleic acid analogs can be covalently coupled to peptides through any suitable bond. In one embodiment of the invention, suitable bonds include labile bonds, such as a disulfide. To form a disulfide bond in a construct between the nucleic acid analog and peptide, the two moieties may be derivatized to contain thiol groups, one of which can contain a leaving group. In another embodiment of the invention, a linkage may be formed between a nucleic acid analog and a peptide using avidin-biotin chemistry. Methods of coupling avidin and biotin to a nucleic acid analog and a peptide are well-known in the art and will not be discussed herein.

Labile linkers allow degradation of the CPD-nucleic acid analog construct, which may be important under some conditions for reduction of unwanted effects, or for optimization of the function of the nucleic acid analog. For intracellular delivery, various labile linkers can be used. By way of a non-limiting example, disulfide bridges, pH sensitive linkers and protease/nuclease substrates can be used. The intracellular milieu is highly reductive in chemical potential, due to high (mM range) concentration of gluta-thione. Thiol-containing gluthathione can exist in oxidized (disulfide) or reduced (thiol) form, the ratio of which is regulated by the enzyme glutathione-S-transferase, as well as other oxidative species. Compounds containing a disulfide bond undergo reaction with reduced gluthatione, leading to a reduced disulfide bond and oxidized gluthatione. For disulfide-containing CPD conjugates, the process has been characterized by Hällbrink et al (2001, Biochim Biophys Acta. 1515:101-9).

Ru-Based Photolinkers and Ru-TIVA

In one embodiment, caged molecule comprises one or more Ru-based photolinkers, referred to herein as Ru-TIVA tags or Ru-TISA tags. Ru-based photolinker compounds are described in the concurrently filed application of Ivan J. Dmochowski, Julianne C. Griepenburg, and Teresa L. Rapp, titled "Ruthenium-based Photolinkers and Methods of Use," PCT Application No. PCT/2015/43548, filed on Aug. 4, 2015. which application is incorporated by reference in this application.

In one embodiment, the Ru-based photolinker comprises two or more potentially photolabile ligands. In one embodiment, the two or more photolabile groups each comprise a reactive moiety, used for the attachment of the antisense oligonucleotide, fluorophore, or quencher.

The Ru-based photolinker may be synthesized using techniques well-known in the art of organic and inorganic synthesis. The starting materials and intermediates required for the synthesis may be obtained from commercial sources or synthesized according to methods known to those skilled in the art.

In one aspect, the Ru-based photolinker is a compound of formula (I), or a salt, solvate, or N-oxide thereof:

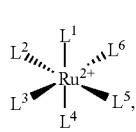

(I)

wherein in formula (I):

$L^1$, $L^2$, $L^3$, $L^4$, $L^5$, and $L^6$ are each independently a ligand, wherein at least two of $L^1$, $L^2$, $L^3$, $L^4$, $L^5$, and $L^6$ are each independently a potentially photolabile ligand having a reactive moiety.

In some embodiments, the Ru-based photolinker comprises two potentially photolabile ligands having a reactive moiety, which may be the same or different. In one embodiment, the two photolabile ligands are cis to each other. In another embodiment, the two photolabile ligands are trans to each other. In one embodiment, $L^5$ is photolabile ligand, and $L^6$ is photolabile ligand, wherein each of the photolabile ligands may be the same or different.

The photolabile ligands are capable of undergoing ligand exchange with solvent upon irradiation. In one embodiment, the irradiation is visible one-photon (1P) excitation. In another embodiment, the irradiation is near-IR two-photon (2P) excitation. Varying the photolabile ligand permits excitation and activation of compounds at different wavelengths. In a non-limiting example, compounds that are activated at different wavelengths may be useful for studying the interactions of two or more genes, proteins, or other biological systems. Any ligand that is capable of undergoing ligand exchange with solvent upon irradiation and has a reactive moiety may be used as a photolabile ligand in the invention, as would be understood by one skilled in the art. Non-limiting examples of photolabile ligands include amines, nitriles, pyridines, thioethers, pyridines, maleimides, imidazoles, triazoles, triaryl phosphines, trialkyl phosphines, and thiocyanates.

In another aspect, the photolabile ligands have a reactive moiety. The reactive moiety reacts with a reactive site on the desired biomolecule (e.g., antisense oligonucleotide), resulting in the conjugation of the Ru-based photolinker to the biomolecule. Direct $Ru^{2+}$ ligand substitution chemistry typically requires elevated temperatures (>70° C.) over several hours, which makes the conjugation reaction between the Ru-based photolinker and the biomolecule extremely difficult to perform. Instead, the Ru-based photolinkers are already installed with photolabile ligands having a reactive moiety, permitting conjugation between the Ru-based photolinker and the biomolecule under mild conditions.

Any reactive moiety that permits conjugation of the Ru-based photolinker to the biomolecule under mild conditions may be used in the invention, as would be understood by one skilled in the art. In a non-limiting example, the reactive moiety is an alkyne, and the reactive site on the biomolecule is an azide. Under mild conditions, the alkyne and azide undergo a [3+2] cyclization reaction to produce a triazole, thereby conjugating the compound to the biomolecule via the triazole moiety. It should be understood that the reactive moiety and the reactive site on the biomolecule are interchangeable, permitting an equivalent conjugation reaction wherein the functionality between the reactive moiety and the reactive site on the biomolecule have been switched. In another non-limiting example, representing the reverse of the previous example, the reactive moiety is an azide, and the reactive site on the biomolecule is an alkyne, permitting a [3+2] cyclization reaction under mild conditions to produce a triazole to conjugate the compound to the biomolecule. In another non-limiting example, the reactive moiety is an alkyl or aryl bromide or a maleimide. These reactive moieties can react with a sulfur group or an amine on the biomolecule in order to conjugate the Ru-based photolinker to the biomolecule. In addition, alkyl or aryl bromides and maleimides form covalent bonds with cysteine residues in proteins under mild conditions, resulting in a photolinker that can enforce secondary structure, then release ultrafast for protein structure studies. Other non-limiting examples of reactive moieties include carbonyl groups such as aldehydes or ketones. Aldehydes and ketones may undergo reaction with amines on the biomolecule, thereby conjugating the Ru-based photolinker to the biomolecule. Ru-based photolinker with aldehydes or ketones may be used as IR probes in 2D IR studies or femtosecond transient IR experiments, or to study the photophysical properties of the linker following conjugation or photorelease. In one embodiment, at least two photolabile ligands having a reactive moiety are selected from the group consisting of 3-ethynylpyridine, 3-(bromomethyl)pyridine, maleimide, nicotinaldehyde, 1-(4-(pyridin-3-yl)-1H-1,2,3-triazol-1-yl)ethanone, 4-pentynenitrile, and 4-aminobutyne.

In one embodiment, any of $L^1$, $L^2$, $L^3$, $L^4$, $L^5$, and $L^6$ are monodentate ligands. Non-limiting examples of monodentate ligands include nitriles, such as acetonitrile and propionitrile, sulfoxides, such as dimethylsulfoxide, amides such as dimethylformamide, ethers, such as tetrahydrofuran, water, ammonia, amines, piperidine, pyridine, pyrazine, sulfur-donor ligands such as thioethers, thiols, thioureas, or phosphorous donor ligands such as triaryl or trialkyl phosphines, or arsenic donor ligands.

In some embodiments, any of $L^1$, $L^2$, $L^3$, $L^4$, $L^5$, and $L^6$ are joined to form multidentate ligands, such as bidentate, tridentate, or tetradentate ligands. In one embodiment, any two of $L^1$, $L^2$, $L^3$, $L^4$, $L^5$, and $L^6$ are joined to form a bidentate ligand. As will be known to those of ordinary skill in the art, a bidentate ligand generally includes species which have two sites capable of binding to a metal center. For example, the bidentate ligand may comprise two heteroatoms that coordinate the metal center, or a heteroatom and an anionic carbon atom that coordinate the metal center. Examples of bidentate ligands include, but are not limited to, N,N' bidentate ligands, N,O bidentate ligands, and O,O' bidentate ligands. Non-limiting examples of N,N' bidentate ligands include diamines, such as ethylene diamine, bipyridyl such as 2,2'-bipyridyl (bpy), bridged bipyridyl, such as phenanthroline, bisquinoline, and the like. Non-limiting examples of N, O bidentate ligands include amino acids and Schiff base type groups. Non-limiting examples of O, O' bidentate ligands include dicarboxylate, 2-hydroxyacetophenone, acetylacetone type and catechol type groups. Other non-limiting examples of bidentate ligands include diimines, pyridylimines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments.

In some embodiments, the Ru-based photolinker comprises one bidentate ligand. In one embodiment, $L^1$ and $L^2$ are joined to form a bidentate ligand. In another embodiment, $L^3$ and $L^4$ are joined to form a bidentate ligand. In another embodiment, $L^5$ and $L^6$ are joined to form a bidentate ligand. In other embodiments, the Ru-based photolinker comprises two bidentate ligands. In one embodiment, the two bidentate ligands are the same. In another embodiment, the two bidentate ligands are different. In one embodiment, both $L^1$ and $L^2$ are joined to form a first bidentate ligand and $L^3$ and $L^4$ are joined to form a second bidentate ligand. In one embodiment, both the bidentate ligand formed by $L^1$ and $L^2$ and the bidentate ligand formed by $L^3$ and $L^4$ are 2,2'-bipyridyl (bpy). In another embodiment, both the bidentate ligand formed by $L^1$ and $L^2$ and the bidentate ligand formed by $L^3$ and $L^4$ are biquinoline.

In one embodiment, any three of $L^1$, $L^2$, $L^3$, $L^4$, $L^5$, and $L^6$ are joined to form a tridentate ligand. As will be known to those of ordinary skill in the art, a tridentate ligand generally includes species which have three sites capable of binding to a metal center. For example, the tridentate ligand may comprise three heteroatoms that coordinate the metal center, or a combination of heteroatom(s) and anionic carbon atom(s) that coordinate the metal center. Non-limiting examples of tridentate ligands include 2,5-diiminopyridyl ligands, tripyridyl moieties such as 2,2':6',2"-terpyridine, triimidazoyl moieties, and tris pyrazoyl moieties. In one embodiment, $L^1$, $L^2$, and $L^3$ are joined to form a tridentate ligand. In one embodiment, the tridentate ligand formed by $L^1$, $L^2$, and $L^3$ is 2,2':6',2"-terpyridine.

In one embodiment, any four of $L^1$, $L^2$, $L^3$, $L^4$, $L^5$, and $L^6$ are joined to form a tetradentate ligand. As will be known to those of ordinary skill in the art, a tetradentate ligand generally includes species which have four sites capable of binding to a metal center. For example, the tetradentate ligand may comprise four heteroatoms that coordinate the metal center, or a combination of heteroatom(s) and anionic carbon atom(s) that coordinate the metal center. A non-limiting example of a tetradentate ligand is triethylenetetramine. In one embodiment, $L^1$, $L^2$, $L^3$, and $L^4$ are joined to form a tetradentate ligand.

In one aspect of the invention, the ruthenium metal of Ru-based photolinker has an oxidation state of +2 (Ru(II)). In some embodiments, the complex contains at least one counterion Z of appropriate charge to render the overall charge of the complex neutral. Suitable counterions for cationic complexes, include but are not limited to, halide ($F^-$, $Cl^-$, $Br^-$ or $I^-$), $SO_4^{-2}$, $PF_6^-$, $BPh_4^-$, $ClO_4^-$ and $NO_3^-$. In one embodiment, Z is selected from the group consisting of $Cl^-$ and $PF_6^-$.

In some embodiments, at least one $L^1$, $L^2$, $L^3$, $L^4$, $L^5$, and $L^6$ is a fluorophore. Any fluorophore with a suitable excitation or emission wavelength may be used in the invention, as would be understood by one skilled in the art. Non-limiting examples of fluorophores include acridine orange, anthracene ring, allophycocyanin, BODIPY, cyanines, coumarin, Edans, Eosin, Erythrosin, fluorescamine, fluorescein, FAM (carboxyfluorescein), HEX (hexachlorofluorescein), JOE (6-carboxy-4',5'-dichloro-2',7'-dimethoxy-fluorescein), Oregon Green, phycocyanin, phycoerythrin, rhodamine, ROX (carboxy-X-rhodamine), TAMRA (carboxytetramethylrhodamine), TET (tetrachloro-fluorescein), Texas Red, tetramethylrhodamine, and xanthines. In one embodiment, the fluorophore has an excitation wavelength between about 550 nm and about 700 nm. In one embodiment, $L^4$ is a fluorophore. In another embodiment, $L^4$ is a fluorophore and $L^1$, $L^2$, and $L^3$ are joined to form a tridentate ligand.

In another aspect, the compound of the invention is a compound of formula (II), or a salt, solvate, or N-oxide thereof:

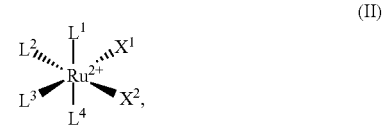

(II)

wherein in formula (II):

$L^1$, $L^2$, $L^3$, and $L^4$ are each independently a ligand; and $X^1$ and $X^2$ are each independently a potentially photolabile ligand having a reactive moiety.

In one embodiment, $X^1$ and $X^2$ are each independently selected from the group consisting of 3-ethynylpyridine, 3-(bromomethyl)pyridine, maleimide, nicotinaldehyde, 1-(4-(pyridin-3-yl)-1H-1,2,3-triazol-1-yl)ethanone, 4-pentynenitrile, and 4-aminobutyne. In one embodiment, $X^1$ and $X^2$ are each 3-ethynylpyridine.

In one embodiment, $L^1$ and $L^2$ are joined to form a first bidentate ligand and $L^3$ and $L^4$ are joined to form a second bidentate ligand. In another embodiment, the first bidentate ligand and the second bidentate ligand are selected from the group consisting of 2,2'-bipyridyl (bpy) and biquinoline. In one embodiment, the first bidentate ligand and the second bidentate ligand are 2,2'-bipyridyl (bpy).

In one embodiment, $L^1$, $L^2$, and C are joined to form a tridentate ligand. In one embodiment, the tridentate ligand is 2,2':6',2"-terpyridine.

In one embodiment, $L^1$, $L^2$, and C are joined to form a tridentate ligand, and $L^4$ is a fluorophore. In one embodiment, the tridentate ligand is 2,2':6',2"-terpyridine.

In one embodiment, the Ru-based photolinker comprises a counterion. In one embodiment, the counterion is selected from the group consisting of $Cl^-$ and $PF_6^-$.

In one embodiment, the Ru-based photolinker is selected from the group consisting of [Ru(bipyridine)$_2$(3-ethynylpyridine)$_2$]$^{2+}$, Ru(bipyridine)$_2$(3-ethynylpyridine)$_2$Cl$_2$, Ru(bipyridine)$_2$(3-ethynylpyridine)$_2$(PF$_6$)$_2$, [Ru(biquinoline)$_2$(4-pentynenitrile)$_2$]$^{2+}$, [Ru(bipyridine)$_2$(4-aminobutyne)$_2$]$^{2+}$, [Ru(bipyridine)$_2$(4-pentynenitrile)$_2$]$^{2+}$, [Ru(bipyridine)$_2$(nicotinaldehyde)$_2$]$^{2+}$, [Ru(bipyridine)$_2$(1-(4-(pyridin-3-yl)-1H-1,2,3-triazol-1-yl)ethanone)$_2$]$^{2+}$, [Ru(bipyridine)$_2$(3-(bromomethyl)pyridine)$_2$]$^{2+}$, [Ru(bipyridine)$_2$(maleimide)$_2$]$^{2+}$, a salt thereof, and any combinations thereof.

In another aspect, the Ru-based photolinker is a compound of formula (III), or a salt, solvate, or N-oxide thereof:

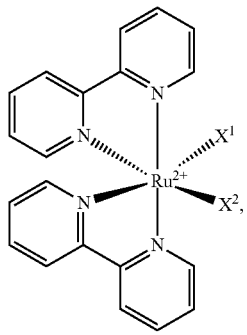

(III)

wherein in formula (III):

$X^1$ and $X^2$ are each independently a photolabile ligand having a reactive moiety.

In one embodiment, $X^1$ and $X^2$ are each independently selected from the group consisting of 3-ethynylpyridine, 3-(bromomethyl)pyridine, maleimide, nicotinaldehyde, 1-(4-(pyridin-3-yl)-1H-1,2,3-triazol-1-yl)ethanone, 4-pentynenitrile, and 4-aminobutyne. In one embodiment, $X^1$ and $X^2$ are each 3-ethynylpyridine.

In one embodiment, the Ru-based photolinker comprises a counterion. In one embodiment, the counterion is selected from the group consisting of $Cl^-$ and $PF_6^-$.

In one embodiment, the Ru-based photolinker is selected from the group consisting of [Ru(bipyridine)$_2$(3-ethynylpyridine)$_2$]$^{2+}$, Ru(bipyridine)$_2$(3-ethynylpyridine)$_2$Cl$_2$ and Ru(bipyridine)$_2$(3-ethynylpyridine)$_2$(PF$_6$)$_2$.

Preparation of the Ruthenium-Based Photolinkers

Compounds of formulae (I)-(III) may be prepared by the general schemes described herein, using the synthetic methods known by those skilled in the art. The Ru-based photolinker may possess one or more stereocenters, and each stereocenter may exist independently in either the R or S configuration. In one embodiment, Ru-based photolinkers described herein are present in optically active or racemic forms. It is to be understood that the Ru-based photolinkers described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomers is utilized as the therapeutic compound described herein. In another embodiment, Ru-based photolinkers described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water and ethanol. In another embodiment, the compounds described herein exist in unsolvated form.

In one embodiment, the Ru-based photolinkers may exist as tautomers. All tautomers are included within the scope of the Ru-based photolinker presented herein.

Ru-based photolinkers described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. Isotopically-labeled compounds are prepared by any suitable method or by processes using an appropriate isotopically-labeled reagent in place of the non-labeled reagent otherwise employed.

In one embodiment, the Ru-based photolinkers described herein are labeled by other means, including, but not limited to, the use of chromophores or fluorescent moieties, bioluminescent labels, or chemiluminescent labels.

The Ru-based photolinkers described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000,2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Ru-based photolinkers described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

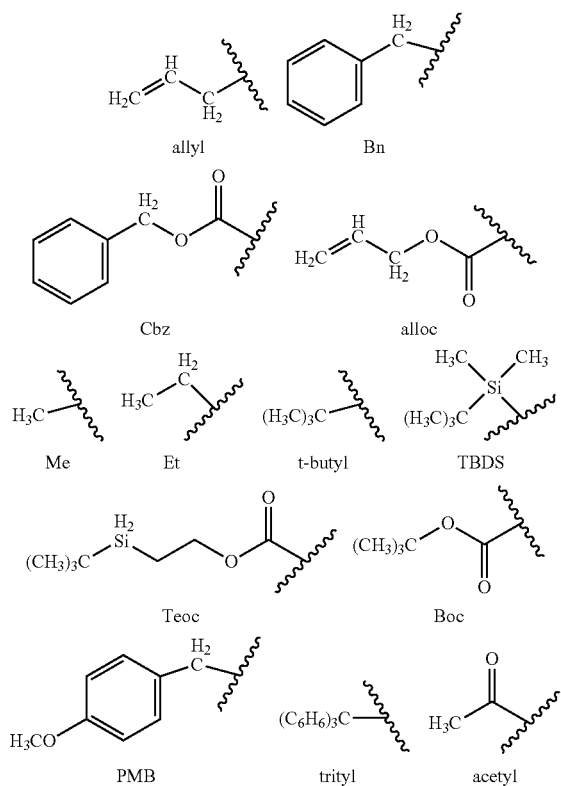

-continued

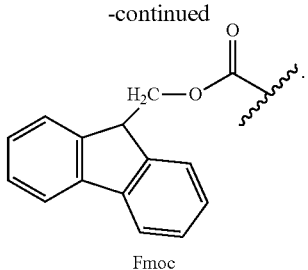

Fmoc

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In certain embodiments the inclusion of Ru-based photolinkers in the caged molecule allows for ultrafast uncaging of antisense oligonucleotide. Ru-based photolinkers may be conjugated to one or more oligonucleotides of the caged molecule using any methodology known in the art, including for example "click chemistry." In certain embodiments, the oligonucleotide of the caged molecule comprises one or more modified nucleotides, such an amino-dT (dT-amine), which can be used to conjugate the oligonucleotide to the Ru-based photolinker or to a flurophore. In one embodiment, the modified nucleotides may be positioned at the terminal ends of the oligonucleotide. In one embodiment, the modified nucleotides may be positioned at an internal position within the oligonucleotide.

In one embodiment, the present invention provides a composition comprising a plurality of different Ru-TIVA-tags, as described herein. As described elsewhere herein, the different ruthenium-based photolinkers display differential photosensitivity. Thus, in one embodiment, the plurality of different Ru-TIVA-tags may comprise Ru-TIVA-tags having different ruthenium-based photolinkers, thus allowing for differential activation of one or more types of Ru-TIVA-tags of the composition, thereby allowing for multiplexed detection of various species of interest or longitudinal detection over a time period.

In one embodiment, the plurality of Ru-TIVA-tags each comprise a random antisense oligonucleotide. In certain instances, the Ru-photolinkers in the caged molecule allow for the generation of circular caged molecules and hairpin caged molecules where the antisense oligonucleotide need not be blocked by a blocking oligonucleotide. Thus, in contrast to prior hairpin caged molecules, specific design of complementary antisense oligonucleotides and blocking oligonucleotides is not needed. Therefore, Ru-TIVA tags can be generated having a random or degenerate antisense oligonucleotide, which may be used in TIVA-tot or TIVA-nuc applications to capture all types of RNA molecules, instead of just polyA+ RNA. As described elsewhere herein, a particular advantage of the Ru-TIVA-tag is that the a blocking strand is often not necessary to be hybridized to the antisense capture strand in the caged conformation. Thus, Ru-TIVA-tags may be generated with antisense oligonucleotides having random nucleotide sequences, without the need for a corresponding blocking strand. Thus, a composition comprising a large number of Ru-TIVA-tags, each having a random antisense oligonucleotide, allows for the capture of every nucleic acid species present in the cell or cell compartment in which the plurality of Ru-TIVA-tags are administered and activated (TIVA-tot). For example, in certain embodiments, the use of the plurality of Ru-TIVA-tags, each comprising random antisense oligonucleotides isolates all RNA, including, but not limited to microRNAs, lincRNAs, piwi-interacting RNAs, intron-containing RNAs, hnRNAs, poly-A+ mRNA and poly-A− mRNA.

TISA-Tags

In one embodiment, the compositions of the invention comprise a caged molecule comprising one or more photolinkers, an antisense oligonucleotide, and one or more terminal deoxynucleotides to prime cDNA synthesis.

In one embodiment, the caged molecule comprises one or more deoxynucleotides attached to the antisense oligonucleotide. For example, in one embodiment, the one or more deoxynucleotides are positioned on the 3'-end of the antisense oligonucleotide. The one or more deoxynucleotides may be a dA, dT, dG, dC, or combinations thereof. The deoxynucleotides may comprise a mono-, di-, or tri-phosphate group. In certain embodiments, the one or more deoxynucleotides comprise a modified base, modified ribose, modified phosphate, and/or modified linkages as described elsewhere herein. In certain embodiments, one or more deoxynucleotides participate in hybridization with the blocking oligonucleotide. In one embodiment, one or more deoxynucleotides participate in hybridization with the target nucleic acid molecule.

The one or more deoxynucleotides are used to prime cDNA synthesis from the captured nucleic acid molecule. For example, in one embodiment, reverse transcriptase is used to synthesize cDNA from a captured RNA molecule. The synthesized cDNA may be isolated or amplified as described elsewhere herein. For example, in one embodiment, the synthesized cDNA is further processed to incorporate a promoter region for in vitro transcription.

In certain embodiments, the caged molecule is a hairpin caged molecule comprising an antisense oligonucleotide and a blocking oligonucleotide, where photolysis of the photolinker releases the blocking oligonucleotide, thereby exposing the antisense oligonucleotide to bind to a target nucleic acid molecule.

In certain embodiments, the caged molecule is a circular caged molecule, wherein both ends of the oligonucleotide are conjugated to the photolinker. In another embodiment, the caged molecule comprises a hairpin caged molecule wherein the loop of the hairpin comprises the antisense oligonucleotide. For example, in certain embodiments the TISA-tag may comprise a Ru-based photolinker, as described elsewhere herein.

In one embodiment, the antisense oligonucleotide comprises a specific sequence that is substantially complementary to a specific region of a nucleic acid molecule of interest. For example, in certain embodiments, the antisense oligonucleotide comprises a sequence that is complementary to a nucleotide sequence is a specific target molecule. In one embodiment, the antisense oligonucleotide comprises a nucleotide sequence that is substantially complementary to a set of nucleic acids. For example, in one embodiment, the antisense oligonucleotide comprises a nucleotide sequence that is substantially complementary to the polyA tail of mRNA, thereby allowing for the capture of all mRNA in the cell or subcellular compartment. For example, in one embodiment, the antisense oligonucleotide comprises a polyT sequence. In one embodiment, the antisense oligonucleotide comprises a polyU sequence.

In certain embodiments, the antisense oligonucleotide comprises a random or degenerate sequence, which may be used, for example, in methods to detect all RNA species in a sample, instead of just poly+ RNA.

Caged molecules comprising the one or more deoxynucleotides for cDNA synthesis are particularly useful for detection of target nucleic acid molecules in fixed samples. For example, in certain instances, prior caged molecules are unable to capture nucleic acid molecules from fixed samples, because the crosslinking of fixed samples make it difficult to isolate the molecule-target complex. Caged molecules described herein for use in fixed samples are referred to herein as TISA-tags.

However, in certain instances, the caged molecules having the one or more deoxynucleotides for cDNA synthesis maybe used in live cells, where they may be referred to as self-priming TIVA-tags or TIVA-extend tags. In certain embodiments, when used in live cells, the molecules having the one or more deoxynucleotides for cDNA synthesis further comprise a CPD as described elsewhere herein.

In one embodiment, the caged molecule comprises a hybrid double-stranded nucleic acid molecule comprising a capture oligonucleotide and a blocking oligonucleotide (FIG. 38, referred to herein as "TISA-bandaid"). In one embodiment, the capture oligonucleotide comprises an antisense oligonucleotide comprising a sequence substantially complementary to a target nucleic acid molecule. In one embodiment, the antisense oligonucleotide comprises a polyT or polyU strand for targeting a polyA target, but having one or more internal mismatches (e.g. C, G, or A) that do not undergo basepairing with the polyA target. In one embodiment, the blocking oligonucleotide comprises a nucleotide sequence complementary to the antisense oligonucleotide of the capture strand and one or more photolinkers. The one or more mismatches of the antisense oligonucleotide ensure for proper alignment of the hybridization of blocking oligonucleotide to the antisense oligonucleotide with minimal concession in target hybridization. In one embodiment, the capture strand further comprises a promoter region. In one embodiment, the capture strand further comprises an index. Photolysis of the photolinkers allows for the antisense oligonucleotide to bind to its target and to prime cDNA synthesis which, in certain embodiments, generates a double-stranded cDNA molecule comprising a promoter and index.

In one embodiment, the caged molecule comprises a single-stand molecule comprising an antisense oligonucleotide and a terminal photoactivatable dideoxynucleotide (FIG. 39, referred to herein as Photo-activated chain terminator TISA". The antisense oligonucleotide is complementary to a target nucleic acid molecule. For example, in one embodiment, the antisense oligonucleotide comprises a polyU or polyT stretch to target polyA+ RNA. In another embodiment, the antisense oligonucleotide may be complementary to a nucleotide sequence of a specific target. In another embodiment, the antisense oligonucleotide may comprise a random or degenerate sequence.

The photoactivatable dideoxynucleotide blocks strand synthesis until photoactivated. In one embodiment, where the antisense oligonucleotide comprises polyT stretch, the photoactivatable dideoxynucleotide is one of ddATP, ddCTP, or ddGTP, such that the polyT stretch is more likely to hybridize to the terminal polyA tail of the target nucleic acid molecule. In one embodiment, the single-stranded caged molecule comprises a promoter region. In one embodiment, the single-stranded caged molecule comprises an index. Photoactivation of the photoactivatable dideoxynucleotide converts the dideoxynucleoitde into a deoxynucleotide, which thus allows for cDNA synthesis from the captured nucleic acid molecule. In certain embodiments, the resultant cDNA comprises a promoter and index oligonucleotide.

Methods

The present invention also provides methods of identifying nucleic acid molecules in an individual live cell. The method includes the steps of providing a caged molecule of the invention in a caged form into a cell or cell compartment, activating the molecule in the cell or cell compartment under conditions suitable for binding of the antisense oligonucleotide to cellular nucleic acid to form a complex.

In one embodiment, the caged molecule is administered to the cell via the action of a CPD of the molecule. However, the method is not limited to the use of a CPD. Rather, the method encompasses any method known in the art to deliver the molecule into a cell or cell compartment of interest. For example, in certain embodiments, the molecule is deliverable upon forming a nanoparticle with a lipid, liposome, micelle, or other delivery vehicle. In one embodiment, the molecule is noncovalently complexed with PepFect6 (PF6), derived from the known TP10 cell-penetrating peptide (Andaloussi et al., 2011, Nucleic Acids Res, 39(9): 3972-3987). In one embodiment, the molecule is microinjected into a cell or tissue of interest.

The recipient cell for molecule of the invention may be at least one of any type of cell. A recipient cell may be a eukaryotic cell or a prokaryotic cell. When the cell is a eukaryotic cell, the cell is preferably a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell, the cell is a bacterial cell. A recipient cell may be a differentiated cell and/or a non-dividing cell. The cell may also be a progenitor cell or a stem cell. Preferably, the recipient cell is a tissue-specific cell, more preferably a mammalian tissue-specific cell and more preferably still, a human tissue-specific cell. Non-limiting examples of cells suitable as a recipient cell include epithelial cells, neurons, fibroblasts, embryonic fibroblasts, keratinocytes, adult stem cells, embryonic stem cells, and cardiomyocytes.

The method of the invention may be performed on a cell comprising a cellular process. Such a cellular process includes, but is not limited to, a dendrite, an axon, a microvilli, a cilia, a stereocilia, a process, an astrocytic process, and the like.

The present invention further comprises methods for introducing the molecule of the invention into a live slice of tissue or a live animal. Methods for sustaining the cellular processes in the cells comprising a live slice of tissue are known in the art. As a non-limiting example, live slices can be refrigerated and perfused with natural or artificial fluids, such as artificial spinal fluid, artificial central nervous system fluid, and buffers disclosed elsewhere herein. Methods for the manipulation of live slice cultures are described in, for example, Roelandse, et al. (2004, J. Neuroscience, 24: 7843-7847); and Chen, et al. (2005, Magn. Reson. Med. 53: 69-75).

In certain embodiments, the photolinker is activated by use of any suitable light source capable of delivering light at the wavelength needed to activate the particular linker. For example, in certain embodiments, the light source is a white light source. In one embodiment, the light source is a white light source with a colored filter. In one embodiment, the light source is a UV-light box. In one embodiment, the light is light from a laser source. In certain embodiments, the light is UV-light, visible light, near infrared light, or infrared light. In one embodiment, the light used to cleave the linker has a wavelength of about 350 nm to about 1500 nm.

In one embodiment, the photolinker is designed to be cleaved when exposed to light of a particular wavelength, or range of wavelength. Once the photolinker is cleaved, the antisense oligonucleotide of the molecule of the invention is available for binding to target cellular nucleic acid. For example, following photolysis, the 2'-fluoro antisense oligonucleotide containing poly T's or poly U's is available for binding to cellular poly A tails.

In one embodiment, activation of the caged molecule of the invention in a cell or cell compartment is accomplished by irradiation of the ruthenium-based photolinker to cleave one or more of the photolabile ligands of the photolinker. For example, exposure to light induces cleavage of one or more of the photolabile ligands of the ruthenium-based photolinker contained in the molecule of the invention. In one embodiment, the method comprises cleaving a single photolabile ligand of a ruthenium-based photolinker of a circular caged molecule, thereby linearizing the molecule and exposing the antisense oligonucleotide.

Isolation of Captured Species

In one embodiment, the method comprises isolating the hybridized complex. In one embodiment of the invention, the method includes lysing the cell containing the hybridized complex to form a cell lysate, contacting the cell lysate with a solid support under conditions suitable to allow the hybridized complex to bind to the solid support, and separating the complex from the lysate. In one aspect, the isolating step includes lysing the cell containing the hybridized complex to form a cell lysate, and contacting the cell lysate with a solid support comprising a binding moiety specific for a tag or label of the molecule of the invention. For example, if the tag is biotin, a binding moiety specific for the tag would be streptavidin beads. However, the invention should not be limited to biotin as the tag and streptavidin as the binding moiety thereof. Rather, the invention encompasses the used of any tag and corresponding binding moiety for purposes of isolating the hybridized complex from a cell or cell lysate.

In Situ Analysis

In one embodiment, the complex is not isolated. Rather, in certain instances, the antisense oligonucleotide, upon hybridization to its target, acts as a primer for use in subsequent in situ cDNA production. In certain embodiments, the antisense oligonucleotide comprises one or more terminal deoxynucleotides at the 3' end, which allows for the in situ cDNA production.

In certain embodiments, the in situ cDNA synthesis from TISA-tags are performed in fixed tissue samples. The fixed tissue samples may comprise any type of fixed sample, including fixed biopsy samples, fixed samples from tissue banks, fixed pathological tissue, fixed healthy tissue, and the like. The samples may be fixed using any known methodology. In some embodiments, the fixed tissue samples are fixed by a method of fixation selected from the group consisting of formaldehyde, Bouin's, xylene, ethanol and methanol. In certain embodiments, the fixed tissue sample is crosslinked.

Any tissue sample from a subject may be used in the method of the invention. Examples of tissue that may be used include, but are not limited to, breast, prostate, ovary, colon, lung, endometrium, stomach, salivary gland and pancreas. The tissue sample can be obtained by a variety of procedures including, but not limited to surgical excision, aspiration or biopsy. The tissue may be embedded in paraffin or frozen.

In one embodiment, the tissue sample is fixed. The tissue sample may be fixed (i.e. preserved) by any conventional methodology. See e.g., "Manual of Histological Staining Method of the Armed Forces Institute of Pathology," 3rd edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C. One of skill in the art will appreciate that the choice of a fixative may be determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample.

Generally, the tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology See e.g., "Manual of Histological Staining Method of the Armed Forces Institute of Pathology", supra. Examples of paraffin that may be used include, but are not limited to, PARAPLAST®, Broloid, and Tissuemay. Once the tissue sample is embedded, the sample may be sectioned by a microtome or the like. See e.g., "Manual of Histological Staining Method of the Armed Forces Institute of Pathology", supra. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

Fixation by cross-linking is a method commonly used for fluorescence microscopy. It involves treating specimens with reagents that penetrate into the cells and tissues and form covalent cross-links between intracellular components. The most commonly used cross-linking agents are aldehydes, which form covalent bonds between adjacent amine-containing groups through Schiff acid-base reaction. These bonds form both inter- and intra-molecularly and are, therefore, very effective fixatives for proteins and nucleic acids. The two most frequently used aldehydes are formaldehyde and glutaraldehyde. Both fixatives have advantages and disadvantages, which will be discussed below. Other aldehydes, such as acrolein, have been used historically, but do not preserve samples as well.

Glutaraldehyde is a four carbon molecule terminated at both ends by aldehyde groups. It is an extremely efficient fixative, and is widely used in light and electron microscopy because of its efficacy in preserving cellular structure. In some instances, however, other fixatives may be preferred. For instance, the comparatively high molecular weight of glutaraldehyde limits its ability to diffuse into thick specimens, such as tissue sections or embryos. In addition, as a tissue is cross-linked by the fixative, glutaraldehyde's ability to penetrate over time diminishes. For such samples, formaldehyde may be a better option. Second, free aldehyde groups fluoresce efficiently at the same wavelengths as many of the fluorescent probes employed by biologists. As glutaraldehyde possesses two functional groups per molecule, background autofluorescence may be a significant problem in fixed tissues, effectively lowering the probe's signal to noise. This problem may be circumvented by using relatively low concentrations of glutaraldehyde (i.e. less than 1%). Unreacted aldehydes may also be quenched by treating fixed samples with reducing agents, such as sodium borohydride, to reduce free aldehyde groups to alcohols, or by reacting them with exogenous amine-containing reagents, such as ammonium chloride or glycine. In a preferred embodiment of the present invention, the fixed tissue is treated with sodium borohydride to quench autofluorescence.

Formaldehyde is probably the most commonly used cross-linking fixative for biological samples. It has a single aldehyde-containing carbon and exists as a gas. Formaldehyde does not cross-link as effectively as glutaraldehyde, and for this reason is rarely used by-itself for electron microscopy. However, its small molecular weight allows it to penetrate cells and tissues rapidly, making it a choice fixative for thicker samples and autofluorescence of unreacted aldehyde groups is not usually a problem.

The in situ synthesis of cDNA from a captured nucleic acid molecule, by way of the present method, allows for the analysis of nucleic acid species in cross-linked fixed tissue. In certain instances, the crosslinking of fixed tissue renders the analysis using previously described caged molecule probes difficult, as they require the isolation of the captured target.

If so desired, the tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De® (CMS, Houston, Tex.) may be used. Advantageously, however, the method of the invention does not require deparaffinization. Thus, archival samples are preserved when subjected to the method of the invention, and may conceivably be re-used.

In certain embodiments, the fixed tissue sample is stained. For example, in certain embodiments, the fixed tissue sample is immunostained using traditional immunohistochemistry methodology to detect and visualize one or more markers (e.g, proteins, peptides, etc.) of the tissue.

For example, in one embodiment, the fixed tissue sample may be immunostained for cell type-specific markers to identify different cell types within the same fixed tissue sample. For example, in one embodiment, the fixed tissue sample may be a pancreatic sample, and the sample may be immunostained to differentiate between alpha cells and beta cells. In another example, the fixed tissue sample may be a brain sample, and the sample may be immunostained to differentiate between neurons and glia. In certain embodiments, the sample may be immunostained to detect one or more pathological markers indicative of cell death, apoptosis, necrosis, tumor, and the like. For example, in certain embodiments, the fixed sample may be immunostained to detect tumor cells within the sample.

In certain embodiments, the sample may be stained with one or more markers to identify different cellular compartments. For example, in one embodiment, the sample may be stained to differentiate between the axon and soma of a neuron. In certain embodiments, the sample may be stained to identify compartments such as the nucleus, mitochondria, lysosome, endoplasmic reticulum, Golgi body, and the like.

Additional histological stains include, but are not limited to, Hematoxylin, Eosin, Toluidine blue, Masson's trichome stain, Mallory's trichome stain, Weigert's elastic stain, Heidenhain's AZAN trichome stain, silver stain, Wright's stain, Orecin stain, and Periodic acid-Schiff stain. Another exemplary staining methodology includes the Nissl staining method.

In certain instances, stained fixed tissue samples allow for specific uncaging of the caged molecule in one or more cells of interest. For example, in certain embodiments, the caged molecule can be uncaged specifically in cells that stain positive for a marker of interest. In another embodiment, the caged molecule can be uncaged specifically in cells that stain negative for the marker of interest. This allows for the present method to differentially analyse target nucleic acids among different cell types within the same tissue, or among healthy versus diseased cells within the same tissue.

In certain embodiments, the stained fixed tissue samples allows for specific uncaging of the caged molecule in a specific cellular compartment. For example, in certain embodiments, the caged molecule can be uncaged specifically in cellular compartments that stain positive for a marker of interest. In another embodiment, the caged molecule can be uncaged specifically in cellular compartments that stain negative for the marker of interest. This allows for the present method to differentially analyse target nucleic acids among different cellular compartments within a single cell.

In certain embodiments, the fixed tissue sample is exposed to a permeabilization agent to allow for entry of the caged molecule into the cell. Exemplary permeabilization agents include, but are not limited to Triton X-100, Tween-20, saponin, SDS, NP40, streptolysin O, proteinase K, pronase and triethanolamine, and organic solvents, such as methanol and acetone.

In one embodiment, the captured nucleic acid molecule is amplified, for example using standard methodology such as antisense RNA (aRNA) amplification and in vitro transcription. In one embodiment, the method comprises administering a DNA polymerase and dNTPs to the sample such that reverse transcriptase is able to use the one or more deoxynucleotides of the bound molecule to prime cDNA synthesis from the captured RNA. Any suitable type or isoform of DNA polymerase can be used to synthesize the cDNA from the captured RNA. In one embodiment the DNA polymerase is reverse transcriptase.

In one embodiment, the cDNA of the resultant cDNA-RNA hybrid molecule is dehybridized. For example, in one embodiment, the cDNA-RNA hybrid molecule is heat denatured to release the cDNA. In another embodiment, the RNA of the sample is hydrolyzed, for example by alkaline hydrolysis by application of NaOH to the sample.

In one embodiment, the released cDNA can be detected by affinity purification, using an affinity column specific for an affinity tag present on the cDNA molecule. In certain embodiments, the released cDNA is collected from the sample and second strand cDNA is synthesized from the released cDNA in a reaction vessel. For example, in certain embodiments, random primers and one or more DNA polymerases are added to the vessel to generate the second strand cDNA.

In one embodiment, the resultant double-stranded cDNA is further processed to incorporate a promoter site. For example, in one embodiment, the double-stranded cDNA is denatured, and an oligonucleotide comprising a nucleotide sequence complementary to a cDNA strand is administered to the reaction vessel. In one embodiment the oligonucleotide comprises a polyT stretch to hybridize to the polyA of the cDNA. In one embodiment the oligonucleotide comprises the index nucleotide sequence that binds to the antisense of the index nucleotide sequence present in the cDNA, if a TISA-tag comprising an index was used. The index of the oligonucleotide ensures that endogenously primed RNA from non-TISA-targeted cells are not amplified, which would otherwise contaminate data from the TISA-targeted cell(s). In certain instances, the oligonucleotide further comprises a spacer region between the promoter and the index region, to ensure efficient transcription of the index. In certain instances, the oligonucleotide further comprises a plurality of bases 5' to the promoter region, which ensures efficient binding of the RNA polymerase to the promoter region. In one embodiment, the method comprises administering one or more polymerases to the vessel, thereby synthesizing a double-stranded cDNA molecule incorporating the promoter. The resultant double-stranded cDNA is then amplified using in vitro transcription, where RNA polymerase is able to bind to the promoter region and transcribe an RNA molecule comprising the antisense RNA of the captured RNA and the index, thus allowing for in situ transcription from the cDNA strand. The RNA may be further amplified using the previously described oligonucleotide in subsequent rounds of aRNA amplification as necessary to generate sufficient material for various detection methods (e.g., PCR, RNA sequencing, etc.).

In certain embodiments, for example where the caged molecule comprises an index oligonucleotide and/or promoter (e.g., TISA-bandaid and Photo-activated chain terminator TISA), the promoter and/or index are incorporated into the double-stranded cDNA molecule upon first-strand and second-strand synthesis.

In certain embodiments, the synthesis of cDNA and subsequent rounds of amplification may be performed using robotic instrumentation known in the art, including but not limited to, a liquid handling robot.

Methods of Multiplexing

In one embodiment, the method comprises a multiplexed detection of cellular nucleic acid species by administering to a cell or tissue sample, a plurality of caged molecules. For example, in certain embodiments, the method allows for multiplexed detection in longitudinal studies of detecting nucleic acid species over a time course in the same cell or subcellular compartment. In one embodiment, the method allows for multiplexed detection of nucleic acid species in different subcellular compartments of a cell. In one embodiment, the method allows for multiplexed detection of nucleic acid species in different cells of a tissue.

In one embodiment, the method comprises using a plurality of Ru-TIVA tags, where each Ru-TIVA tag comprise ruthenium-based photolinkers having different sensitivities to different wavelengths, thereby allowing selective activation of particular caged molecule species. The ruthenium-based photolinkers described herein are easily tuned to be reactive to varying wavelengths, thereby allowing for multiplexed detection.

In one embodiment, the method comprises using a plurality of TISA tags, where each TISA tag comprise a unique index oligonucleotide. For example, in one embodiment, the method comprises the sequential administration and uncaging of a plurality of TISA-tags. For example, in one embodiment, the method comprises administering a first TISA tag having a first index to a fixed sample, and uncaging the TISA-tag in a first cell or subcellular compartment, thereby capturing a target nucleic acid molecule in the first cell or subcellular compartment. In one embodiment, the method comprises administering a second TISA tag having a second index to a fixed sample, and uncaging the TISA-tag in a second cell or subcellular compartment, thereby capturing a target nucleic acid molecule in the second cell or subcellular compartment. In certain embodiments, the steps are repeated for a third, fourth, fifth, or more TISA-tag if desired. In certain embodiments, the first and second cell are distinguished by the presence or absence of a marker, as detected by histological or immunohistological staining, as described elsewhere herein.

In one embodiment, the method comprises administering reverse transcriptase and dNTPs to the sample, thereby synthesizing cDNA from the target nucleic acid molecule captured by the first TISA-tag and second TISA-tag, where the synthesized cDNAs each incorporate the first and second indices. Subsequent isolation or amplification may be carried out as appropriate, and the eventual transcripts may be sorted by the presence and identity of the index.

TIVA-Tot

In one embodiment, the invention provides a method for capturing all of the RNA species in a cell or cell compartment (sometimes referred to herein as TIVA-tot). As discussed elsewhere herein, a particular advantage of the circular Ru-TIVA-tag is that a blocking strand is often not necessary to be hybridized to the antisense capture strand in the caged conformation. Thus, Ru-TIVA-tags may be generated with antisense oligonucleotides having random nucleotide sequences, without the need for a corresponding blocking strand. Thus, a plurality of Ru-TIVA-tags may be generated, each having an antisense oligonucleotide having a random nucleotide sequence. Production of a large number of these Ru-TIVA-tags comprising random antisense oligonucleotides thereby allows for the capture of every nucleic acid species present in the cell or cell compartment in which the plurality of Ru-TIVA-tags are administered and activated. For example, in certain embodiments, the use of the plurality of Ru-TIVA-tags, each comprising random antisense oligonucleotides isolates all RNA, including, but not limited to microRNAs, lincRNAs, piwi-interacting RNAs, intron-containing RNAs, hnRNAs, poly-A+ mRNA and poly-A− mRNA.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Optimizing TIVA-Tags for Neuron Uptake, Stability, and RNA Harvesting As the first non-invasive method for cellular mRNA capture, TIVA shows extreme promise for extending the power of RNAseq to enable systems neurobiology. Described herein are studies that elaborate the TIVA approach to improve cell uptake and RNA capture yields, achieve much greater depth penetration and cell selectivity for RNA harvesting in brain slices by developing ruthenium caging moieties suitable for 2-photon (2-P) excitation, and develop multiplexed TIVA caging strategies to allow longitudinal studies of gene expression, pre- and post-stimulus. The inorganic compositions and methods for caging TIVA described herein will apply to caging oligonucleotides for a wide range of biological applications.

As described herein, TIVA allows for the isolation and analysis of full-length coding RNAs, which thereby allows for observation of single-cell variability across a wide range of population expression levels. It is now recognized that one source of variability originates from bimodal splicing patterns that occur for genes whose isoforms have distinct functional consequences (Shalek et al., 2013, Nature, 498: 236-40). Notably, splicing differences in regulatory genes should enhance expression diversity.

It will also be possible to assay for many non-coding RNAs using the TIVA procedure. In a recent paper, 1,600 large intervening noncoding RNAs (lincRNAs) were identified by microarray analysis, each possessing a polyA tail (Guttman et al., 2009, Nature, 458: 223-7). Thus, although it is well recognized that many regulatory RNA molecules, such as short-interfering RNA (siRNA), lack a polyA tail, many longer, noncoding RNAs do possess a polyA tail and are therefore amenable to capture by the same TIVA approach. Many lincRNAs are hypothesized to be important in transcriptional control, and thus will be important to study in addition to mRNA. For example, lincRNA has recently been TIVA-captured from single neurons in brain slices using RNAseq. This highlights the broad applicability of TIVA-enhanced RNAseq technology to advancing our understanding of RNA biology in living specimens.

From a conceptual standpoint, this work explores a hypothesis regarding the fundamental role of neuron microenvironment in controlling transcriptional variability. The findings of this analysis will demonstrably improve the ability to link transcriptomics with cell function.

The development of caged oligonucleotides whose affinity for target mRNA is turned 'on' or 'off' upon photolysis of just one or two photoactive moieties has recently been described (Dmochowski et al., 2007, J Biotechniques, 43: 161; Tang et al., 2006, Angew Chem Int Ed, 45: 3523; Richards et al., 2008, J Bioorg Med Chem Lett, 18: 6255; Tang et al., 2005, Org Lett, 7: 279; Tang et al., 2007, Mol Biosys, 3: 100; Tang et al., 2007, J Am Chem Soc, 129: 11000; Tang et al, 2005, Bioorg Med Chem Lett, 15: 5303; Tang et al., 2008, Nucl Acids Res, 36: 559; Richards et al., 2010 ChemBioChem, 11: 320; Ruble et al., 2012, Inorg Chim Acta, 380: 386; Gripenburg et al., 2013, Bioorg Med Chem Lett, 21(20): 6198). This work has provided thermodynamic principles and synthetic methods for the design and creation of conditionally caged oligonucleotides. In other experiments, nucleic acid-cell penetrating peptide (CPP) conjugates were engineered to harvest RNA binding proteins from live cells (Zielinski et al., J. Proc. Natl. Acad. Sci., 2006, 103, 1557; Zeng et al., J. Nat. Protoc. 2006, 1, 920). Building on this foundation, a TIVA prototype now provides the first noninvasive method for harvesting mRNA from single cells in complex, living brain tissues (Lovatt et al., 2013, Nat Methods, 11(2): 190). As described herein, TIVA is extended in ways that will revolutionize transcriptomics research, particularly to improve single-cell resolution in the z-dimension using 2-photon uncaging. Further, multiplexing capabilities and an affinity-tag-based time-stamp of all TIVA-harvested RNA is described, as required for longitudinal studies. The chemistries required to achieve these breakthroughs were developed and are now incredibly well poised to advance the field of neurobiology.

While much is known about the transcriptome of isolated cells (e.g., cultured neurons), it has been significantly more challenging to assess the mRNA complement from neurons in their native microenvironment, as will be critical for understanding brain function. One example of a TIVA-tag employs two 2-nitrobenzyl (nb) photocleavable linkers (PL, Glen Research) inserted as phosphoramidites during solid-phase synthesis, which are optimally cleaved at 365 nm, but can also be uncaged with 405 nm. The chemistry of the 2-nitrobenzyl moiety and derivatives has been widely investigated (McCray et al., 1980, Proc Natl Acad Sci USA, 77: 7237; Il'ichv et al., 2004, J Am Chem Soc, 126: 4581; Walker et al, 1988; J am Chem Soc, 110: 7170; Corrie et al., 2003, J Am Chem Soc, 125: 8546). These nb-TIVA-tags are useful, for example, for isolating mRNA from cultured neurons and superficial regions in brain slices, in order to assess transcriptome variability. As such, nb-TIVA allows the optimization of key features of the TIVA design, via synthesis, characterization, and testing in neurons.

The Cy3-Cy5 FRET reporter works in cells and tissues to report on TIVA-tag stability and photocleavage. TIVA-tags tested to date are non-toxic to neurons when purified by analytical HPLC, followed by NAPS column and Amicon size-exclusion/centrifugation to remove solvents and metal salts.

One of the key technical breakthroughs described herein is the ability to perform longitudinal studies of transcriptome changes. This requires: i) very efficient, light-activated capture of mRNA within a single cell or multiple cells of interest, and, ii) several, distinct affinity tags for cleanly harvesting all mRNA captured in the cell at each time point. Both TIVA-tag features are described herein.

Optimizing Cell Uptake

The first step to improving RNA isolation is optimizing cell uptake. Previously, exciting only the Cy3 fluorophore and using Cy5 fluorescence as an indicator of loading, intact nb-TIVA-Arg$_9$ was observed to load into several types of cells in addition to neurons. The nb-TIVA-tag prototype gains cell entry through endocytosis by employing a Cys-(D-Arg)$_9$ cell-penetrating peptide (CPP), which is attached to the 5' end of the blocking oligo strand via disulfide linkage, following established protocols (Turner et al., Nucleic Acids Res 2005, 33, 27). Without the (D-Arg)$_9$ CPP, TIVA-tag did not enter cells. Photoactivation of a single neuron resulted in loss of FRET, showing the TIVA-tag can be uncaged in live cells.

The chemistry and biological actions of short, cationic CPPs have been extensively reviewed (Meade et al., 2007, Drug Deliv Rev, 59: 134; Duchardt et al., 2007, Traffic, 8: 848; Trehin et al., 2004, Eur J Pharm Biopharm, 58: 209; Madani et al., 2011, J Biophys, ID:414729). The CPP typically contributes to endosomal release, whereupon disulfide cleavage occurs in the reducing environment of the cytoplasm, trapping the TIVA-tag inside the cell. Several promising cationic CPPs (e.g., see Table 1) are examined, including a 16 amino acid fragment from Drosophila Antennapedia (Derossi et al., J Biol Chem 1994, 269, 10444), which has been demonstrated to move antisense oligonucleotide cargo across the cell membrane in PC12 cells (Troy et al., J Neurosci 1996, 16, 253). Similarly, penetratin and transportan conjugated to siRNA were shown to efficiently mediate knockdown of GFP expression in COS-7 and CHO cells An alternate delivery approach involves targeting specific cell-surface receptors using cell-targeting ligands (CTLs) (Juliano et al., Nucl. Acids. Res. 2008, 36, 4158). One very promising example involved delivery of siRNA to neurons in the brain, by complexation with a peptide that comprises a positively charged (Arg$_9$) sequence to bind the oligonucleotide and a sequence that binds with high affinity to the nicotinic acetycholine receptor in neurons (Kumar et al., Nature 2007, 448, 39). The chimeric peptide selectively delivered siRNA to neural cells expressing the acetycholine receptor, but not to other cells, and silenced a GFP reporter gene in the neuronal cells when used at 10 pmol levels. Folate cyanoethyl-N,N-diisopropyl phosphoramidite (CEP) is available from Barry & Associates and also shows promise for cell delivery, based on the high concentration of folate receptor on many cell surfaces (Li et al., Pharm Res. 1998, 15, 1540; Sudimack et al., Adv. Drug Deliv. Rev. 2000, 41, 147).

TABLE 1

Example cationic CPPs to be tested for TIVA-tag neuronal delivery. Validated nb-TIVA-tag employs R9 peptide (D-Arg)$_9$.

| Name | Sequence | Length | Charge | MW |
| --- | --- | --- | --- | --- |
| Penetratin | RQIKIWFQNRRMKWKK (SEQ ID NO: 1) | 16 | (+) 7 | 2247 |
| TAT | GRKKRRQRRRPPQ (SEQ ID NO: 2) | 13 | (+) 8 | 1719 |
| Transportan | GWTLNSAGYLLGKINLKALAALAKKIL (SEQ ID NO: 3) | 27 | (+) 5 | 2842 |
| R9 peptide | RRRRRRRRR (SEQ ID NO: 4) | 9 | (+) 9 | 1428 |
| MPG peptide | GALFLGWLGAAGSTMGAPKKKRKV (SEQ ID NO: 5) | 24 | (+) 5 | 2445 |
| KALA peptide | WEAKLAKALAKALAKHLAKALAKALKACEA (SEQ ID NO: 6) | 30 | (+) 7 | 3132 |

Based on the success of CPP-labeled TIVA thus far and the potential utility of CTLs, it is expected that several additional delivery vehicles will be identified that produce high neuronal cell uptake in live brain slices, with low toxicity. In assessing each compound, evidence of rapid cell uptake is examined, as this will enable some variations on the experimental paradigm, for example, involving sequential addition of TIVA-tags. Currently, the (D-Arg)$_9$-TIVA prototype is incubated with brain slices for 60 min prior to RNA capture. Cell specificity as well as potential for in vivo studies, are also evaluated for each TIVA-tag. Because TIVA is labeled with Cy3/Cy5, relative fluorescence measurements of cell uptake are made using identical confocal microscope settings (laser power, PMT, confocal pinhole width, etc.) More quantitative measurements (determining x moles of TIVA uptake) can be made with UV-Vis spectroscopy by subtracting the amount of compound depleted from the incubation solution from the total amount of compound added. RNA harvested by the most promising TIVA-tags are analyzed by Bioanalyzer and gel electrophoresis to confirm the correct quantity (~1 µg/cell post-amplification) and size distribution.

Optimizing TIVA Stability in Neurons.

The goal is to develop TIVA-tags that remain completely hybridized and stable for several hours within the cellular environment, as will be important for measuring the stimulated transcription in time-course studies. In the caged state, TIVA-tag should remain intact (i.e., resistant to nucleases) and bind no neuronal RNA. TIVA studies indicated that the hairpin/duplex design with 2'-F RNA capture strand and 2'-OMe RNA blocking strand is very stable in cells, as seen by a stable Cy3-Cy5 FRET signal over 9 hours. In a confirmatory gel experiment, TIVA incubated in serum (80% FBS in DMEM) for 1 hour showed little degradation, visualized by Cy3/Cy5 fluorescence. Thus, the TIVA hairpin appears to be nearly optimized for cell stability, perhaps because relatively few RNA nucleases cleave double-stranded RNA (Dicer being an exception, in siRNA processing). However, longer-time-course in vivo applications may, in certain instances, require that all phosphate backbones are phosphorothioated in the course of solid-phase synthesis (Tang et al., J. Nucl. Acids Res. 2008, 36, 559), as S-DNA and S-RNA can significantly increase nuclease stability (Thierry et al., Biochem Biophys Res Commun 1993, 190, 952). Constructs with greater nuclease resistance and conformational stability, such as locked nucleic acids (LNA) (Wahlestedt et al., Proc. Natl. Acad. Sci. USA 2000, 97, 5633), are thus also tested.

Experiments are conducted to vary the length and composition of the capture strand (18-25mer) to ensure maximal RNA capture post-photolysis, while adjusting the associated blocking strand(s) to prevent background RNA binding pre-photolysis. Initially, in vitro assays will measure thermal stability of capture strand-RNA duplexes, at physiological temperature and salt concentration. The most promising capture strands will then be caged as nb-TIVA, and RNA capture yield (+/−hv) will be assessed in individual cultured neurons.

Prototype TIVA-tag was constructed with 18mer poly-U 2'-F RNA capture strand and two complementary 7mer poly-A 2'-OMe RNA blocking strands. As desired, this produced a very large differential stability: $T_{m\ caged}=59\pm1°$ C., $T_{m\ uncaged}<25°$ C.; $\Delta T_m>30°$ C. In certain instances, longer poly-U strands may be needed to capture maximal cell mRNA, as the $T_m$ for uncaged TIVA binding to a 20mer poly-A RNA target was just 50° C. In lengthening the poly-U strand, possible background RNA binding may also be reduced by increasing the $T_m$ of caged TIVA to 70-80° C., as it is found useful with caged hairpin oligos in previous cell and embryo experiments (Tang et al., J. Nucl. Acids Res. 2008, 36, 559; Tang et al., 2007, J Am Chem Soc, 129: 11000). If necessary, both strands can be flanked with complementary GCG/CGC units to increase binding energy and specificity. Further, the use of poly-U LNA or morpholino in the capture strand is explored.

Quantifying RNA Yield and Transcript Distribution

Presented herein are recently developed protocols to validate the mRNA-isolating property of TIVA-tag in live cells. TIVA-tag is added to primary cultures of dispersed mouse brain cells (mixed culture), the TIVA-tag is then photoactivated in a single neuron, the loss of FRET signal (Cy3 emission increases, Cy5 decreases) is evaluated, all of the cells from the mixed culture are lysed, and the TIVA-mRNA hybrids that were formed in the single neuron are affinity isolated, and the TIVA-mRNA hybrids from the coverslip are subsequently affinity-purify. In certain instances, amplification (Eberwine et al., Proc Natl Acad Sci USA 1992, 89, 3010; Morris et al., J. Vis. Exp. 2011, 50, e2634) of the isolated mRNA is necessary for transcriptomics purposes because a single cell contains a few picograms of mRNA, which is below the detection threshold of current sequencing technologies. Bioanalyzer analysis of the resultant material shows that amplification after photoactivation produces nearly 1 microgram of amplified RNA (aRNA), whereas in the absence of photoactivation there was no amplifiable nucleic acid. This indicates that TIVA-tag did not spontaneously activate inside cells and there was little nonspecific mRNA capture during the affinity purification process. RNAseq transcriptome analysis of TIVA-isolated mRNA showed that single neurons expressed thousands of different transcripts, and that among these transcripts, neuronal markers were enriched as opposed to glial, progenitor and vascular markers (Lovatt et al., Neurosci. 2007, 27, 12255; Cahoy et al., J Neurosci 2008, 28, 264). These experiments demonstrated that the TIVA-tag is an efficient tool for isolating mRNA from single cells. But, in order to improve reproducibility and quantitation capabilities and enable longitudinal studies, it is critical to optimize TIVA chemistry, in vivo photoactivation, and RNA isolation procedures.

Similar RNA yields were obtained with nb-TIVA-tag in acute hippocampal slices from mice and also from human brain slices obtained post-surgery (Lovatt et al., 2013, Nat Methods, 11(2): 190). Pyramidal neurons took up TIVA-tag, and photoactivation of single neurons resulted in a robust loss of FRET signal, validating efficient uncaging. As a control for cell-specific photoactivation, neurons adjacent to the photoactivated cell (indicated by dotted circle) did not demonstrate changes in FRET. This also shows that photoactivated TIVA-tag remains within the cell(s) of interest and does not migrate to neighboring cells. Following photoactivation, the region containing the field of view was aspirated by pipette, the tissue was lysed, and TIVA-mRNA hybrids were isolated by affinity purification. Single-cell RNAseq analysis of the TIVA-isolated mRNA yielded transcriptome profiles that contained about 9000 expressed transcripts, in line with previous studies reporting on the number of transcripts expressed by populations of neurons (Lovatt et al., Neurosci. 2007, 27, 12255; Cahoy et al., J Neurosci 2008, 28, 264). Importantly, RNA-sequencing of single neurons revealed that neuronal markers were greatly enriched while glial and vascular markers were almost entirely absent, validating the cell specificity of the TIVA-capture procedure. Even long transcripts of several thousands of nucleotides in length had read coverage over the entire length of the mRNA comparable to that of mRNA isolated from whole tissue, suggesting that the TIVA-isolated mRNA was not degraded. These data confirm that TIVA is an efficient tool for capturing mRNA from single cells in the live slice preparation, which is the current standard for most neurobiological in vivo studies. Similar RNA quantitation and analysis are performed in live brain slices with the proposed TIVA-tags.

Affinity Tagging for Multiplexing.

Biotin is readily incorporated into TIVA-tags by solid-phase synthesis using a 3'-biotin CPG from Glen Research. Neuronal RNA bound to biotinylated TIVA-tag is pulled down using streptavidin-coated beads, and subsequently released by thermal melting. For multiplexing/longitudinal studies requiring additional affinity tags, the plant steroid digoxigenin (Dig) is employed, which is sold by Gene Link as the NHS ester. This is covalently attached to the oligonucleotide via an active primary amine phosphoramidite (e.g., Amino Linker C6, Gene Link), which is incorporated by solid-phase synthesis. Anti-Dig probes are widely available for isolation purposes. Another small hapten (MW 500 amu) is dinitrophenyl (DNP), which is available with PEG linker as the phosphoramidite from Gene Link. RNA harvesting occurs using anti-DNP antibodies (Roche) on agarose beads (Hsu et al., Nucleic Acids Research 2009, 37, e77). If necessary, multiple Dig or DNP affinity tags may be incorporated within TIVA to increase pull-down efficiency (Grzybowski et al., Nucl. Acids Res. 1993, 21, 1705). Biotin, Dig, and DNP all offer the advantage of small molecules, with minimal chance of affecting TIVA uptake, toxicity, or RNA capture efficiency. A second approach involves peptide tags: FLAG-tag (DYKDDDDK (SEQ ID NO: 7)), HA-tag (YPYDVPDYA (SEQ ID NO: 8)), and Myc-tag (EQKLISEEDL (SEQ ID NO: 9)) are well recognized by antibodies (Sigma-Aldrich). The N-terminal Cys-FLAG, HA, or Myc peptides can be attached to TIVA via a maleimide linker (as phosphoramidite, Gene Link). Using the same mixed culture, yields of RNA captured (from Bioanalyzer data) and sequences of RNA captured (from RNA-seq transcriptome analysis) are compared for the six most promising affinity tags, with trials of at least 5 individual cells per TIVA-tag. The yields are expected to vary somewhat for the different affinity tags, which is acceptable so long as sufficient RNA material can be reproducibly isolated for transcriptome analysis, with comparable distribution and quality of RNA transcripts.

Experiments presented herein leads to a cohort of at least six nb-TIVA-tags that are capable of efficient cell entry via attached CPP/CTL, remain in hairpin/duplex structure, and are stable to nucleases. Possessing an optimized mRNA capture strand, photoactivated probes will stably bind the available cellular mRNA and allow precise analysis of mRNA yield and sequence, following RNA amplification.

Example 2: Ru-TIVA

Mammalian nervous system cells are highly complex cells often with polarized processes that are intermingled with neighboring cells of not necessarily the same cell type. This motivates the development of focally-specific, not-mechanically-invasive, non-toxic photochemical methods for isolating mRNA from single cells in their native microenvironment. Using 1-P excitation, prior studies validated use of nb-TIVA in cultured, dispersed neurons or near the surface of brain slices. However, in certain instances, using nb-TIVA, it is difficult to interrogate individual cells buried tens-to-hundreds of microns in living brain tissue without risking uncaging/mRNA contamination from cells above and below the desired cell. The standard 2-nitrobenzyl moiety absorbs optimally ~365 nm, which is somewhat toxic to cells, and near-UV light penetrates poorly into tissue, due to absorption from endogenous chromophores and the fact that light scatters as $1/\lambda^4$. Although nb-TIVA can be activated with 405 nm, the absorbance band tails to nearly zero at this wavelength, therefore requiring longer illumination times. Furthermore, nitrobenzyl-TIVA-tags have very low 2-P absorption cross-sections (<0.01 GM) (Aujard et al., 2006, Chemistry—Eur. J., 12: 6865). Finally, multiplexing studies require the development of new photo-caging moieties that can be excited with visible (1-P) or near-IR (1-P or 2-P) lasers.

To generate synthetically and spectrally tunable photolinkers for caging TIVA, the rich inorganic photochemistry of ruthenium bis(2,2'-bipyridine)(X)$_2$ compounds is used (Badaeva et al., 2010, Phys. Chem. Chem. Phys. 12: 8902; Balzani et al., 2001, Coord. Chem. Rev. 211: 97; del Mármol et al., 2010, Anal. Chem. 82: 6259; Fino et al., 2009, Front. Neur. Circ. 3: 1; Kanemoto et al., 2011, PLoS ONE, 6: e22652; Nikolenko et al, 2011, Cold Spring Harbor Protocols, 2011: pdb.top111; Nikolenko et al., 2005, Chem. Commun. 2005: 1752; Ramirez et al., 2012, Inorg. Chem. 51: 1261; Rial Verde et al., 2008, Front. Neur. Circ. 2; Salassa et al., 2008, J. Am. Chem. Soc. 130: 9590; Salassa et al., 2009, J. Inorg. Chem.48: 1469; Salierno et al., 2008, Eur. J. Inorg. Chem. 2008: 1125; Singh et al., 2004, Inorg. Chem. 43: 7260; Wilker et al., 1999, Angew. Chem. Int. Ed. 1-2: 90; Zayat et al., J. Am. Chem. Soc. 125: 882; Zayat et al., Inorg. Chem.45: 1728), where X is usefully photolabile when composed of amine, pyridine, imidazole, or thioether ligands. This work builds on prior use of Ru(bpy)$_2$ to cage glutamate, GABA, and rhodamine dye (all coordinated to Ru$^{2+}$ via the amine) (del Mármol et al., 2010, Anal. Chem. 82: 6259; Fino et al., 2009, Front. Neur. Circ. 3: 1; Nikolenko et al., 2005, Chem. Commun. 2005: 1752; Ramirez et al., 2012, Inorg. Chem. 51: 1261; Rial Verde et al., 2008, Front. Neur. Circ. 2; Salierno et al., 2008, Eur. J. Inorg. Chem. 2008: 1125; Singh et al., 2004, Inorg. Chem. 43: 7260; Zayat et al., J. Am. Chem. Soc. 125: 882; Zayat et al., Inorg. Chem.45: 1728). DFT calculations provide a strong theoretical basis for understanding Ru(bpy)$_2$(X)$_2$ photodissociation chemistry, which requires thermal population of the triplet ligand field state(s) ($^3$LF) from the excited $^3$MLCT state (Badaeva et al., 2010, Phys. Chem. Chem. Phys. 12: 8902; Ramirez et al., 2012, Inorg. Chem. 51: 1261; Salassa et al., 2008, J. Am. Chem. Soc. 130: 9590; Salassa et al., 2009, J. Inorg. Chem.48: 1469) Ligand exchange quantum yields generally depend on the energy gap between $^3$LF and $^3$MLCT states, thus blue-shifting the $^3$MLCT band typically reduces this gap and favors photodissociation (Garner et al., 2012, Inorg. Chem. 50: 4384). Because direct Ru$^{2+}$ ligand substitution chemistry typically requires elevated temperatures (>70° C.) over several hours, which would be impossible to perform with an intact oligo or TIVA molecule, the present strategy focuses on installing X ligands bearing alkynes for subsequent mild, high-yielding reaction with azide-containing oligos. The Ru-bis-alkyne provides a homo-bifunctional photolinker, for circularization with an oligo terminated with azide at both ends, or a hairpin formed with two different azide-terminated oligos. In certain instances, Ru-TIVA is designed using alkyne-modified pyridine ligands, as pyridine dissociates in high quantum yield (4-40% upon 1-P excitation of MLCT, depending on pyridine functionalization) and gives decent 2-P absorption cross-sections, 0.1-1.0 GM at 800 nm.

A novel photolinker [Ru(bpy)$_2$(3-ethynyl-pyridine)$_2$](PF$_6$)$_2$, [Ru(3-EP)$_2$](PF$_6$)$_2$ (FIG. 1), was recently synthesized by modifying published procedures for Ru(bpy)$_2$(5-cyanouracil)$_2$ (Zayat et al., 2003, J. Am. Chem. Soc., 125: 882; Garner et al., 2012, Inorg. Chem. 50: 4384) Ru(bpy)$_2$Cl$_2$ (101.8 mg, 0.20 mmol) was suspended in dry MeOH (10 mL). To this AgSO$_3$CF$_3$ (105 mg, 0.41 mmol) was added and placed in the freezer overnight under N$_2$, yielding Ru(bpy)$_2$(SO$_3$CF$_3$)$_2$ The solution was then warmed to rt, filtered to remove AgCl, and 3-ethynylpyridine (202 mg, 0.40 mmol) was added. The reaction was heated to 75° C. for 5 h until no further changes were observed by UV-Vis. The MeOH was removed under reduced pressure and product was redissolved in boiling water. After chilling, solid NH$_4$PF$_6$ was added to yield a light orange precipitate, which was filtered, washed twice with cold water and dried. Crude product was purified by silica flash chromatography with a 4:1 dichloromethane/acetonitrile eluent. Final mass: 106.6 mg, 88% yield. Pure compound was characterized by $^1$H NMR (500 MHz, in CD$_3$CN), cyclic voltammetry, ESI mass spectrometry, UV-Vis spectroscopy, elemental analysis. High-resolution X-ray structure determination (FIG. 1) confirmed that the reactive ethynes are correctly oriented ($\theta_{N-Ru-N} \approx 60°$) for reaction with azido-oligos to generate closed hairpin or circular structures. Finally, water-soluble [Ru(3-EP)$_2$]Cl$_2$ was synthesized by dissolving [Ru(3-EP)$_2$](PF$_6$)$_2$ in minimal acetone, adding tetrabutylammonium chloride and isolating red precipitate.

Ru Photochemistry Compatible with Biology and RNA Capture.

A "RuBi"-glutamate complex with similar ligand set to the proposed Ru linkers is commercially available (Tocris Bioscience) and has been employed extensively for mapping neural circuits in live brain slices. These in vivo studies highlight that the chelated Ru$^{2+}$ is non-toxic in neurons, and repeated Ru photoexcitation in the soma produces no loss of neuronal function (Nikolenko et al, 2011, Cold Spring Harbor Protocols, 2011: pdb.top111). The current Ru(bpy)$_2$-caged amines can be activated with either visible light (e.g., 473 nm) or 2-P ($\kappa_{2P}$=800 nm). RuBi-caged GABA shows favorable solubility, stability, and photophysical parameters compared to most organic chromophores: ε (1P, 424 nm)=6400 M$^{-1}$ cm$^{-1}$, Φ=0.2, εΦ=1280 (Matsuzaki et al., 2010, Nat Chem Biol, 6: 255).

Figure 2:
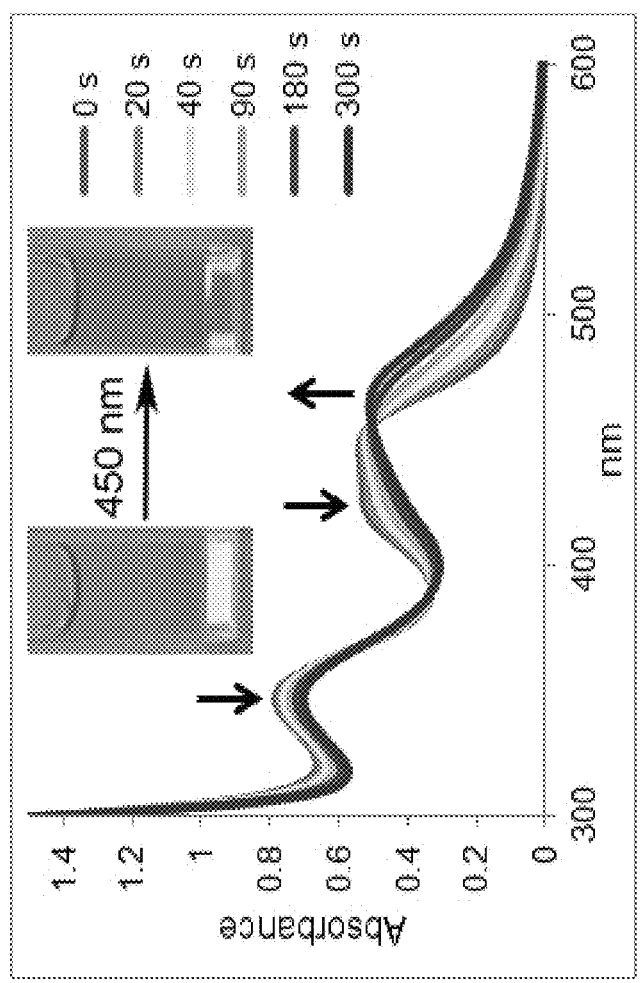
FIG. 2 depicts the results of experiments demonstrating that RuBEP photolysis in $H_2O$ in open air with 450 nm laser cleanly and rapidly produces $Ru(bpy)_2(3-EP)(OH_2)$.
Figure 3:
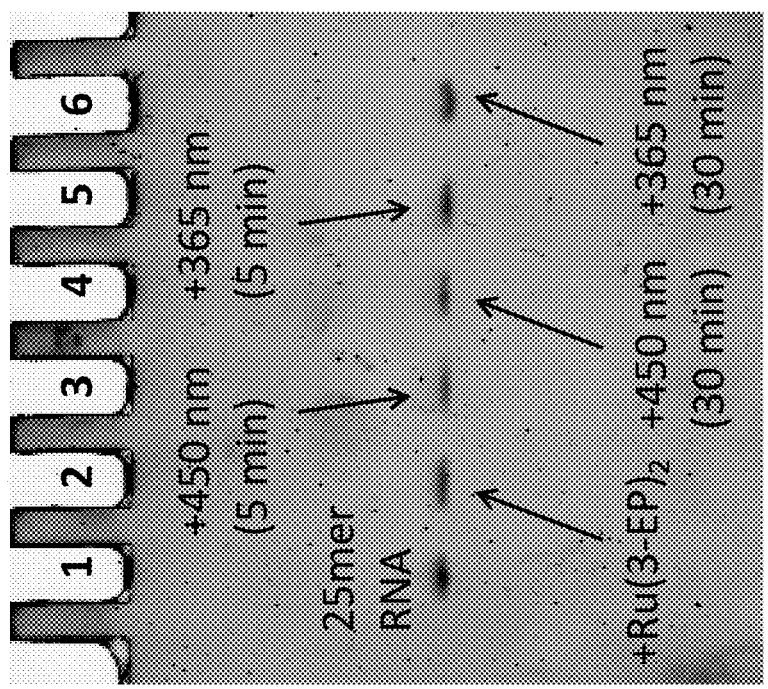
FIG. 3 is an image of a gel showing no RNA damage with RuBEP (+/−hv).

RuBEP (+/−hν) is similarly non-toxic, as determined by microinjection into 1-cell-stage zebrafish embryos, observed at 24 and 48 hours. An open-air photolysis-kinetics experiment (FIG. 2) showed three clear isosbestic points and lack of photobleaching, thus confirming lack of O2-mediated photodegradation. Likewise, gel electrophoresis indicated no damage to 25mer RNA in the presence of RuBEP irradiated up to 30 min with 450 nm laser (5 mW) or 365 nm light (9 mW/cm$^2$) (FIG. 3). These experiments confirm that excited state [RuBEP]$^{2+*}$ channels the energy efficiently from the $^3$MLCT state to the ligand dissociative $^3$LF state, which makes [RuBEP]$^{2+*}$ a poor photosensitizer for dioxygen. Thus, reactive oxygen species should not be a concern for Ru-TIVA RNA harvesting in brain slices.

Ru Photophysical Studies.

The studies presented herein focus on developing Ru-TIVA constructs using the RuBEP photolinker. UV-Vis (FIG. 2) and $^1$H 2-D NMR spectroscopy studies confirmed that photodissociation of one 3-EP ligand occurs in very high yield (Φ=0.33, ε(1P, 445 nm)=6700 M$^{-1}$ cm$^{-1}$). In 2-P microscopy studies, Yuste has demonstrated the capability of combining neuronal imaging of GFP ($\lambda_{2P}$=850 or 900 nm) or Alexa-594 (2P, low-power 800 nm) with 2P-uncaging of RuBi-glutamate ($\lambda_{2P}$=800 nm, 150-300 mW), as will be essential for many of the in vivo studies with Ru-TIVA. Due to the smaller 2-P uncaging volume, two-photon absorption cross-sections for all Ru-TIVA constructs are measured using Cy3-Cy5 or more red-shifted FRET reporter. Reported values for similar Ru-bpy complexes are 0.1-1.0 GM at 800 nm.

Circular Ru-TIVA.

Figure 4:
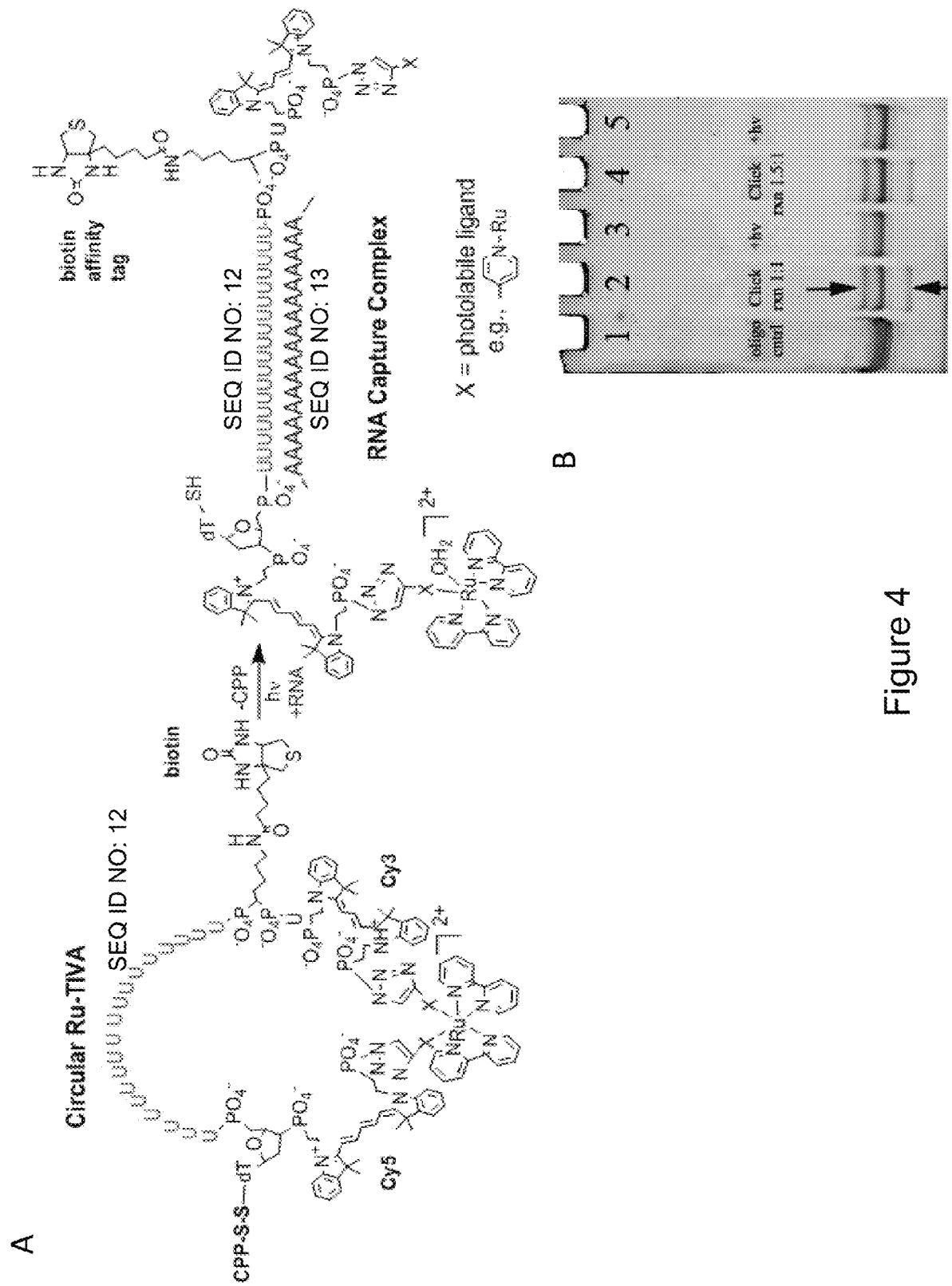
FIG. 4, comprising

A circular Ru-TIVA architecture is designed (FIG. 4A), which builds on the previous design of a circular caged DNAzyme (Richards et al., 2010, J ChemBioChem, 11: 320) and antagomir (Gripenburg et al., 2013, Bioorg Med Chem Lett, 21(20): 6198). The circular design offers rapid, high RNA capture efficiency (without blocking strands), and the ease of installing a single Ru-linker. To incorporate the CPP via disulfide linkage within the circular loop, "S-Bz-Thiol-Modifier C6-dT" (Glen Research) is employed. To promote efficient Ru-oligo conjugation under mild conditions, the [3+2] Cu(I)-mediated Huisgen cycloaddition reaction between azides and alkynes was employed (Kolb et al., 2001, Angew Chem Int Ed., 40: 2004; Rostovtsev et al., 2002, Angew Chem Int Ed., 41: 2596). This 'click chemistry' has been applied extensively for several applications (Tang et al., 2008, J Nucl Acids Res, 36: 559; Aaron et al., 2008, J. Am. Chem. Soc., 130: 6942; Chambers et al., 2009, J. Am. Chem. Soc., 131: 563; Hill et al., 2007, J. Am. Chem. Soc. 129: 9262. Hill et al., 2009, J. Am. Chem. Soc., 131, 3069; Seward et al., 2011, J. Chem. Sci., 2: 1103; Seward et al., 2008, Bioconjug. Chem., 19: 2129) and recently was used to react a Ru(bpy)$_2$-coordinated bpy-ethyne with an aryl azide (Baron et al., 2012, Inorg. Chem., 51: 5985. To generate a Ru-TIVA prototype, solid-phase synthesis of the capture strand was performed. The free 5' and 3' amines was revealed during cleavage from solid support, and subsequently reacted with excess azidobutyrate NHS ester linker (Glen Research) to install azide on both ends. Two routes to produce the desired circular Ru-TIVA is pursued: i) cyclization with RuBEP followed by thiol reaction with Cys-(Arg)$_9$, or ii) CPP-reaction, followed by cyclization. No oligo side-reactions using click chemistry are observed by either route, but (i) appears to be higher yielding.

Performing click chemistry with the Ru-ligand-ethyne minimizes side-reactions and occurs at rt, which is minimally perturbing to the oligo. Thus, [Ru(bpy)$_2$X$_2$]Cl$_2$ was synthesized where X is 3-ethynyl pyridine or 4-ethynyl pyridine, following published procedures for refluxing [Ru(bpy)$_2$Cl$_2$]$^{2+}$ and excess pyridine ligand in EtOH/H$_2$O for 4 h, and purifying by precipitation. TLC-pure material was isolated in 80% yield. The $^1$MLCT ($\lambda_{max}$=455 nm) is consistent with similar [Ru(bpy)$_2$(Pyr)$_2$]$^{2+}$ complexes, and photolysis at 458 nm led to rapid formation of [Ru(bpy)$_2$(3-ethynyl-Pyr)(H$_2$O)]$^{2+}$ with $\lambda_{max}$ ~470 nm. An experiment was performed with [Ru(bpy)$_2$(3-ethynyl-Pyr)$_2$]$^{2+}$ and a 25mer DNA oligo functionalized with azide at both the 5' and 3' ends. SDS-PAGE strongly suggests that click chemistry is joining both ends of the circular oligo with the Ru linker (FIG. 4B, lanes 2 and 4, black arrows point to two products); as expected, photolysis results in disappearance of fastest moving band (FIG. 4B, lanes 3 and 5), which is likely the circular Ru-oligomer product. Circular Ru-TIVA, is then subject to characterization by MALDI-TOF MS, HPLC, absorption and emission spectroscopy, gel electrophoresis, and cyclic voltammetry. A gel shift assay assesses whether circular Ru-TIVA binds to target 25mer poly-A RNA. Circular Ru-TIVA can be optimized to minimize background RNA binding, if necessary, by varying the oligo loop size and composition.

Figure 5:
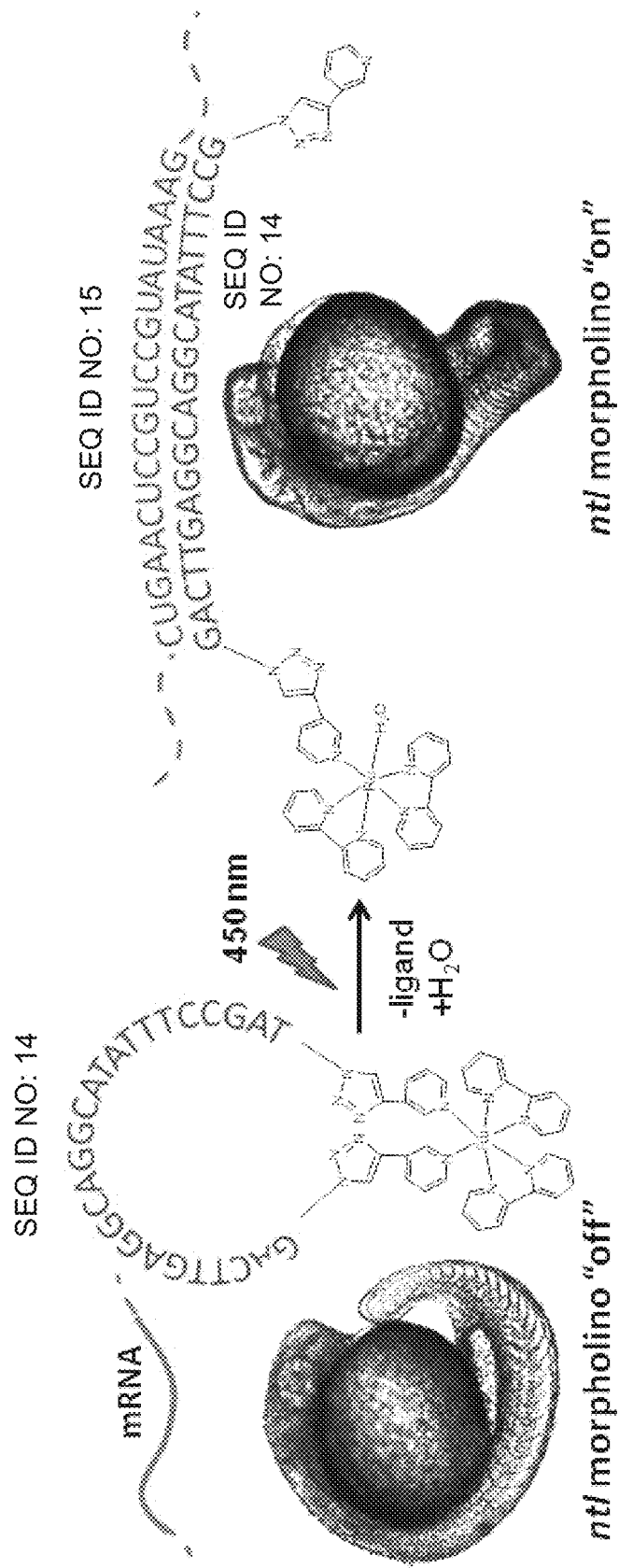
FIG. 5 is an illustration demonstrating that circular Ru-MO (red) binds mRNA (blue) and knocks down gene expression in the zebrafish embryo upon 450 nm activation. Representative images for wild-type and ntl embryos shown.

To develop the Ru-cyclization chemistry and test in vivo caging efficiency, a 25mer ntl morpholino (MO) oligonucleotide terminated by azide at both 3' and 5' ends (Gene Tools) was reacted with RuBEP (rt to 50° C., 1-2 days, low conc., at 1.2:1 stoichiometry), and gave the desired cyclized Ru-oligo product in >80% yield (FIG. 5). Formation of the cyclized Ru-oligo product was confirmed by gel electrophoresis, and irradiation of the circular Ru-oligo with 450 nm laser gave the expected linear cleavage product, which ran somewhat faster on gel. Finally, circular ntl Ru-MO or ntl MO (control) was microinjected into 100 1-cell stage zebrafish embryos (FIG. 5). More than 80% of embryos injected with ntl MO or Ru-MO continued developing to 48 h, indicating lack of Ru (photo)toxicity. 85% of Ru-MO embryos irradiated with 450 nm laser (2 min, 5 mW) developed a severe no-tail phenotype vs. 83% of ntl MO embryos, confirming complete uncaging and lack of effect of pendant Ru on MO binding to target mRNA. Only 15% of Ru-MO embryos left in the dark showed ntl phenotype. This experiment validates the Ru-circular-caging approach.

Circular Ru-TIVA is optimized to minimize background RNA binding by varying the oligo loop size (18-25 nt), as has been successful in previous examples (Yamazoe et al., 2012, Angew. Chem. Int. Ed., 51: 6908; Wu et al., 2013, Nucl. Acids Res., 41: 677; Tang et al., 2010, Nucl. Acids Res., 38: 3848). More hydrophobic oligo backbones should lead to compaction in water, and better caging. In certain instances, complete caging is also favored by adding complementary nucleotides adjacent to the Ru, creating a tighter stem-loop structure. In addition to zebrafish experiments, gel-shift assays will help to identify circular Ru-oligo designs that are optimally caged to block RNA binding.

Hairpin Ru-TIVA.

It has been demonstrated that oligo hairpins with single photocleavable linker can be engineered to modulate target mRNA binding (Dmochowski et al., 2007, Biotechniques, 43: 161; Tang et al., 2006, Chem. Int. Ed., 45: 3523; Tang et al., 2007, J. Mol. Biosys., 3: 100; Tang et al., 2007, J. Am. Chem. Soc., 129: 11000; Tang et al., 2008, J. Nucl. Acids Res., 36: 559; Ouyang et al., 2009, J. Am. Chem. Soc., 131: 13255). Thus, in the hairpin Ru-TIVA design, the same cycloaddition chemistry described previously is performed, reacting RuBEP with the 3' end of the $N_3$-poly-U capture strand and the 5' end of the $N_3$-poly-A blocking strand. The solid-phase synthetic incorporation of 3'-affinity tag, Cy3, Cy5, and 5' thiol for reaction with Cys-CPP is otherwise identical to nb-TIVA. In vitro Cy3/Cy5 FRET assays monitor duplex stability (+/−hv) in the presence of 25mer RNA target.

Characterization and Application of Ru-TIVA-Tags.

Circular and hairpin Ru-TIVA-tags functionalized with optimal CPPs/CTLs and affinity tag are synthesized and compared for cell uptake, stability, and RNA harvesting capabilities. $Ru(bpy)_2(X)_2]^{2+}$ complexes do not intercalate into a DNA base stack (Mihailovic et al., 2006, Langmuir, 22: 4699), and show no evidence of neurotoxicity, similar to RuBi-GABA and Ru-glutamate (Fino et al., 2009, Front. Neur. Circ. 3: 1; Nikolenko et al, 2011, Cold Spring Harbor Protocols, 2011: pdb.top111; Nikolenko et al., 2005, Chem. Commun. 2005: 1752; Rial Verde et al., 2008, Front. Neur. Circ. 2). Effective Ru-TIVA designs are employed to assess transcriptome variability in different hipppocampal regions in the live mouse brain slice model.

To assess regional RNA variability, 3 slices taken from different depths are examined for 3 different regions of the horn-shaped hippocampus: the dentate gyrus (DG) and the cornu ammonis (CA), regions 1 and 3. RNA from 5-10 cells from each brain slice are harvested by TIVA-tag, for a total of ~70 cells. Experimental details of the cell loading and RNA sequencing protocols are provided elsewhere herein. These data will be compared to normal single-cell variability determined from 10 cells in mixed culture: Experiments using nb-TIVA-biotin-(D-Arg)$_9$ yielded the data shown in FIG. 6. A baseline for low transcriptome variability should be seen in the mixed culture, based on loss of normal neuronal connections and their culturing in a shared, buffered in vitro system.

Ru-TIVA Variants.

X ligands are purchased or synthesized with a terminal alkyne and the corresponding $Ru(bpy)_2(X\text{-alkyne})_2$ complexes are synthesized for facile reaction with azido-oligos. A palette of Ru-TIVA compounds are developed that exhibit maximal 2-P uncaging between 750 and 1050 nm, and afford the possibility to achieve spatially and temporally selective RNA capture by combining orthogonal photo-activation with selective affinity tags. The observed $^1$MLCT Ru→bpy ($\pi_1$*) transition ($E_{op}$) varies widely in energy for [Ru(bpy)$_2$X$_2$]$^{2+}$ compounds highlighted in Table 2, where X is readily photodissociable at a wide range of 1-P energies approximating $E_{op}$ (Dodsworth et al., Chem. Phys. Lett. 1986, 124, 152). If X is amine (NH$_2$R) instead of pyridine (Pyr), MLCT band red-shifts to $\lambda_{max}$≈490 nm from $\lambda_{max}$≈455 nm, while maintaining efficient photolysis (Φ≈0.1). Primary amine ligands with terminal alkyne are available in several chain lengths (n=3-6). This affords the possibility to employ both pyridyl- and primary amine-Ru ligands, to generate Ru-oligos that can be photodissociated selectively. Likewise, Ru-X$_2$ ligand-linkers incorporating (NCS)$_2$ and (MeSPh)$_2$ will expand the MLCT palette to 520 nm and 404 nm (Table 2), with useful photodissociation quantum yields (Garner et al., Inorg. Chem. 2012, 50, 4384). Electron-donating substituents on the bpy (e.g., methyl) will blue-shift the MLCT band for multiplexing studies ($\lambda_{2P}$≈750 nm). And, it is explored whether 2-P absorption is enhanced in Ru complexes with one electron-donating bpy and one electron-withdrawing bpy, (Badaeva et al., Phys. Chem. Chem. Phys. 2010, 12, 8902) by promoting charge migration across the excited-state [Ru(bpy)$_A$(bpy)$_B$(X)$_2$]$^{2+*}$ chromophore.

TABLE 2

Optical parameters for several [Ru(bpy)$_2$X$_2$]$^{2+}$ compounds

| X$_2$ | $E_{ep}$ (cm$^{-1}$) | $\lambda_{max}$ (nm) |
|---|---|---|
| (NCS)$_2$ | 19230 | 520 |
| (NH$_3$)$_2$ | 20410 | 490 |
| (N-MeIm)$_2$ | 20700 | 483 |
| 4-allyl-1,2,4-triazole | 21190 | 472 |
| (Pyr)$_2$ | 21980 | 455 |
| (4-AcPyr)$_2$ | 22620 | 442 |
| (MeSEt)$_2$ | 23697 | 422 |
| (PPh$_3$)$_2$ | 23870 | 419 |
| (MeSPh)$_2$ | 24752 | 404 |

The experiments described herein results in the development of a cohort of Ru-TIVA-tags with efficient 2-P uncaging with fs-pulsed NIR laser, as required for deep-tissue RNA harvesting. Studies in live brain slices provide the most accurate assessment to date of transcriptome variability at two levels of organization—cell and tissue—and can easily be extended to different brain regions. Ru(bpy)$_2$X$_2$ caging strategies developed through this work provide the first examples of oligonucleotide photoactivation using visible (1-P) and near-IR (2-P) light, which is applicable to many areas of neurobiology, developmental and cancer biology.

Example 3: Ru-TIVA for Multiplexed Studies of CREB

There are few examples to date of multiplexed uncaging of biomolecules using light of two visible or NIR wavelengths (Fino et al., Front. Neur. Circ. 2009, 3, 1; Kantevari et al., Nat Meth 2010, 7, 123). Ru-caging chemistry has been explored by the Etchenique lab over the past 10 years, but has involved only a few pyridine and amine ligands using the commercially available Ru(bpy$_2$)Cl$_2$ or Ru(tpy)(bpy)Cl starting materials (Salierno et al., Eur. J. Inorg. Chem. 2008, 2008, 1125; Zayat et al., Inorg. Chem. 2006, 45, 1728). Salassa and coworkers have provided spectroscopic and computational studies (Salassa et al., J. Am. Chem. Soc. 2008, 130, 9590; Salassa et al., Inorg. Chem. 2009, 48, 1469) and more recently, Turro has explored Ru(bpy$_2$)-thioether photolysis (Garner et al., Inorg. Chem. 2012, 50, 4384).

By extending this Ru(bpy$_2$)X$_2$ chemistry to other X ligands (see Table 2), and varying the electron-donating ability of the bpy ligands, greater tunability of the Ru 1P- and 2P-dissociation chemistry is gained.

For example, the multiplexed TIVA-tags described herein may comprise several differentially photo-addressable RNA-capture strands, and will establish new frontiers in the application of photochemistry to biology. New caging moieties, particularly those absorbing at different visible wavelengths, with minimal cross-talk and possessing large 2-P absorption cross sections, are needed to advance many areas of science. Moreover, longitudinal studies of cellular gene expression using, for example, fluorescent protein reporters, typically yield information for only a handful of pre-determined genes. Thus, the use of TIVA and RNAseq to monitor RNA transcript levels for thousands of genes, in cells maintained in the biologically correct microenvironment, at high spatial resolution and with temporal control, will revolutionize the understanding of in vivo gene regulatory processes. TIVA will impact many areas of neurobiology, cancer biology and developmental biology and can also be applied to different biomedical problems, such as tumorigenesis, in diverse cell types and regions of the body.

For example, using TIVA, mRNA variability in hippocampal brain regions can be quantified between individual cells in different microenvironments. It is hypothesized that cellular microenvironment should contribute to greater transcriptome variability between neurons in different regions of the brain, relative to neurons organized in the same tissue, or connected by synapse. This exemplary study reflects those which can be examined using 2-photon-activatable compounds as discussed below. The degree to which a neuron's mRNA complement dictates its in vivo function is a very significant and fundamental biological question that has not been satisfactorily answered using other mRNA-harvesting approaches. TIVA can also be used to assess temporal and spatial aspects of transcriptome changes in response to genetic perturbation. For example, studies presented herein focus on the transcription factor CREB (cAMP Response Element Binding protein), which modulates various cAMP-coordinated behaviors including learning and memory, drug addiction, and fear conditioning. Using TIVA in animal model systems allows, for the first time, to assess the breadth of gene expression targets of CREB in vivo. This gives a more accurate and nuanced view of CREB-dependent transcription in the brain, which is likely relevant, for example, to understanding why some areas of cerebral cortex produce seizures in epileptic patients. Identifying spatially and temporally restricted patterns of biomarkers for human diseases will lead to new mechanistic insights and potential therapeutic targets.

In one experimental paradigm, several differentially caged TIVA-tags are introduced into a brain slice and subsequently activated at different time points within the same cell, pre- and post-stimulus. Much like fishing boats that take turns trawling the same waters over minutes-to-hours, each TIVA-tag "net" the available RNA in a cell upon photoactivation at a specific time point, until all TIVA-tags are activated and the time course is completed. The cell(s) of interest are then be extracted from tissue and lysed, and the RNA "catch" will finally be isolated from each TIVA-tag, using different affinity tags (which also provide a time stamp). The pairing of different caging moieties with specific affinity tags, coupled with state-of-the-art 2-photon-microscopic laser-uncaging, yield the necessary spatial and temporal control.

CREB

Activation of a transcription factor known as the cAMP response element binding protein (CREB) is the final step in a signal-transduction pathway, which is initiated by the binding of a specific class of cell-surface receptors. Binding of ligand to a G$_s$ protein-coupled receptor, such as the D1 dopamine receptor or the 5-hydroxytryptamine-1 receptor, liberates G$_s$ protein from the G-protein complex. Subsequently, G$_s$ activates adenylyl cyclase, which in turn stimulates cAMP production. The increase in intracellular cAMP induces the dissociation of protein kinase A (PKA) catalytic subunits from their regulatory subunits. The catalytic subunits move into the nucleus, where they phosphorylate a number of proteins, including CREB. CREB phosphorylation is required for CREB-mediated stimulation of transcription. PKA phosphorylates CREB on Ser133, with CREB stimulation of transcription, peaking at approximately 30 min after cAMP stimulation, followed by a gradual decrease to basal levels through the activity of phosphatases.

Figure 6:
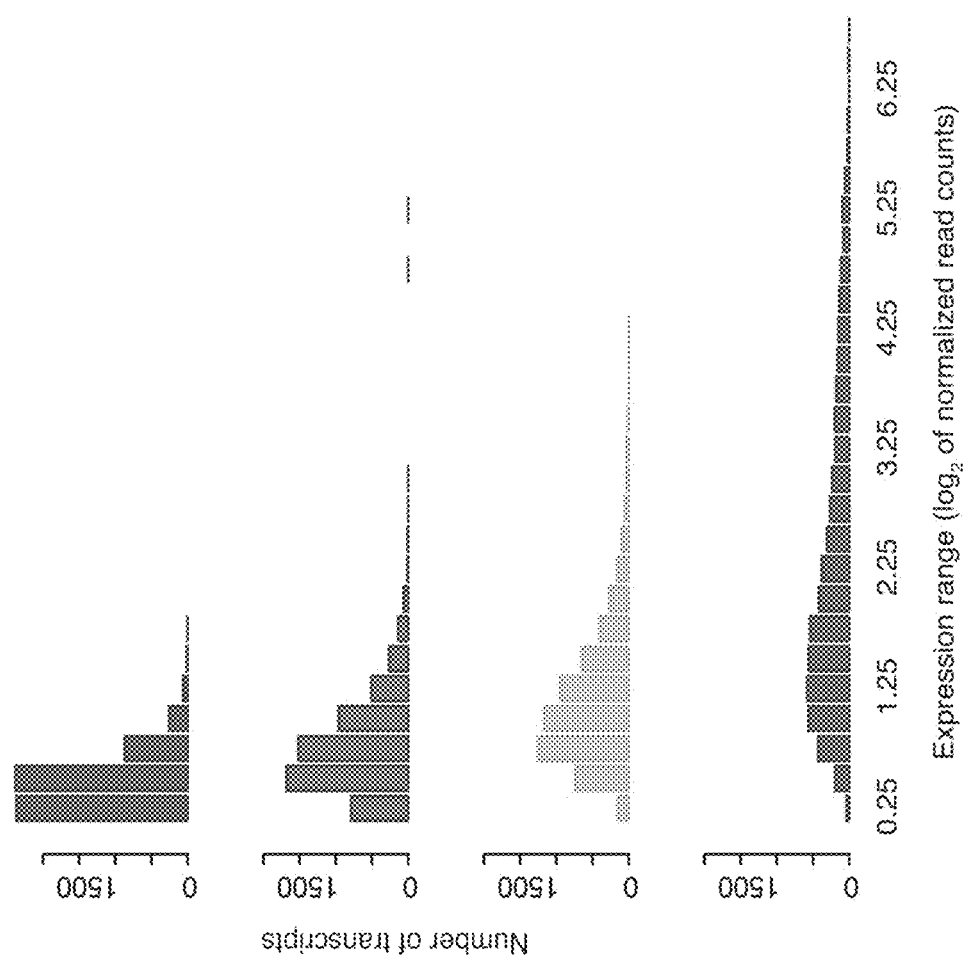
FIG. 6 is a graph depicting single hippocampal neurons analyzed by TIVA from culture (orange) or tissue (red) demonstrate wider range of RNA expression than populations of cells in mixed culture (blue) or whole tissue (green).
Figure 7:
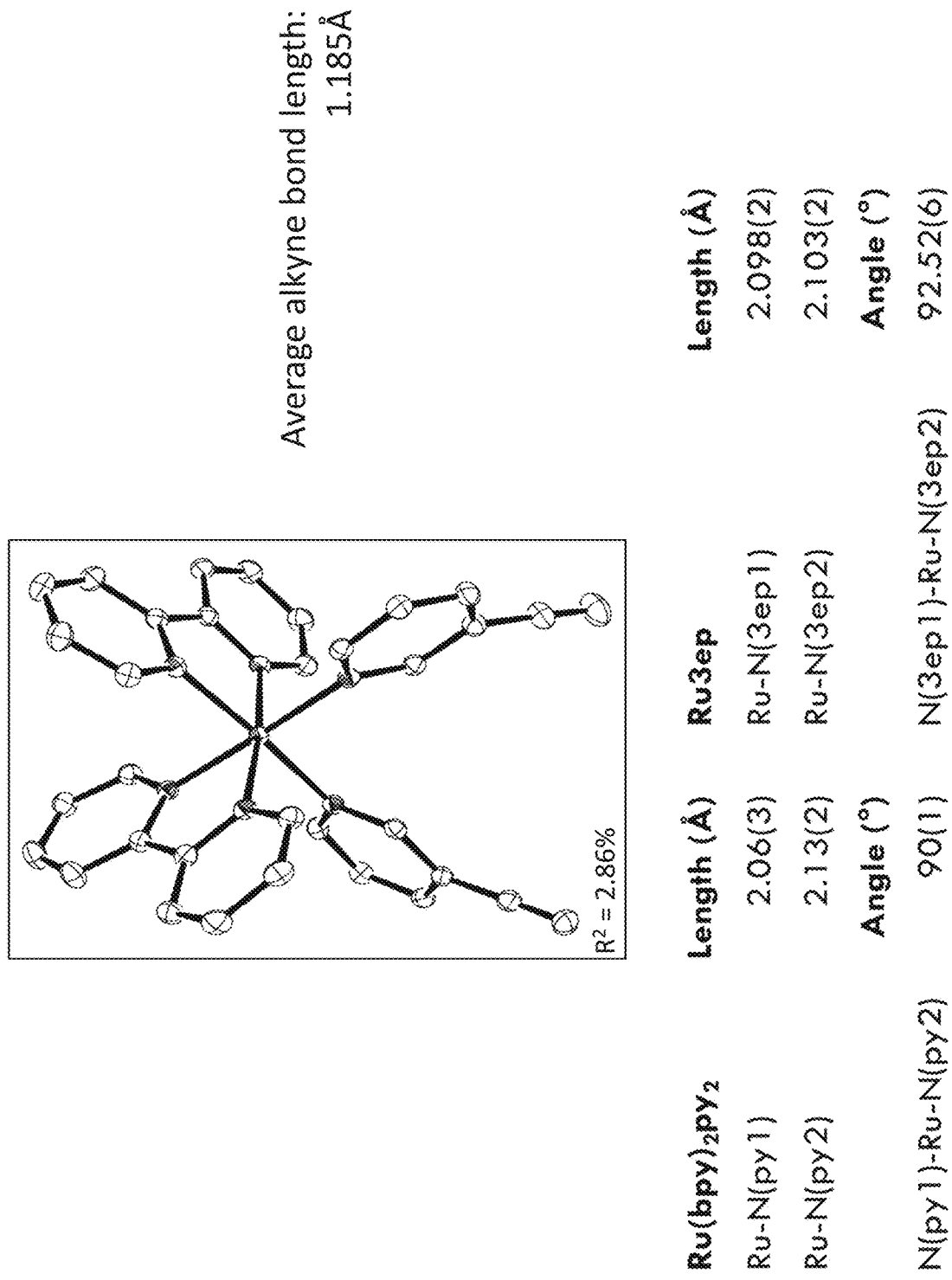
FIG. 7 is an image depicting the crystal structure of RuBEP.

Many studies have shown that phosphorylation of CREB on Ser133 induces the activation of many genes. In mice these studies have been whole tissue experiments, with little single-cell resolution and in genetic models where CREB has been knocked out in the whole animal throughout development. To assess the specific influence of CREB gene transcription activated by phosphorylation of Ser133 upon gene expression we will utilize the newly available CREB knock-in S133A mouse (CREB$^{fl/fl}$/CamKII-CRE). This is a fox conditional where the recombination event is induced by the expression of Cre-recombinase, which studies presented herein is driven by the CamKII promoter. The CamKII promoter has been used to drive the expression of transgenes in hippocampal pyramidal cells and in the CNS it is neuronal selective. In this manner, the knock-in is induced primarily in hippocampal neurons. This has the advantage over the straight knockout mouse of not inducing increases in the expression of other co-modulators that interact with CREB such as CREM. Therefore the difference in genes modulated by this Knock-in versus Wildtype will more accurately reflect the genes that are responsive to phosphorylation of CREB Ser133. Further, the TIVA experiments are done on single cells in the live slice preparation so that the important contribution of the microenvironment is captured, as demonstrated gene expression variation data (FIG. 6).

CREB Experiments

Neonates from CREB$^{fl/fl}$/CamKII-CRE+(CREB S133A produced) or CREB$^{fl/fl}$/CamKII-CRE− (WT CREB produced) are sacrificed on developmental day P1, the brains are removed and sliced into 350-μm thick coronal sections making the anatomy of the hippocampus visible. For the initial experiments, a single Ru-TIVA-tag is incubated with the slices for 60 min to ensure complete loading into cells. Intracellular Cy3/Cy5 FRET fluorescence of the TIVA-tag is easily discernible under a fluorescent scope, which confirms cell loading, and that the compound is intact. Ru-TIVA is photoactivated in individual cells by 2-P microscope under basal culturing conditions. In parallel experiments, the same procedure is undertaken in the same strain of mice that have not been induced to change CREB amino acid sequence so normal CREB protein is made. This WT control is ideal because the control and experimental mice have the same genetic background, therefore eliminating any influence such a difference would cause. Under these basal unstimulated conditions few differences in expression between the controls and the S133A animals is expected. Any differences that are apparent and not due to standard biological variation in mRNA expression between cells would be due to whatever small amount of activated transcription is part of basal transcription. The presence of the knock-in mutation is confirmed by PCR.

Next, to assess the genes whose expression is directly modulated by stimulated CREB, the slice is bathed with glutamate which through activation of metabotropic glutamate receptors stimulates phosphorylation of S133 and activates the CREB signalling pathway. Difference between the S133A mutant and WT highlight those genes that are directly activated by Ser133 phosphorylation of CREB: in the mutant the direct CREB transcription cannot be activated, whereas the other CREB functions and interactions remain intact.

The Ru-TIVA-tag is employed as it can be used to isolate mRNA populations for different cells in the slice tissue at different times after glutamate addition. Time points of 0, 30 min and 2 h post-glutamate addition to the slice are assessed. At least 10 cells from each slice at each time point is required to assess CREB mediated changes in gene expression as compared to normal single-cell variability. All cells are aRNA amplified (Phillips et al., Methods 1996, 10, 283) and a subset based upon the Bioanalyzer traces (used to assess the quality of the cellular RNA) is selected for NextGen sequencing.

The total number of sequencing reactions needed for the studies is 120 (RNA from 60 cells for WT animals: 15 cells, no treatment; 15 cells each at 0, 30 min and 2 h after glutamate treatment; 60 cells for S133A knock-in, same conditions). RNA sequencing is carried out with the two upgraded Illumina Hiseq 2500 systems available in the Penn Genome Frontiers Institute. The Hiseq system can generate one billion reads, pair-end 100 bp, over 16 sequencing lanes with the potential for bar-coded multiplexing. Each lane yields 300 million reads. A Pareto plot from sequencing data suggests that with 30 million reads, at least 45 read counts can be obtained for the ~12,000th highest expressed gene (out of 18,000 mapped genes). Thus, conservatively, a full Hiseq 2500 run allows for obtaining robust dynamic range for 96% of expressed genes for 12 samples with 10 cells/lane.

All cells employed in this study are derived from mice with a reference genome available in Genbank, thus mapping the sequences back to the genome is straightforward. Multiple algorithms are available for short sequence mapping. Recently, the RUM program (Grant et al., Bioinformatics 2011, 27, 2518. 63) greatly enhances mapping coverage and we modified the program to take into account possible artifacts introduced by the single-cell RNA amplification procedure. After sequence mapping there are many considerations for read quantification, including normalization biases, and best-practice methods at time of data collection are employed.

The experimental protocol is validated initially using a single Ru-TIVA-tag, as in a typical brain slice roughly six individual cells can be TIVA-photoactivated by 2-P microscopy, and separately harvested by pipette to allow separate RNA isolation and analysis. Ru-TIVA neuron delivery and photoactivation procedures are refined to allow maximum uncaging flexibility, with minimal crosstalk in photoactivation and RNA harvesting. The longitudinal studies for multiplexing several different Ru-TIVA-tags in intact tissues allow unprecedented insight into how CREB modulates cellular transcription and function in tissue where the cell's natural microenvironment is intact. These data will guide development of future studies to assess the role of selected Ser133 CREB-modulated genes in the signalling pathways for distinct physiologies such as addiction, learning and memory.

The experiments presented herein lead to a cohort of several different Ru-TIVA—that are distinctly photoactivatable using either a combination of 1-P (Vis, near-IR) and 2-P excitation, or exclusively 2-P excitation. This will permit multiplex TIVA compounds in the same tissue so that multiple cells, corresponding to the number of different uncaging groups, can be simultaneously or iteratively analyzed from the same tissue, therefore facilitating the analysis of a larger number of individual cells as a function of physiological stimulation. An experiment involving RNA harvesting from 3 neighboring cells would require 3 different TIVA-tags (with 3 different caging groups and 3 affinity tags). For example, an assay may comprise activation of $[Ru(bpy)_2(NCS^*)_2]^{2+}$-TIVA (2-P at 1050 nm) in cell 1, $[Ru(bpy)_2(3\text{-}EP)_2]^{2+}$-TIVA (2-P at 950 nm) in cell 2, and, finally, $[Ru(bpy)_2(MeSPh^*)_2]^{2+}$-TIVA or nb-TIVA (2-P at 800 nm) in cell 3. Validation of nb-TIVA for RNA harvesting in live brain tissue, successful Ru photolinker synthesis, and demonstration of Ru-oligo cyclization and in vivo photoactivation provide a very strong foundation for this work.

Example 4: Ru TIVA Synthesis and Characterization

Figure 8:
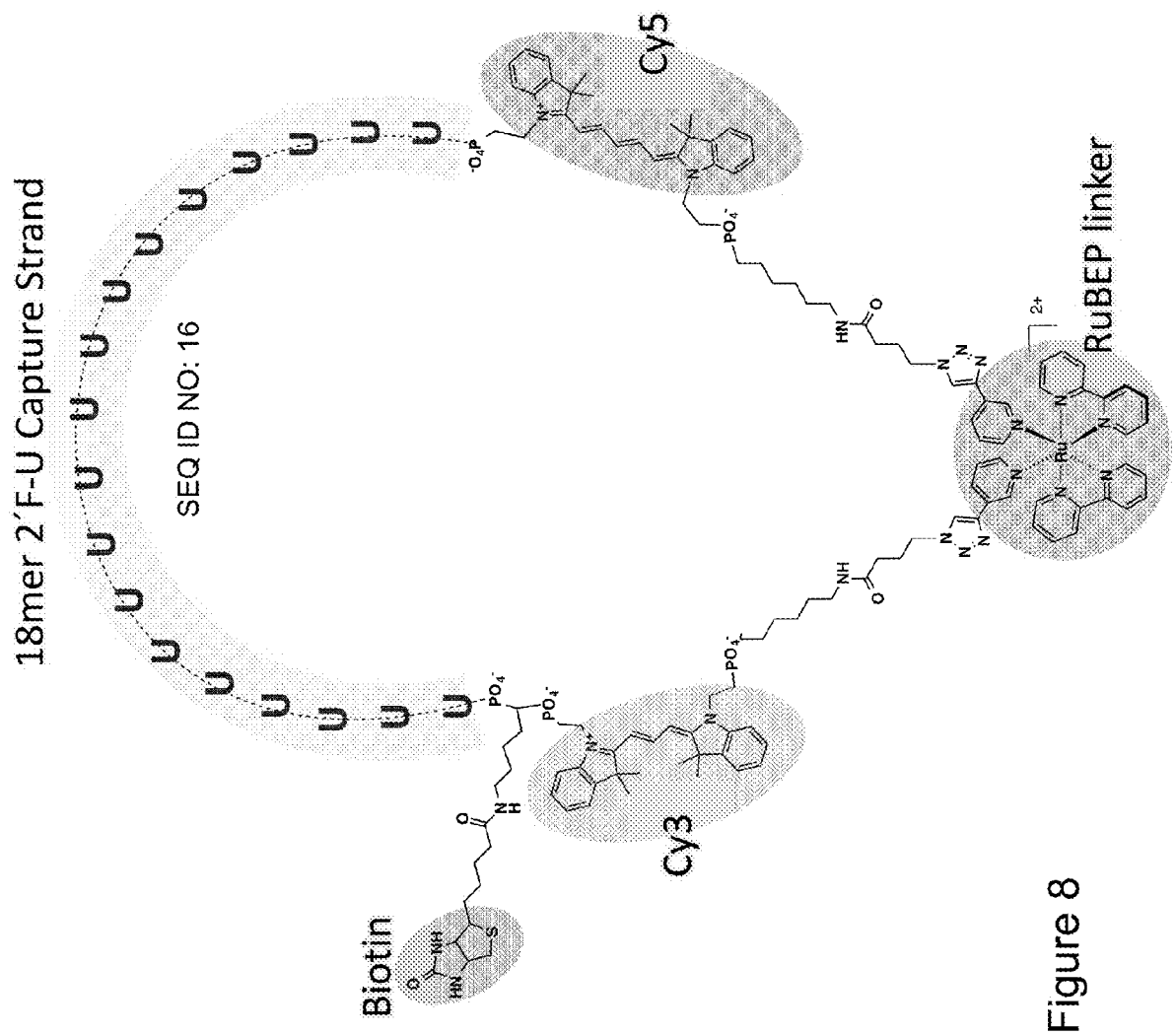
FIG. 8 is an illustration depicting an exemplary Ru-TIVA tag molecule.

Described herein is the synthesis and characterization of an exemplary Ru-TIVA-tag. An exemplary Ru-TIVA tag is depicted in FIG. 8. The depicted Ru-TIVA tag comprises an 18mer 2'F-U capture strand which binds to mRNA's poly-A tail, "tagging" it upon Ru-TIVA tag photoactivation; a biotin label which allows for isolation of tagged mRNA using streptavidin beads; Cy3 and Cy5 which is a FRET pair that acts as a reporter for Ru-TIVA tag uptake, localization, and caging condition; and the RuBEP linker, which exchanges one of its pyridyl-triazole ligands with bulk solvent upon single photon or 2-photon excitation opening the circle to reveal the 18mer 2'F-U capture strand.

Figure 9:
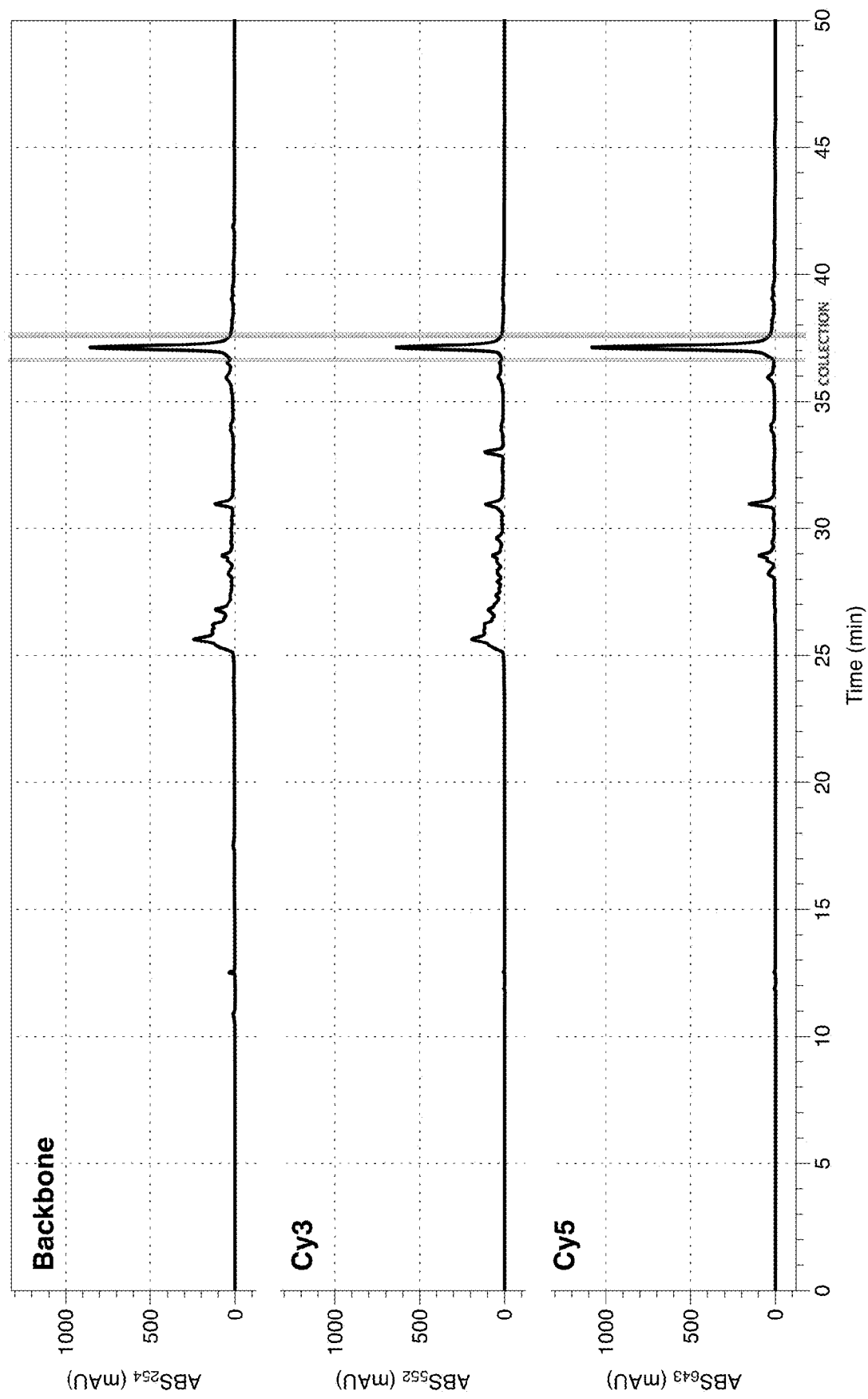
FIG. 9 is a set of graphs depicting the results of a HPLC run, monitored by the UV-Vis detector at to verify the presence of the oligo backbone, 552 nm for Cy3, and 643 nm for Cy5. The red lines show the approximate bounds of the product fraction collected.

The first step of Ru-TIVA tag synthesis was to construct the oligonucleotide backbone on solid support using standard cyanoethyl phosphoramidite chemistry. After cleavage from the support the product was purified by RP-HPLC on a C18 column. The 5' end of the successfully completed oligo was still capped by a hydrophobic DMS(O)MT group, which gave the product its late retention time (~36 minutes). The HPLC run was monitored by the UV-Vis detector at 254 nm to verify the presence of the oligo backbone, 552 nm for Cy3, and 643 nm for Cy5 (FIG. 9). The red lines show the approximate bounds of the product fraction collected.

Figure 10:
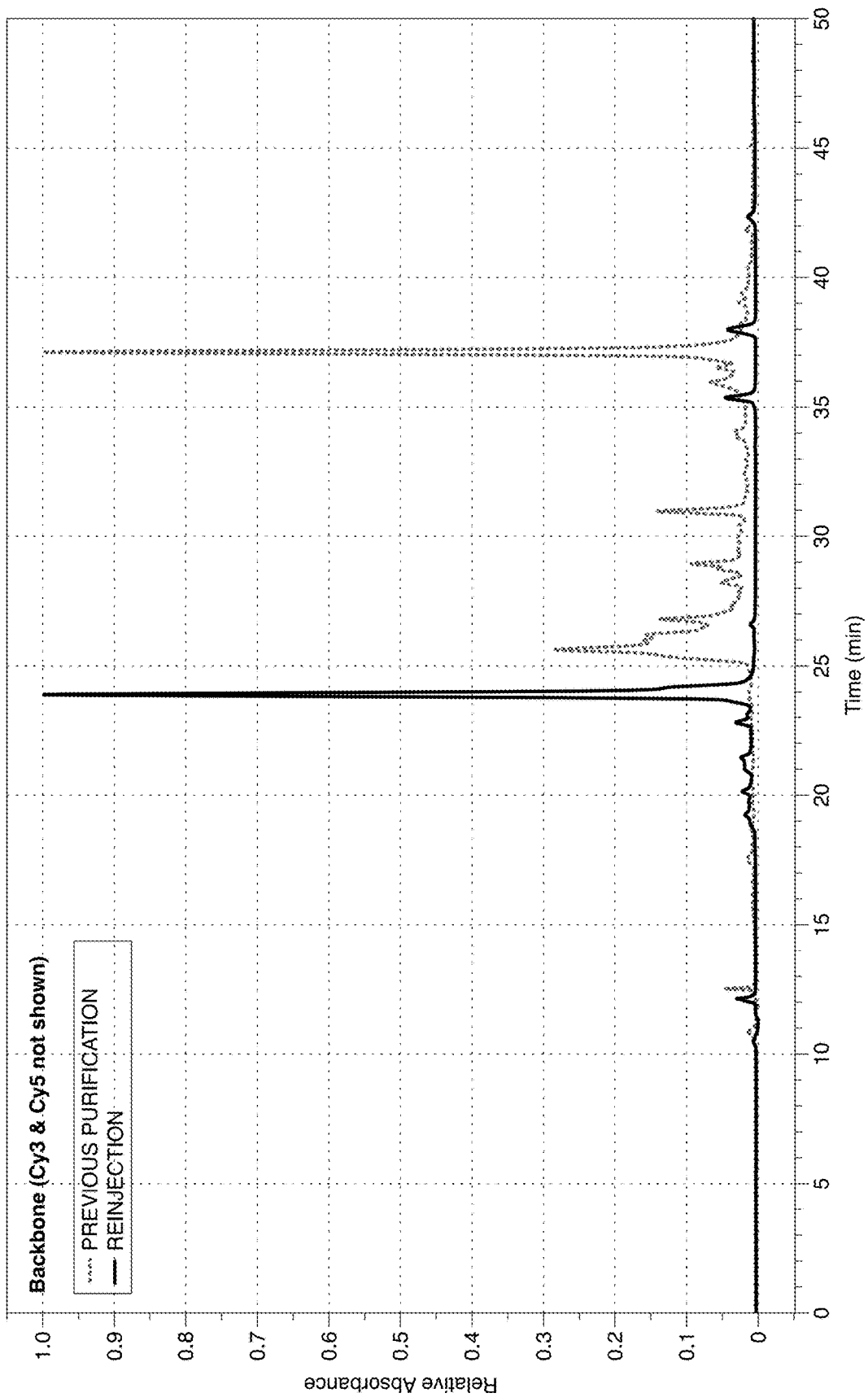
FIG. 10 is a graph depicting the loss of the DMS(O)MT protecting group.

The DMS(O)MT protecting group, used in the previous purification to help isolate the product, had to be removed. Ordinarily this is accomplished with a 1 hour, 20% acetic acid treatment, but in all syntheses to date the highly labile DMS(O)MT group has fallen off during vacufuge concentration after the previous HPLC purification, and has subsequently been permanently removed from solution using a NAP-5 column. Note the shift in retention time from ~36 minutes to ~24 minutes upon loss of the hydrophobic DMS(O)MT group, seen when the product peak is reinjected (FIG. 10).

Figure 11:
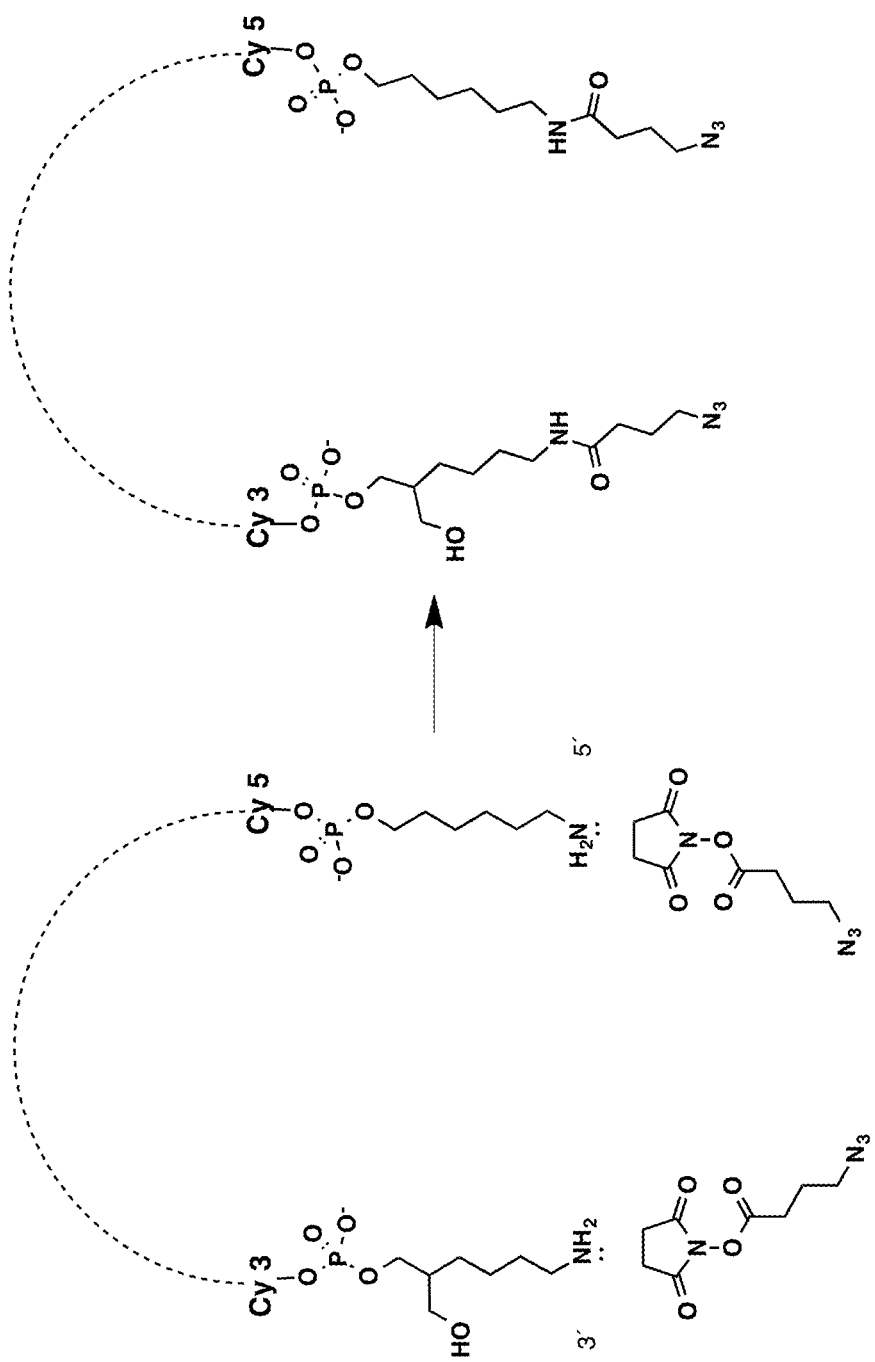
FIG. 11 is an illustration depicting the azide labeling of the two ends of the bisamino backbone to produce the bisazido backbone.

Deprotected, purified bisamino backbone at 400 µM in 0.1 M bicarbonate buffer was reacted with 20 eq of azidobutyrate NHS ester (10 eq per amine) for 2 hours at room temperature to produce the bisazido backbone (FIG. 11), which was desalted through a Nap-5 column. Expected mass 7,680, actual mass 7,700.6 found by MALDI-MS, corresponding to the backbone with one Na$^+$ counter ion (7,700.2 MW).

Figure 12:
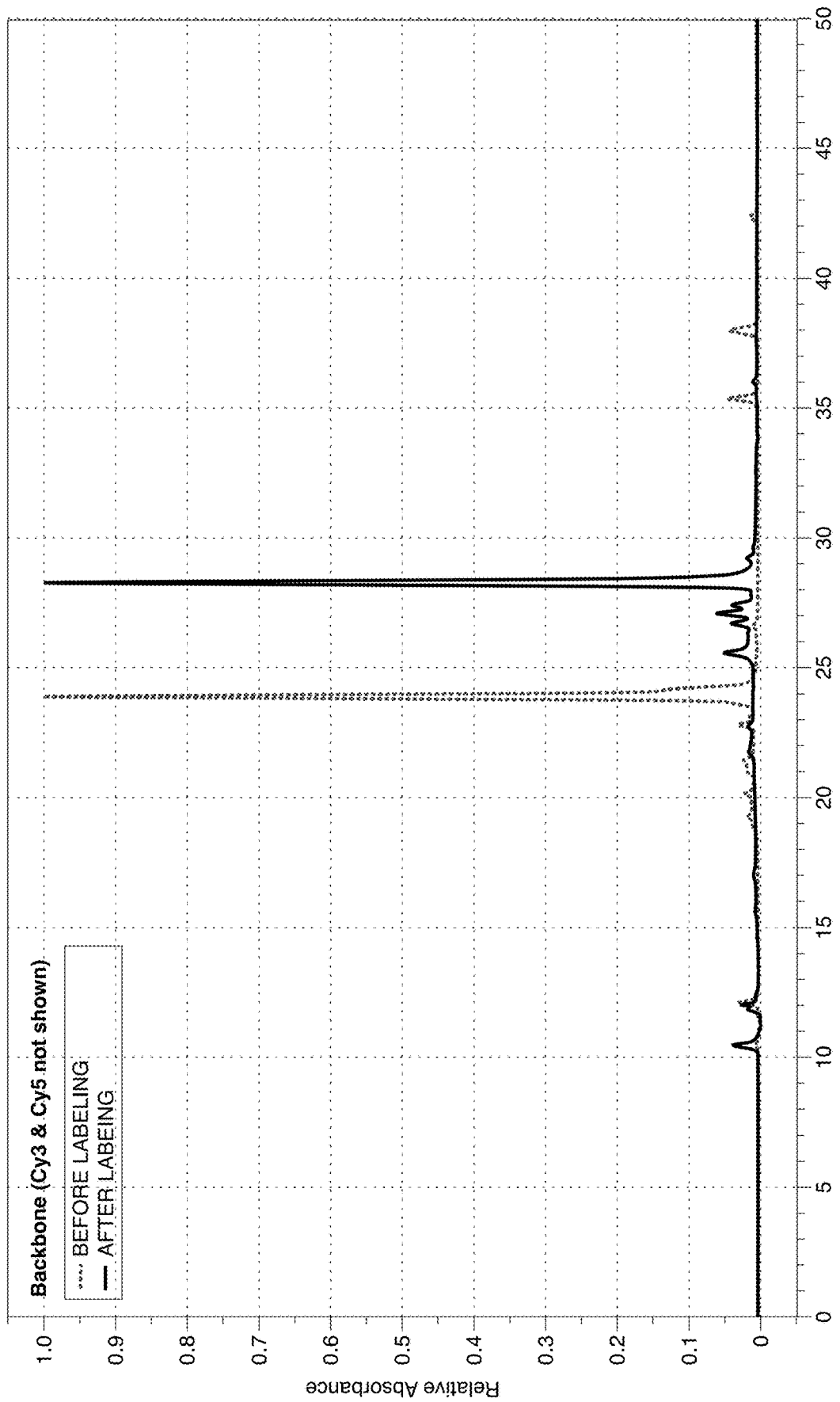
FIG. 12 is a graph illustrating the verification of azidification of the 5' and 3' ends by RP-HPLC.

The azidification of the 5' and 3' ends was verified by RP-HPLC. The shift in retention time from ~24 minutes to ~28 minutes correlates with the three methylenes added to each end from the azidobutyrate (FIG. 12).

Figure 13:
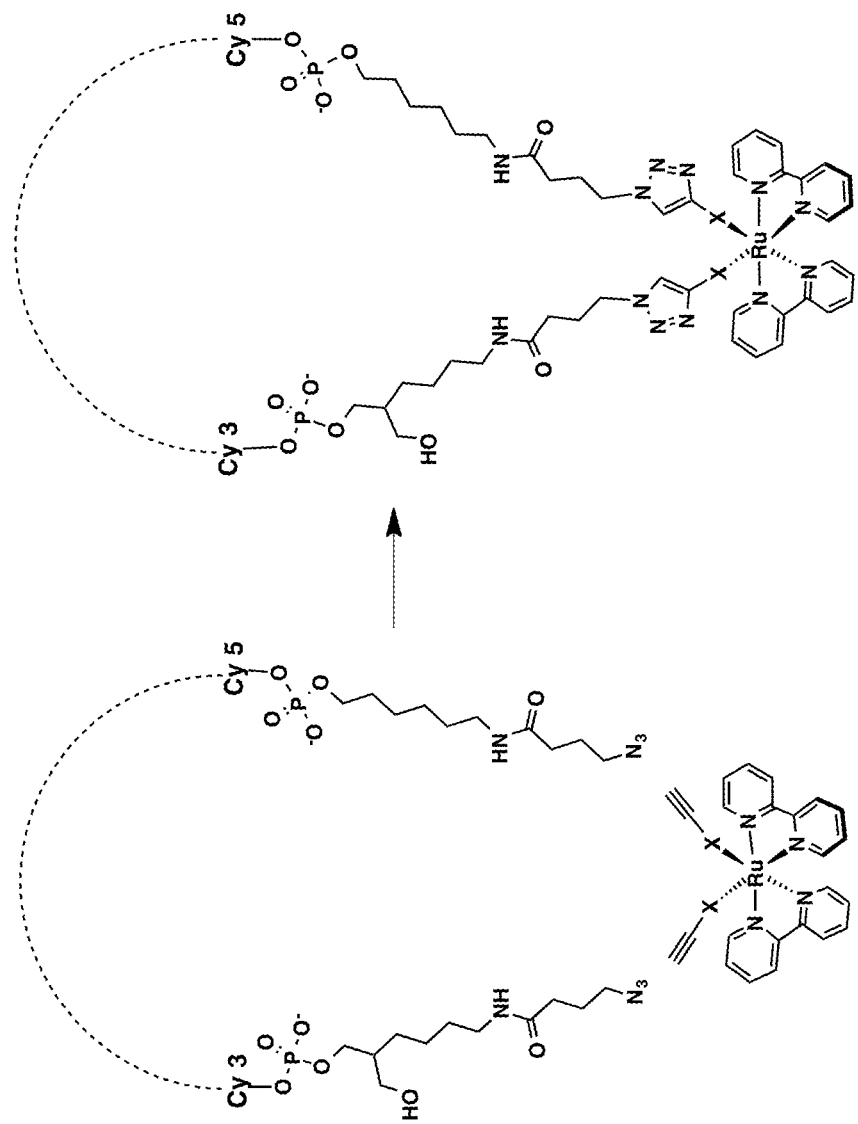
FIG. 13 is an illustration depicting the click reaction of the bisazido backbone to the RuBEP linker.
Figure 14:
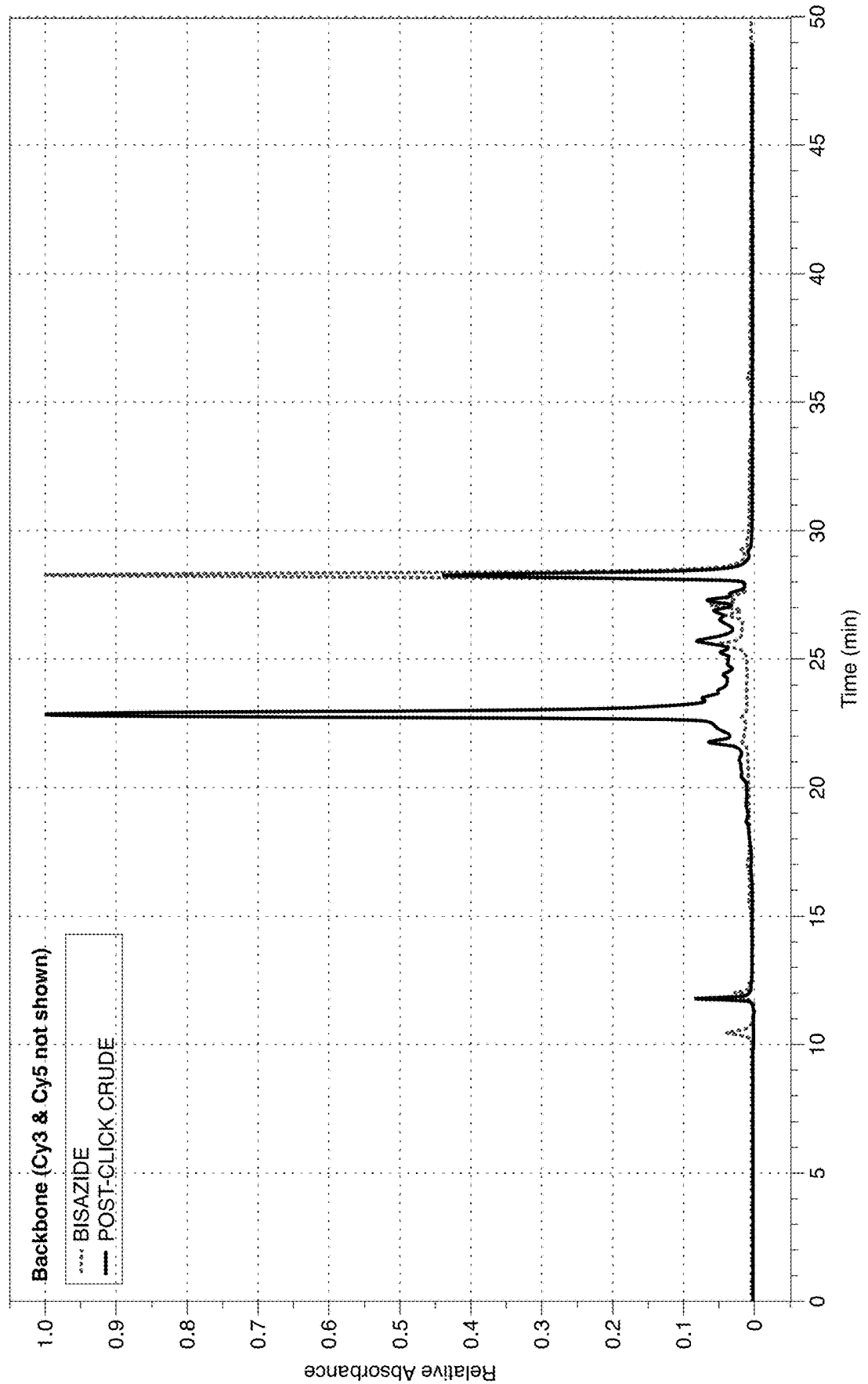
FIG. 14 is a graph depicting the results of RP-HPLC after the click reaction.

A click reaction is performed to conjugate the bisazido backbone to the RuBEP linker (FIG. 13). The reaction was performed by combining the reagents (5 nmol bisazido backbone, 0.83× eq RuBEP linker, 10× eq CuSO4, 100× eq THPTA ligand, 400× eq sodium ascorbate, and 8,000× eq Tris-HCl buffer (pH 7.5), final solution 50 µl at 20 mM). The solution is vortexed briefly and sparged with nitrogen. The solution was incubated at room temperature for 1 hour. The solution was then diluted 20× to quench and then desalted through a NAP-5 column. Finally, the RP-HPLC was used to purify. After the click reaction some of the excess starting material was still present, eluting at ~28 minutes. The circular product was collected at ~23 minutes. The red lines show the approximate bounds of the product fraction collected (FIG. 14).

Figure 15:
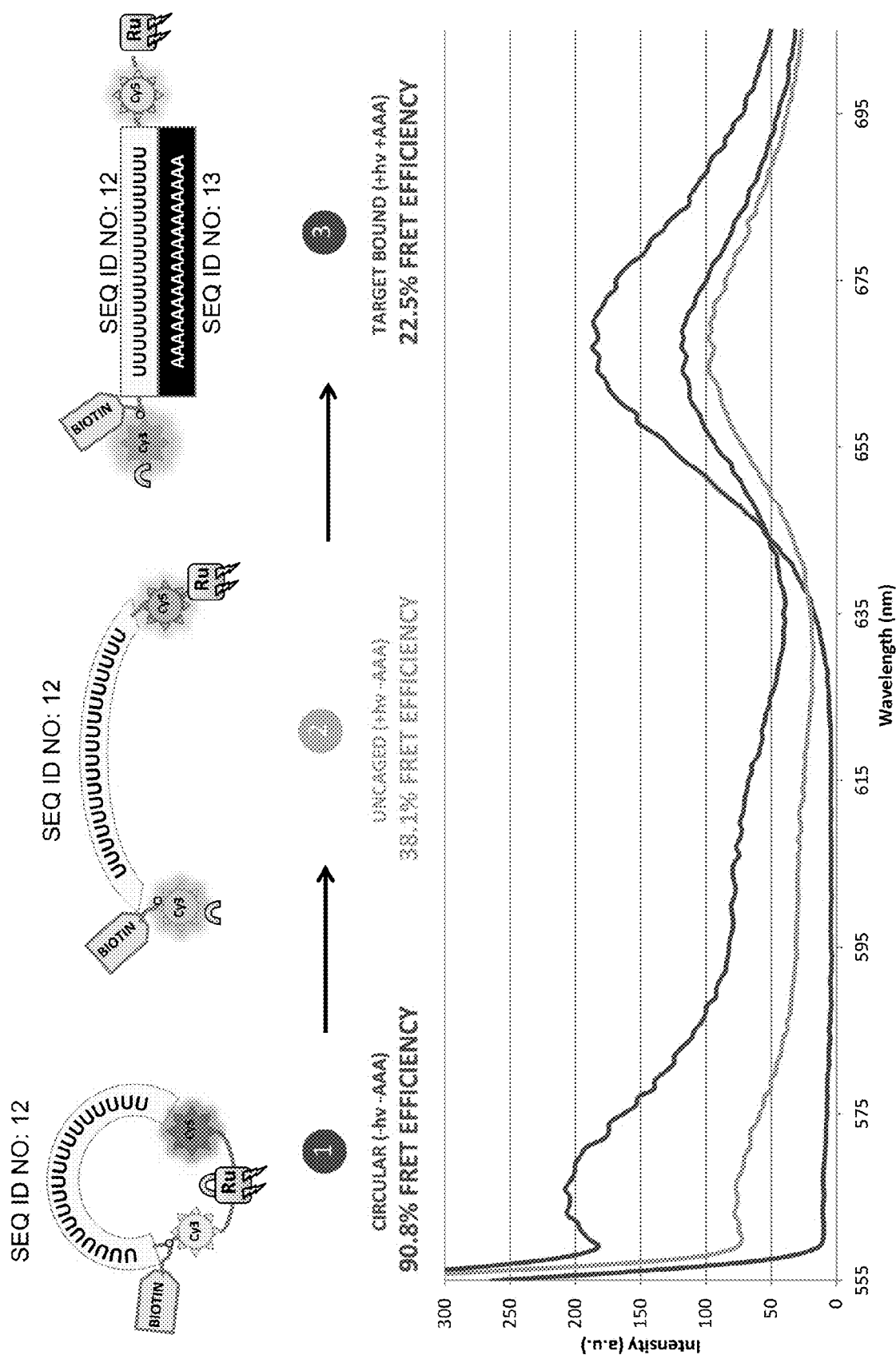
FIG. 15 is a graph illustrating the change in FRET efficiency of the circular Ru-TIVA-tag upon uncaging and upon binding of a target.

Experiments were conducted to characterize the Cy3-Cy5 FRET efficiency of the produced Ru-TIVA tag. The high FRET efficiency of the isolated product (90.8%) suggests that the Cy3 and Cy5 are held in close proximity by circularization (FIG. 15). Upon irradiating the product with a 552 nm LED for 2 minutes, the FRET efficiency drops considerably (38.1%), and is further decreased upon binding to a 25mer RNA poly-A target (22.5%).

Figure 16:
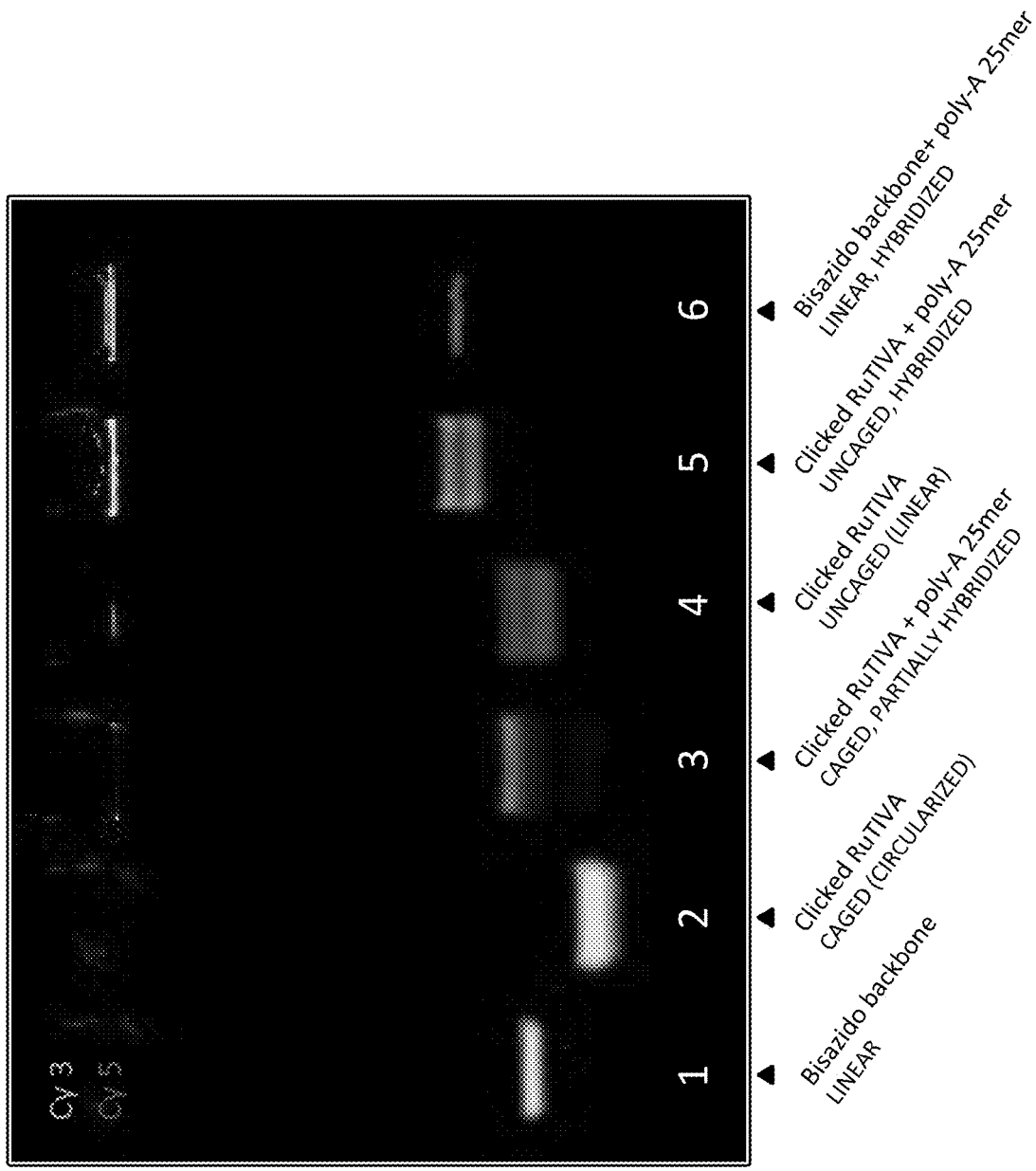
FIG. 16 is an image of a gel depicting the results of a Ru-TIVA gel-shift assay.

A 15% native PAGE gel shift assay was conducted to examine the changing migration of the Ru-TIVA tag (FIG. 16). After circularization, the product band exhibits increased Cy5 emission relative to Cy3 in agreement with previous fluorimeter data and migrates further (lane 2). Though sterically caged, the circular compound can still exhibit a temperature-dependent association with short poly-A sequences, causing a decrease in migration distance. Upon irradiation, two bands appear (lane 4), which straddle the original bisazido backbone distance (lane 1). These two bands are likely caused by the RuBEP's 50:50 release of either the 3' or 5' pyridyl-triazole upon irradiation. Both bands exhibit decreased migration distance upon hybridizing to a 25mer RNA poly-A target (lane 5), and travel similarly to the bisazido backbone+ poly-A target control (lane 6).

Example 5: Total Nuclear and Cytoplasmic RNA Detection System

Figure 17:
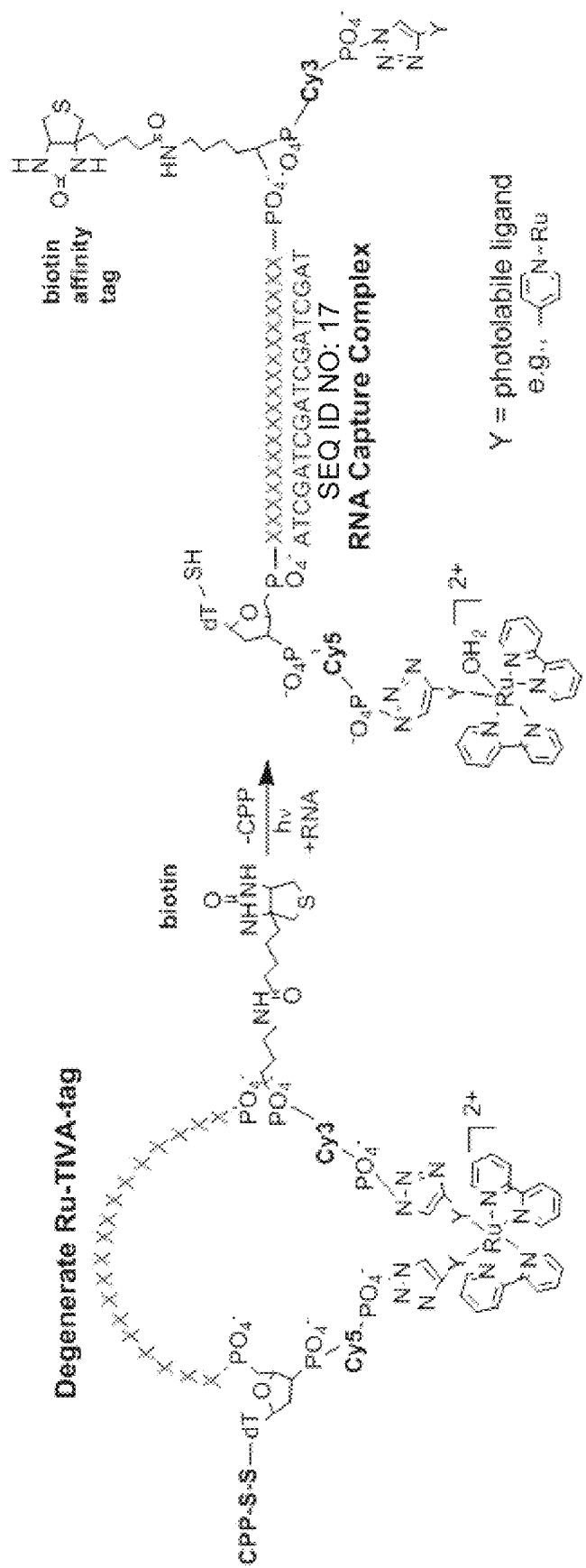
FIG. 17 is a schematic illustrating that degenerate circular Ru-TIVA captures total RNA in cytoplasm or nucleus upon 2-photon activation. The degenerate 2'F-RNA capture strand is shown in red, where X=A, U, C, or G; one of many possible target RNA sequences is shown in blue. Key features are labeled but phosphorothioated backbone is not shown. Solid-phase synthesis is performed with a stoichiometric mixture of nucleotides, with standard deprotection and coupling steps for the addition of each nucleotide. Degenerate oligos are cleaved from solid support and readily purified together by reverse-phase HPLC, as all complete sequences (e.g., ~$4^{18}$ different 18mers) will exhibit similar retention times.

Described herein is the development of TIVA probes with a very large number of different capture strands that will anneal to all RNAs, including miRNAs, long noncoding RNAs, LincRNAs and poly-A+ RNAs. These probes employ either an inorganic Ru photolinker (FIG. 17) or organic nitrobenzyl photolinker. The probe is selectively photoactivated in either the nucleus (TIVA-nuc) or cytoplasm (TIVA-cyt) by assigning a microscopic region-of-interest. The Cy3-Cy5 FRET reporter system works in cells and tissues to report on TIVA-tag photocleavage where a nitrobenzyl moiety is used as the photolinker. For the Ru-photolinkers, in certain instances, Cy5-Cy5.5 FRET pair can be used such that imaging can be performed (1-P $\lambda_{ex}$>600 nm), without unintended photoactivation. All TIVA-tags synthesized to date are non-toxic to neurons when rigorously purified by analytical HPLC, followed by dialysis to remove organic solvents and metal salts.

mRNA Vs. Total RNA or Specific RNAs.

TIVA-cyt has been used to capture mRNA from the cytoplasm of individual neurons, by targeting the poly-A tail. Experiments are also now designed to collecting total RNA, using degenerate probes. And, in certain cases, it will be most useful to design probes with unique sequences that select very specific RNAs. All 3 types of capture strands are employed for TIVA-cyt and TIVA-nuc, and used for cross-referencing purposes.

TIVA-cyt

To allow for more focal uncaging experiments at greater tissue depth, a new TIVA architecture is designed where the two ends of the oligonucleotide are joined into a circle, while incorporating a single ruthenium-based photolinker. Advantages of the circular design are its minimalist structure, the potential for higher RNA capture efficiency (without blocking strands), and the need for only 1 photocleavable linker, which improves uncaging efficiency and also facilitates incorporation of a 2-photon-activatable caging moiety.

TIVA-nuc.

Figure 18:
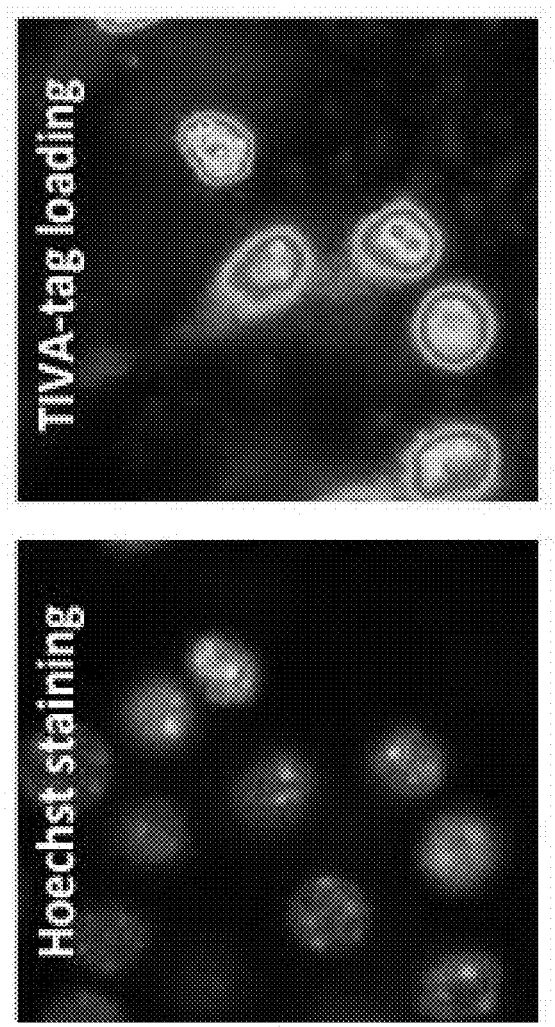
FIG. 18 is a set of images depicting the nuclear localization of $Arg_9$-TIVA-tag in pyramidal neurons of acutely cultured mouse hippocampal slices.

The development of TIVA-tag to selectively isolate nuclear RNA (TIVA-nuc) mirrors that of TIVA-cyt but promises to highlight those genes that are rapidly turned on in response to particular stimuli. The TIVA-tag with Arg$_9$ cell-penetrating peptide gains ready access to the nucleus, as evidenced by accumulated Cy3 fluorescence signal (FIG. 18). Thus, TIVA-nuc can be selectively uncaged in the nucleus of the cell, which will enable isolation of the nuclear compartmentalized RNA independently of the cytoplasmic RNA population. Because many of the RNA molecules in the nucleus do not contain a poly-A tail, TIVA-nuc, in particular, will be designed with 2'F-RNA capture strand containing all possible degenerate sequences (with A, U, C, or G at every position, see FIG. 17).

As mRNA splicing occurs predominantly in the nucleus of the cell and the first nuclear transcripts to be synthesized are heteronuclear RNAs (hnRNAs), it is anticipated that TIVA-nuc-enriched RNAs will contain many more introns then cytoplasmic mRNA thereby permitting us to assess the extent of hnRNA capture by TIVA-nuc. Having a good metric for assessing the success of nuclear RNA harvesting will permit us to optimize the TIVA-nuc procedure. The success of this procedure would provide a morphologically defined in vivo correlate of ChIP-Seq. Such data would be free of the cytoplasmic mRNA complication that steady-state levels of mRNA are a balance between mRNA transcription and degradation: TIVA-nuc should primarily identify transcription.

Ru-Linkers.

To expand the functionality of TIVA for in vivo studies, a 1-P-visible and 2-P (near-IR) activatable linker, Ru(bpy)$_2$(3-ethynyl-pyridine)$_2$ was developed. Gram quantities of pure material can be obtained in ~50% yield. High-resolution X-ray structure determination (FIG. 1) confirmed that the reactive ethynes are correctly oriented ($\theta_{N-Ru-N}$=92°) for ring closure. To develop procedures for Ru-oligo circularization, oligonucleotides (DNA, morpholino) terminated by azide at both 3' and 5' ends were reacted with Ru(bpy)$_2$(3-ethynyl-pyridine)$_2$ to give the desired cyclized Ru-oligo products in ~70% yield, after HPLC purification. The alkynes underwent [3+2] Cu(I)-mediated Huisgen cycloaddition reactions with the azides under oligonucleotide-compatible conditions (rt to 40° C., 1-2 days, at 1:1 stoichiometry). It has been previously reported that the azide-alkyne "click" reaction can give >90% yield of the triazole bioconjugate upon optimization (Tang, et al., 2008, Nucl. Acids Res., 36(2): 559-569; Aaron et al., 2008, J. Am. Chem. Soc., 130(22): 6942-694; Chambers et al., 2009, J. Am. Chem. Soc., 131(2): 563-569; Hill et al., 2007, J. Am. Chem. Soc., 129: 9262-9263; Hill et al., 2009, J. Am. Chem. Soc., 131(8): 3069-3077; Seward et al., 2011, Chem. Sci., 2(6): 1103-1110; Seward et al., 2008, Bioconjug. Chem., 19(11): 2129-2135). Formation of the cyclized Ru-oligo product was indicated by gel electrophoresis (imaged with ethidium bromide), and the gel also confirmed reaction of all starting azido-oligonucleotide. Irradiation of the circular Ru-oligo with visible light (450 nm) gave the expected linear photocleavage product, which ran somewhat faster on the gel. The photocleavage reaction is readily monitored in real-time by UV-Vis spectroscopy (FIG. 2), which shows clean conversion of Ru(bpy)$_2$(3-ethynyl-pyridine)$_2$ to the mono-aquo product, Ru(bpy)$_2$(3-ethynyl-pyridine)(OH$_2$), as indicated by three isosbestic points and confirmed by $^1$H 2-D NMR spectroscopy. Importantly, the Ru-oligo bioconjugation reaction is very specific for the alkyne and azide, and no side reactions are observed with the many functional groups contained on the oligonucleotide.

Multiplexing-Photolysis.

Ru-photolinkers for multiplexing experiments are being developed and are employed to cage oligos as described above for RuBEP. Briefly, Ru-caging chemistry has been explored by the Etchenique lab over the past 10 years, but has involved only a few pyridine and amine ligands using the commercially available Ru(bpy$_2$)Cl$_2$ or Ru(tpy)(bpy)Cl starting materials (Salierno et al., 2008, Eur. J. Inorg. Chem., 7: 1125-1128; Zayat et al., 2006, Inorg. Chem., 45(4): 1728-1731). Salassa and coworkers have provided spectroscopic and computational studies (Salassa et al., 2008, J. Am. Chem. Soc., 130(29):9590-9597; Salassa et al., 2009, Inorg. Chem., 48(4): 1469-1481), and more recently, Turro has explored Ru(bpy$_2$)-thioether photolysis (Garner et al., 2012, Inorg. Chem., 50: 4384-4391). By extending this Ru(bpy$_2$)X$_2$ chemistry to other X ligands, and varying the electron-donating ability of the bpy or other possible polypyridyl ligands, greater tunability of the Ru 1P- and 2P-dissociation chemistry is gained. Compounds synthesized to date show extremely high 1-P quantum yields [ε(1P, 450 nm)=6700 M$^{-1}$ cm$^{-1}$,Φ=0.33 in air, εΦ=2140 for RuBEP], and a wide range of 1-P absorption maxima, as required for multiplexing. Reported 2-P absorption cross-sections for similar Ru-bpy complexes are 0.1-1.0 GM at 800 nm, and these values are determined for each new Ru-photolinker. Critically, A "RuBi"-glutamate complex with similar ligand set to the proposed Ru linkers (Matsuzaki et al., 2010, Nature Chem. Biol., 6(4): 255-257) is commercially available and has been employed extensively for mapping neural circuits in live brain slices. These in vivo studies highlight that the chelated Ru$^{2+}$ is non-toxic in neurons, and repeated Ru photoexcitation in the soma produces no loss of neuronal function (Nikolenko et al., 2011, Cold Spring Harbor Protocols, 2011. (5): p. pdb.top111). Ru-linkers exhibit maximal 2-P uncaging between 750 and 1050 nm. Thus, Ru-TIVA-tags, combined with nb-TIVA, which can be activated with $\lambda_{2P}$=680 nm, afford the possibility to achieve spatially and temporally selective RNA capture by combining orthogonal photo-activation with selective affinity tags.

Multiplexing-Tags

Biotin is readily incorporated into TIVA by solid-phase synthesis using a 3'-biotin CPG from Glen Research. Neuronal RNA bound to TIVA-tag is pulled down using streptavidin-coated beads, and subsequently released by thermal melting. For multiplexing studies requiring additional affinity tags, the plant steroid digoxigenin (Dig), which is sold by Gene Link as the NHS ester is employed. This is covalently attached to the oligonucleotide via an active primary amine phosphoramidite (e.g., Amino Linker C6, Genelink), which is incorporated by solid-phase synthesis. Anti-Dig probes are widely available for isolation purposes. Another small hapten (MW 500 amu) is dinitrophenyl (DNP), which is available with PEG linker as the phosphoramidite from Gene Link. RNA harvesting occurs using anti-DNP antibodies (Roche) on agarose beads (Hsu et al., 2009, Nucl. Acids Res., 37(10): e77-e77). If necessary, multiple Dig or DNP affinity tags may be incorporated within TIVA to increase pull-down efficiency (Grzybowski, et al., 1993, Nucl. Acids Res., 21(8): 1705-1712). Biotin, Dig, and DNP all offer the advantage of small molecules, with minimal chance of affecting TIVA uptake, toxicity, stability, or RNA capture efficiency. A second approach involves peptide tags: FLAG-tag (DYKDDDDK (SEQ ID NO: 7)), HA-tag (YPYDVPDYA (SEQ ID NO: 8)), and Myc-tag (EQKLISEEDL (SEQ ID NO: 9)) are well recognized by antibodies (Sigma-Aldrich). The N-terminal Cys-FLAG, HA, or Myc peptides can be attached to TIVA via maleimide linker (as phosphoramidite). Yields and sequences of RNA captured will be compared for the different affinity tags, in the course of TIVA-cyt and TIVA-nuc development.

"Self-Priming" TIVA/TIVA-Extend

Figure 23:
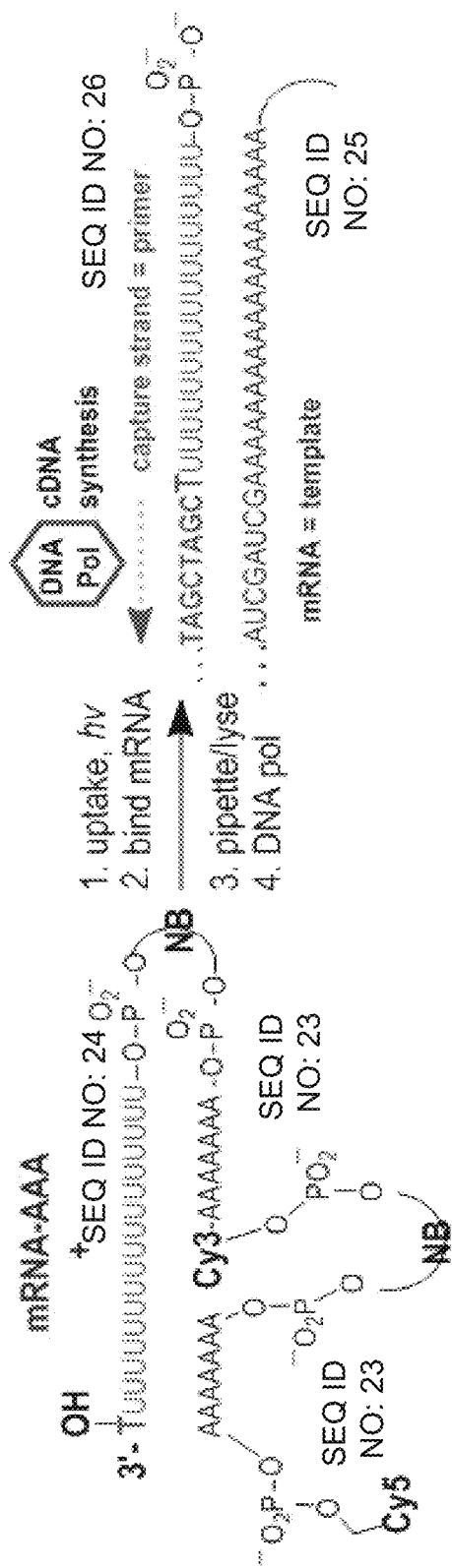
FIG. 23 is a schematic depicting the in situ synthesis of cDNA using the capture strand as the primer and the captured mRNA as the template.

Multiplexed RNA capture is also achieved by incorporating a DNA nucleotide (e.g., thymine) at the 3' end of the capture strand (FIG. 23). This "priming nucleotide" enables cDNA production by DNA polymerase directly within the cell lysate, avoiding the pull-down step and obviating the need for biotin or other tag. This TIVA concept is investigated with both the circular degenerate architecture (e.g. FIG. 17, for total RNA capture) and hairpin polyU (for mRNA capture), employing Ru or nitrobenzyl photolinkers. The synthesized cDNA can then be isolated with a polyA-column and processed through the standard linear RNA amplification methodology. This provides an even more efficient scheme for converting the target RNA into a cDNA library, and leads to higher yields of material for sequencing.

Cyt-Nuc Multiplexing Strategy

In one duplexed experimental paradigm, Biotin-Ru-circular-degenerate-TIVA-nuc (FIG. 17) is photoactivated in the nucleus (2-P $\lambda_{ex}$=800 nm), followed by nitrobenzyl-hairpin-polyU-TIVA-extend cyt (FIG. 23) activation in the cytoplasm (2-P $\lambda_{ex}$=680 nm). There will be no crosstalk between these probes because the nitrobenzyl linker is not readily cleaved at 2-P $\lambda_{ex}$>720 nm. Biotin-Ru-TIVA:nuclear RNA is harvested with streptavidin beads, followed by TIVA-extend:cytoplasmic mRNA reaction with DNA polymerase in solution. If useful, the 'affinity tagging' and 'self-priming' strategies can be combined in the same probe.

Stability and Integrity.

TIVA-tags are developed that remain completely hybridized and stable for at least 1 hour within the cellular environment, as will be particularly important for measuring the stimulated transcription in time-course studies. In the caged circular state, Ru-TIVA should bind no neuronal RNA and provide high FRET signal, with a Cy3-Cy5 distance of just 15-20 Å. Post-photolysis, the Cy3-Cy5 distance will increase to 40-60 Å for linear TIVA (FIG. 2), depending on the capture strand. The melting temperature ($T_m$) of the TIVA-RNA capture complex will be ideally >60° C., as we found important for DNA hairpin stability in previous cell and embryo experiments (Tang, et al., 2008, Nucl. Acids Res., 36(2): 559-569; Tang et al., 2007, J. Am. Chem. Soc., 129(36): p. 11000-11001).

Example 6: Capture-Stem Hybrid Ru-TIVA

Figure 19:
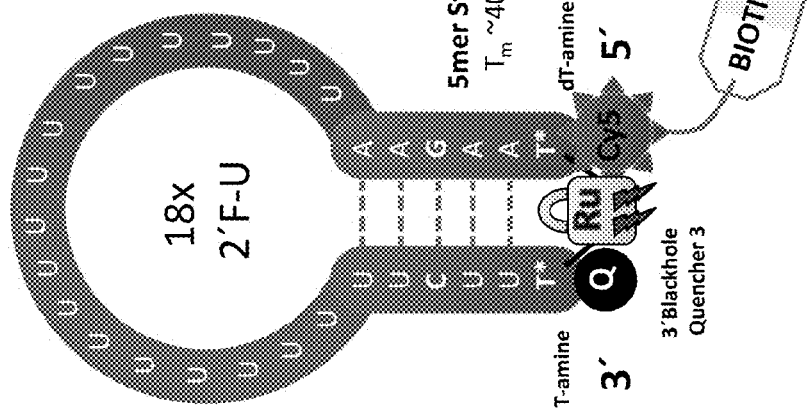
FIG. 19 depicts exemplary Ru-TIVA tags having a capture-stem hybrid conformation and a poly-2'F-U capture strand.
Figure 19:
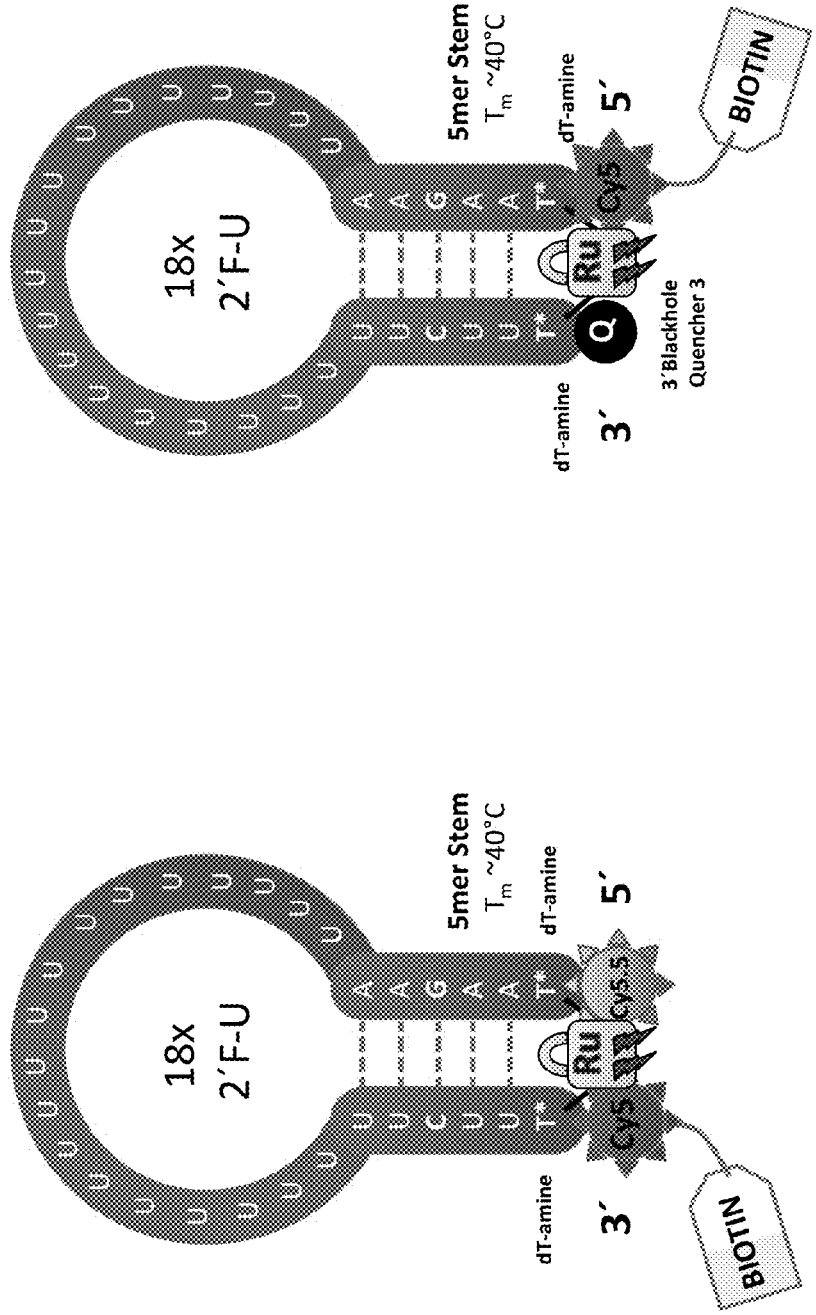
Figure 20:
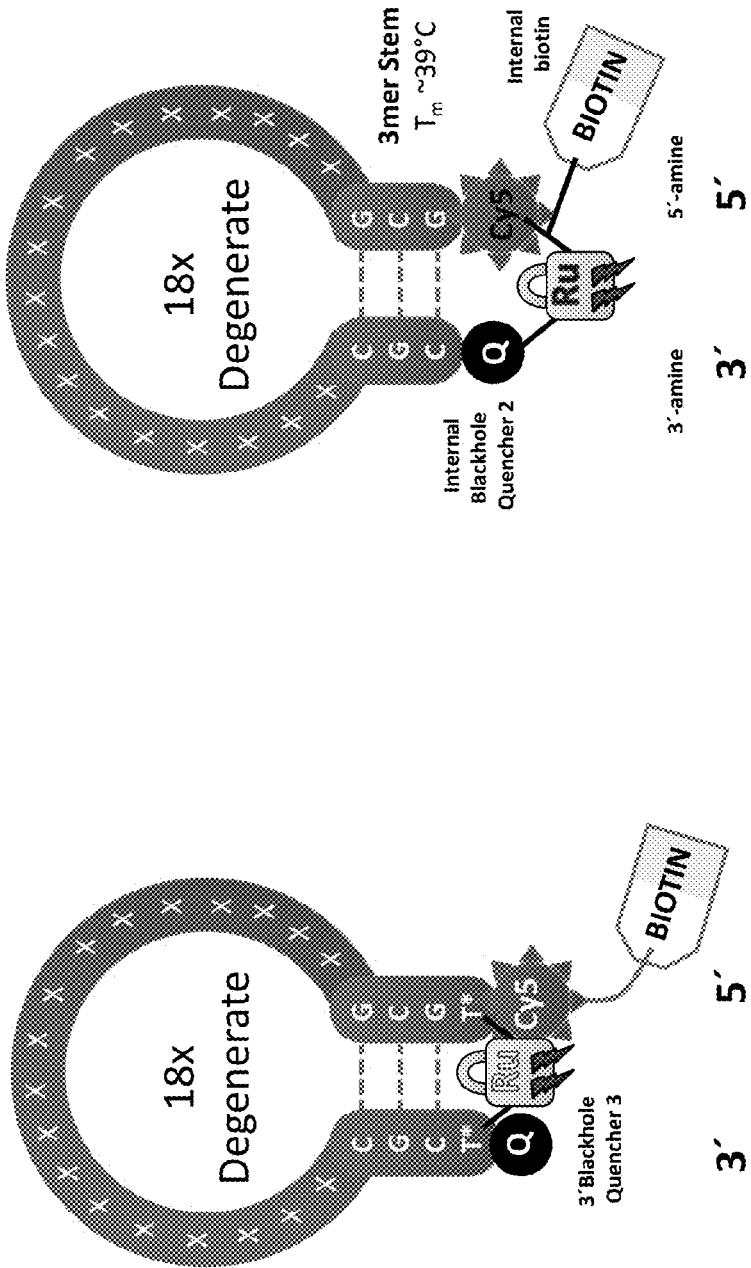
FIG. 20 depicts exemplary Ru-TIVA tags having a capture-stem hybrid conformation and a degenerate capture strand.

An alternative Ru-TIVA tag is designed where the oligonucleotide comprises a capture region and two-stem forming regions which hybridize to form a stem (FIG. 19 and FIG. 20). For example, the tags shown in FIG. 19 comprise an 18mer 2'F-U capture region and two 5mer stem forming regions on either side of the capture region. As shown in the exemplary hybrid tags in FIG. 19A and FIG. 19B, in certain instances the continuation of the polyU strand into one of the stem-forming regions may improve target binding and provide enough distance for the Cy5/Cy5.5 reporter. The oligonucleotide also comprises terminal dT-amines for linkage of the Ru-photolinker. In one exemplary hybrid tag (FIG. 19A), the tag comprises a Cy5/Cy5.5 FRET pair. In one exemplary hybrid tag (FIG. 19B), the tag comprises a dark quencher (e.g., blackhole quencher 3) and a Cy5 fluorophore. The poly-U capture region of the tags depicted in FIG. 19 allow for capture of polyA+ RNA (e.g., mRNA).

FIG. 20 depicts alternate capture-hybrid Ru-TIVA tags that comprise an oligonucleotide comprising an 18mer-degenerate sequence and two stem-forming regions. In the exemplary tags depicted in FIG. 20, the oligonucleotide comprises two 3mer stem forming regions, which hybridize together to form a stem. A plurality of these tags can then be used for TIVA-tot applications to capture all types of RNA. The exemplary tag depicted in FIG. 20A comprises an oligonucleotide having terminal dT-amines for linkage of Ru-photolinker. Such tags may be synthesized easier yielding to higher yields, but in certain instances the dT-amines may bind to the degenerate stretch of the capture region. In the tag depicted in FIG. 20B, the dT-amines are replaced with terminal amines, thereby reducing the likelihood of the stem forming region to bind to the degenerate capture region.

Figure 21:
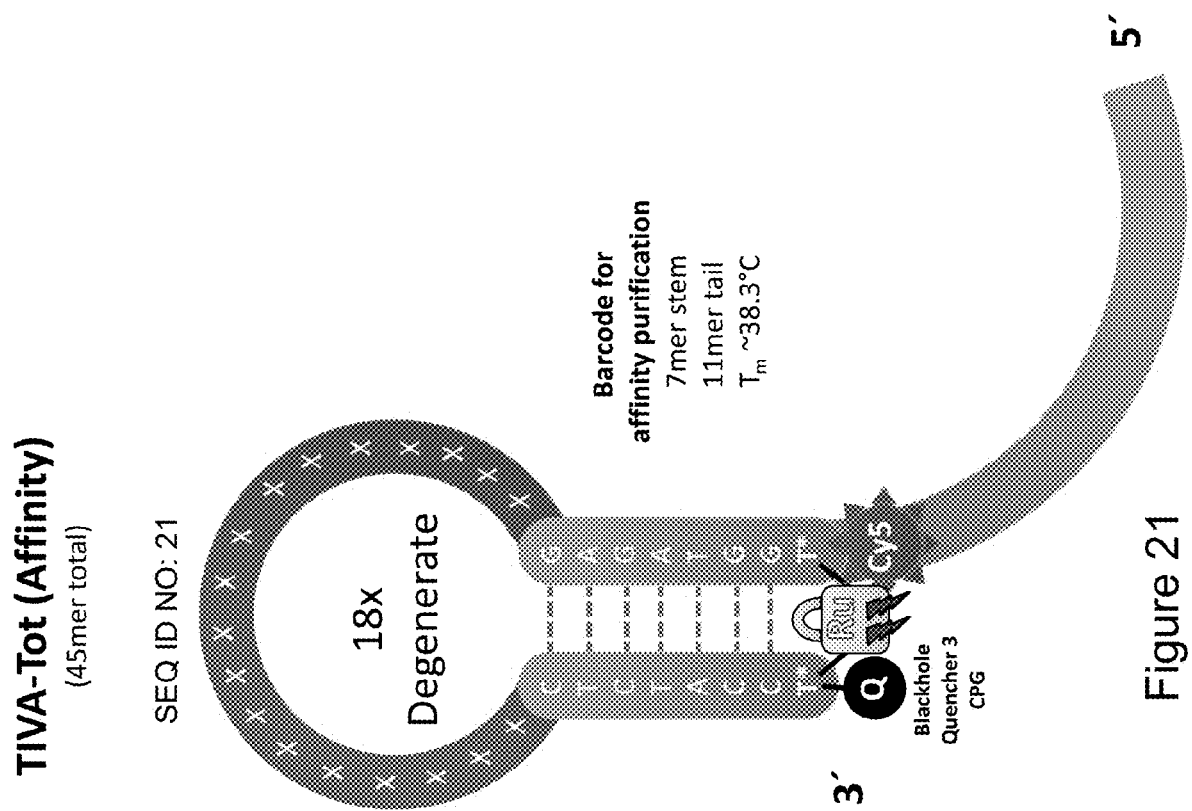
FIG. 21 depicts an exemplary Ru-TIVA tag having a capture-stem hybrid conformation and comprising a barcode affinity tag for affinity purification.

Another hybrid Ru-TIVA tag is depicted in FIG. 21, which comprises a barcode/index that can be used for affinity purification. This tag comprises a capture strand (e.g., a 18mer degenerate sequence), two stem forming regions, and a tail region. For example, the tag depicted in FIG. 21 comprises two 7mer stem forming regions and a 11mer 5' tail. In certain instances, a tag comprising a nucleotide affinity tag may be easier to synthesize than adding a biotin tag.

Example 7: Lariat Ru-TIVA

Figure 22:
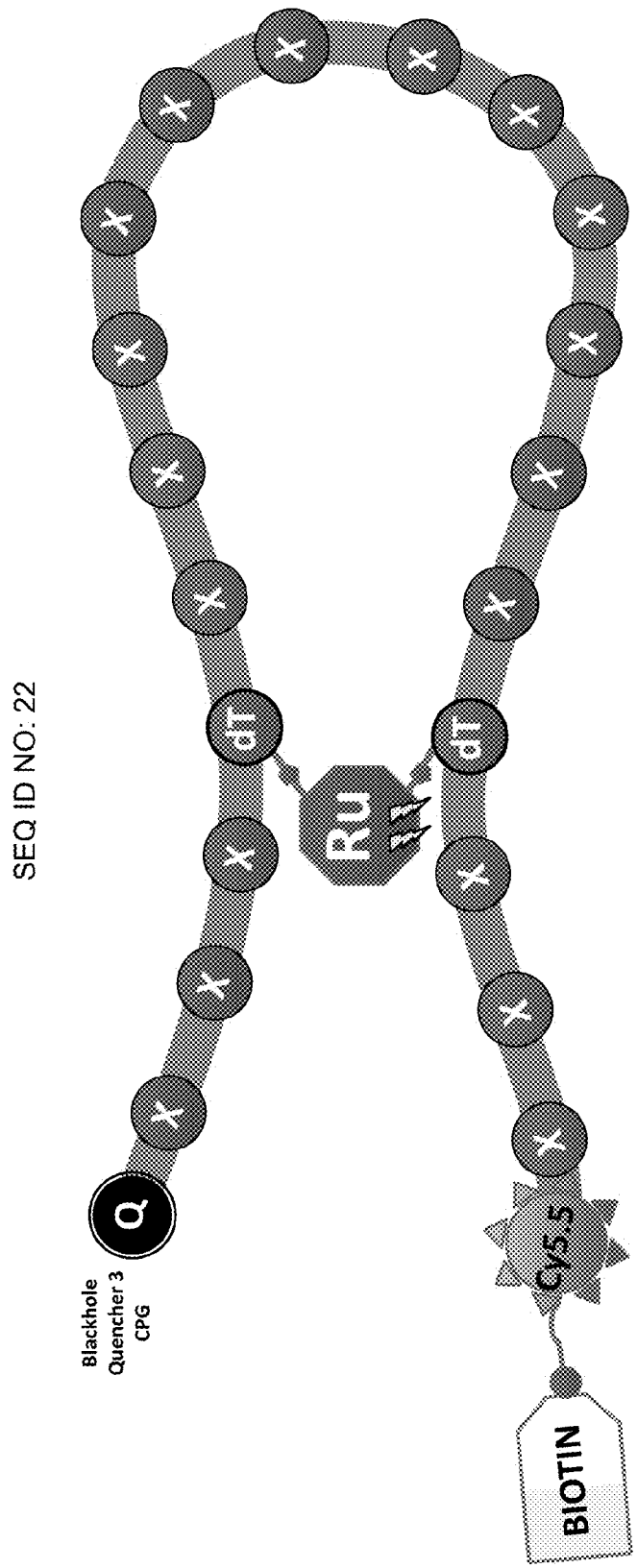
FIG. 22 depicts an exemplary Ru-TIVA tag, where the degenerate capture strand comprises two internal dT-amines for internal conjugation of the Ru-based photolinker.

A lariat Ru-TIVA tag is designed as depicted in FIG. 22. This tag comprises an oligonucleotide comprising two internal dT-amines for internal linkage of a Ru-photolinker. In certain instances, the lariat Ru-TIVA exhibits higher caging efficiency than circular constructs. The exemplary tag depicted in FIG. 22 comprises a degenerate capture strand for use in TIVA-tot applications. Alternatively, the tag may be designed with a polyU strand, having internal dT-amines, to capture polyA+ RNA.

Example 7: TISA-Tag

Exemplary TISA-tags were designed and constructed. As described elsewhere herein TISA-tags are able to bind to target RNA and through a 3' deoxynucleotide (e.g., dT) prime cDNA synthesis off the captured RNA using reverse transcriptase. The captured RNA can then be amplified using standard antisense RNA (aRNA) amplification and/or in vitro transcription techniques.

In certain instances, the TISA-tags are used for detection of target RNAs in situ, where photoactivation of an oligonucleotide that upon photoactivation will bind to the RNA in a single target cell and serve as a primer for cDNA synthesis in situ (FIG. 23). This cDNA can then be removed from the single cell, amplified, and made into a cDNA library that can be NextGen sequenced. The TISA procedure is relatively quick and high-throughput as multiple fixed single cells can be photoactivated simultaneously through the use of the incorporated molecular barcode. Importantly, TISA can be used to investigate the transcriptomes of single cells in the large bank of fixed patient or animal tissue.

Figure 24:
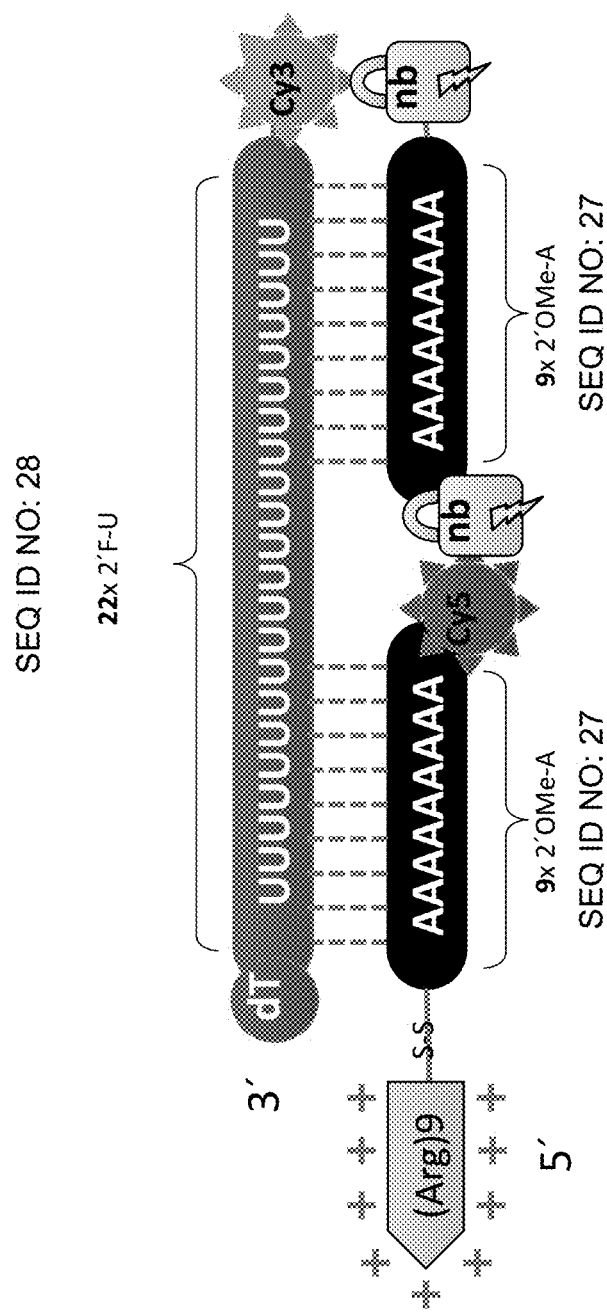
FIG. 24 depicts an exemplary TISA-tag comprising a 22mer poly-2'F-U capture strand, a terminal dT, and a (Arg)9 CPP.
Figure 25:
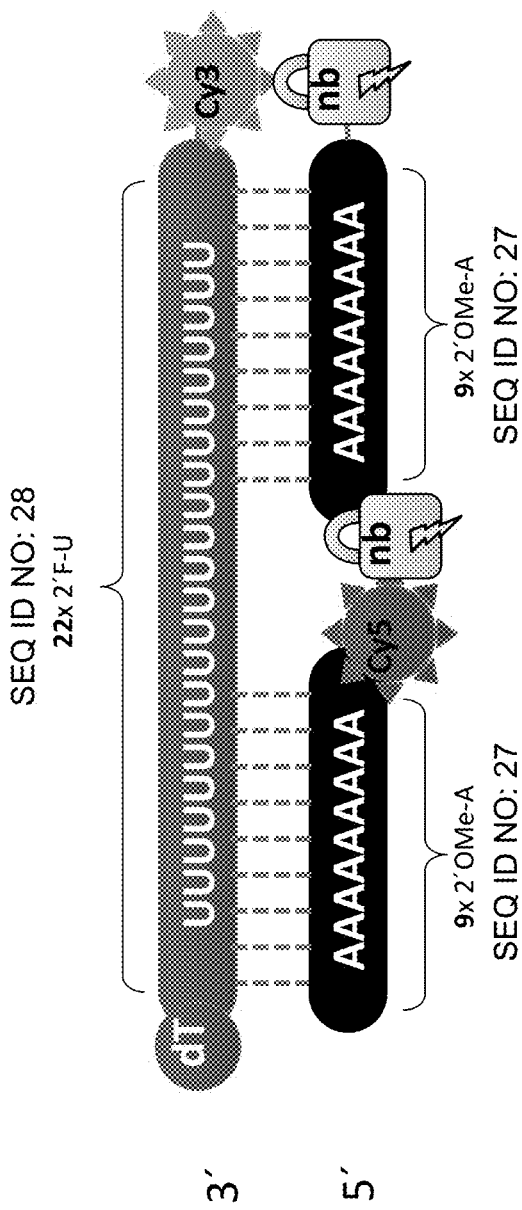
FIG. 25 depicts an exemplary TISA-tag comprising a 22mer poly-2'F-U capture strand, a terminal dT, and lacking a CPD.

FIG. 24 depicts a TISA-tag, which includes a poly-U capture strand (22mer of 2'F-U), with a 3' dT to prime cDNA synthesis. The TISA-tag also comprises a blocking strand comprising two 9mer 2'OMe-A oligonucleotides. The blocking strand also comprises a Cy5 and photocleavable nb moiety between the two 9mer 2'OMe-A oligonucleotides. The poly-A stretches of the blocking strand hybridizes with the poly-U of the capture strand. The capture strand is connected to the block strand via a Cy3, and a photocleavable nb moiety. Because the 3' end of the tag must be kept clear for eventual cDNA generation, the FRET fluorophore (e.g. Cy3) is placed in an interior location. In the exemplary tag depicted in FIG. 24, the TISA comprises a CPP, for example a (Arg)9 peptide, to aid in cellular internalization of the TISA-tag. In contrast, FIG. 25 depicts a similar TISA-tag lacking the CPP. For example, in certain instances, the TISA-tag is able to enter one or more cells of a sample, when the cells are subjected to a permeabilization treatment.

Figure 26:
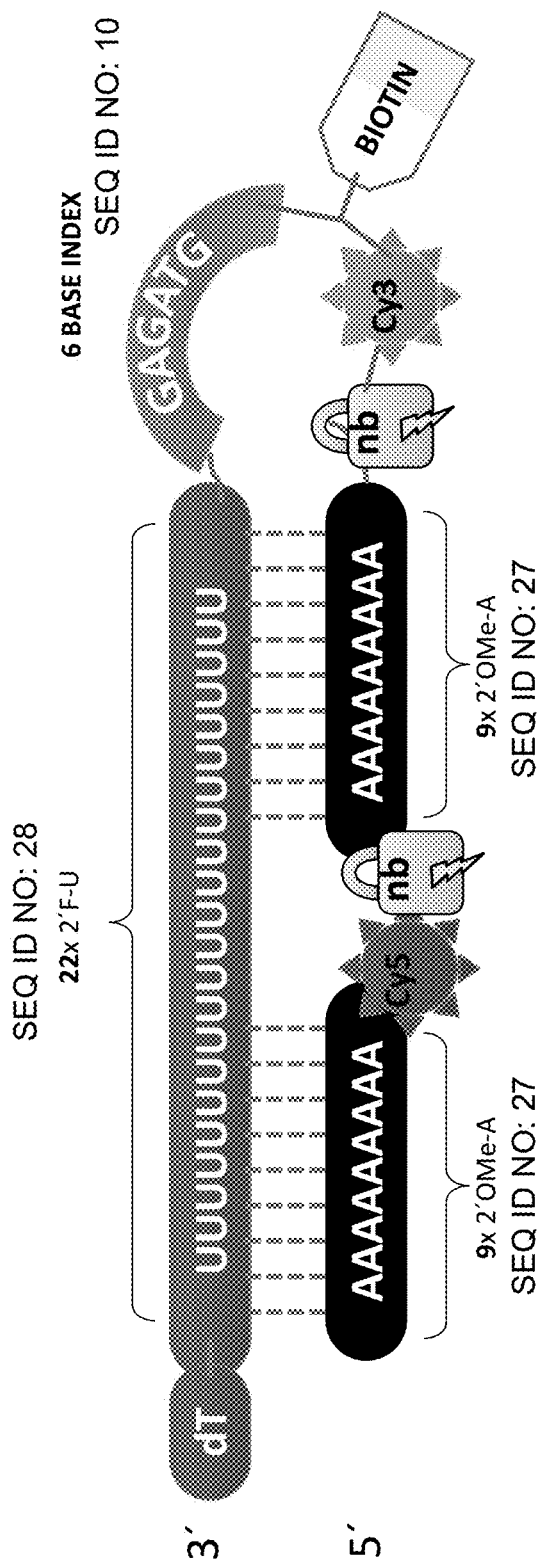
FIG. 26 depicts an exemplary TISA-tag comprising a 22mer poly-2'F-U capture strand, a terminal dT, and a 6 base index oligo.

FIG. 26 depicts a TISA-tag, which includes a poly-U capture strand (22mer of 2'F-U), with a 3'dT to prime cDNA synthesis. The TISA-tag also comprises a blocking strand comprising two 9mer 2'OMe-A oligonucleotides. The blocking strand also comprises a Cy5 and photocleavable nb moiety between the two 9mer 2'OMe-A oligonucleotides. The poly-A stretches of the blocking strand hybridizes with the poly-U of the capture strand. The capture strand is connected to the block strand via a 6 base index, a Cy3, and a photocleavable nb moiety. In certain instances, the TISA-tag may be constructed with a biotin label to allow for isolation of the TISA tag, for example by streptavidin pulldown. The 6 base index (e.g. 5'-GTAGAG-3' (SEQ ID NO: 10)) can be used to identify transcripts isolated using this TISA tag. The index allows for distinguishing the resultant cDNA from endogenous DNA and also allows for multiplexing, when multiple TISA tags are employed, each with a different index.

Figure 27:
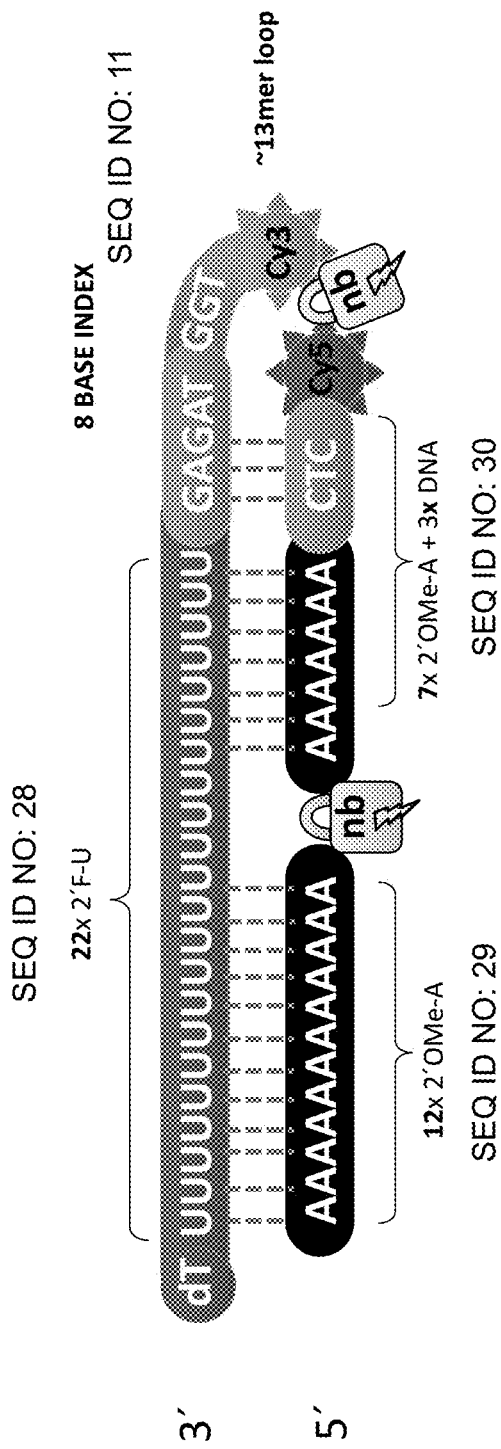
FIG. 27 depicts an exemplary TISA-tag comprising a 22mer poly-2'F-U capture strand, a terminal dT, and an 8 base index oligo. The blocking strand is extended to comprise nucleotides that hybridize to at least part of the 8 base index oligo.

FIG. 27 depicts a TISA-tag, which includes a poly-U capture strand (22mer of 2'F-U), with a 3'dT to prime cDNA synthesis. The TISA-tag also comprises a blocking strand comprising a 12mer 2'OMe-A oligonucleotide and a 7mer 2'OMe-A oligonucleotide. The blocking strand also comprises a photocleavable nb moiety between the 12mer 2'OMe-A oligonucleotide and 7mer 2'OMe-A oligonucleotide. The poly-A stretches of the blocking strand hybridizes with the poly-U of the capture strand. The capture strand is connected to the block strand via a 8 base index, a Cy3, a photocleavable nb moiety, and a Cy5. The Cy3 and Cy5 are positioned closer to generate a larger change in fluorescence upon photolysis of the photocleavable moiety. The 8 base index (e.g. 5'-TGGTAGAG-3' (SEQ ID NO: 11)) can be used to identify transcripts isolated using this TISA tag. The index thus allows for multiplexing, when multiple TISA tags are employed, each with a different index. To improve stability, the blocking strand further comprises three nucleotides which hybridize to the first 3 nucleotides of the 8 base index.

Figure 28:
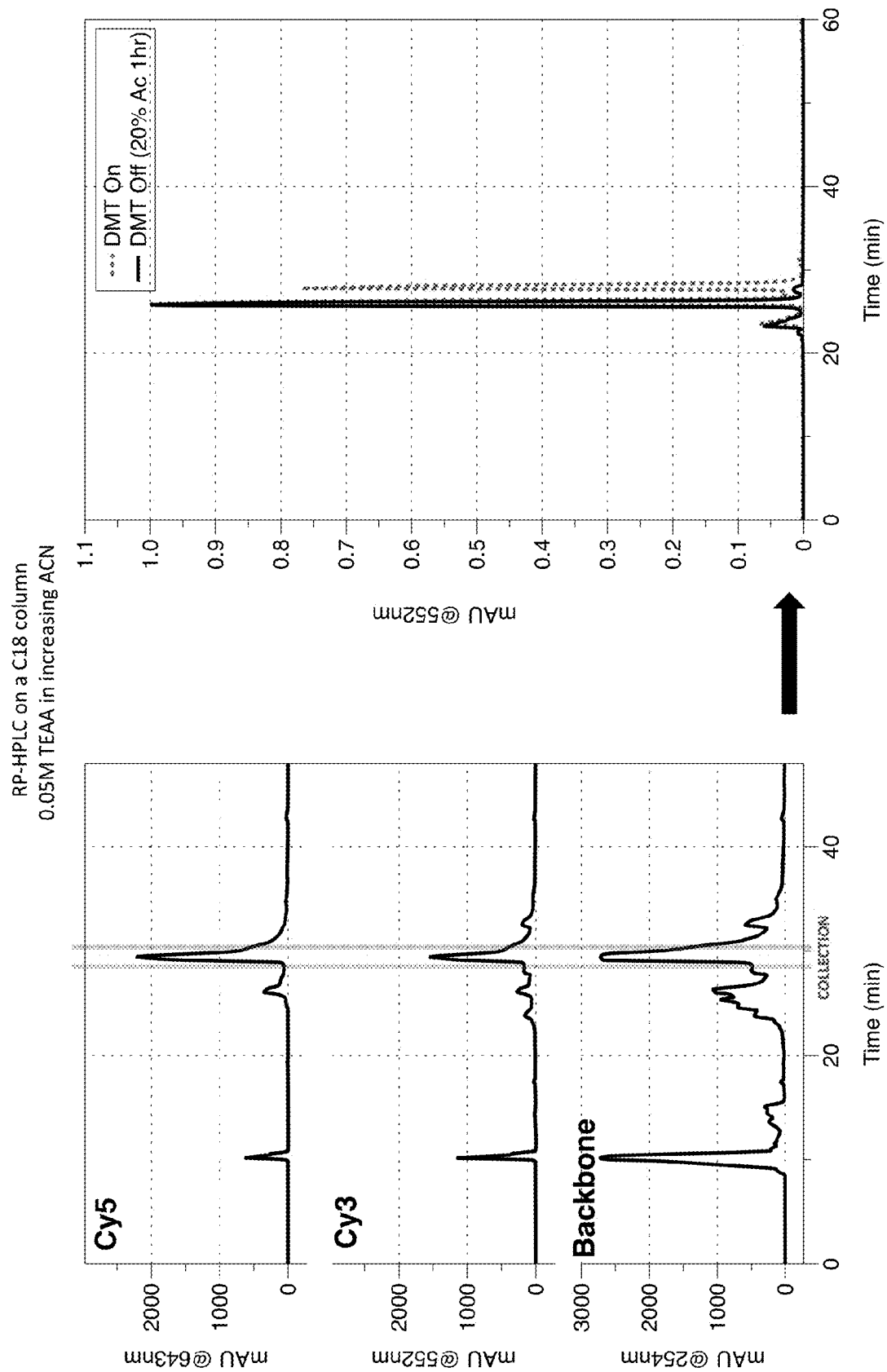
FIG. 28 depicts the results of the purification of a TISA-tag.
Figure 29:
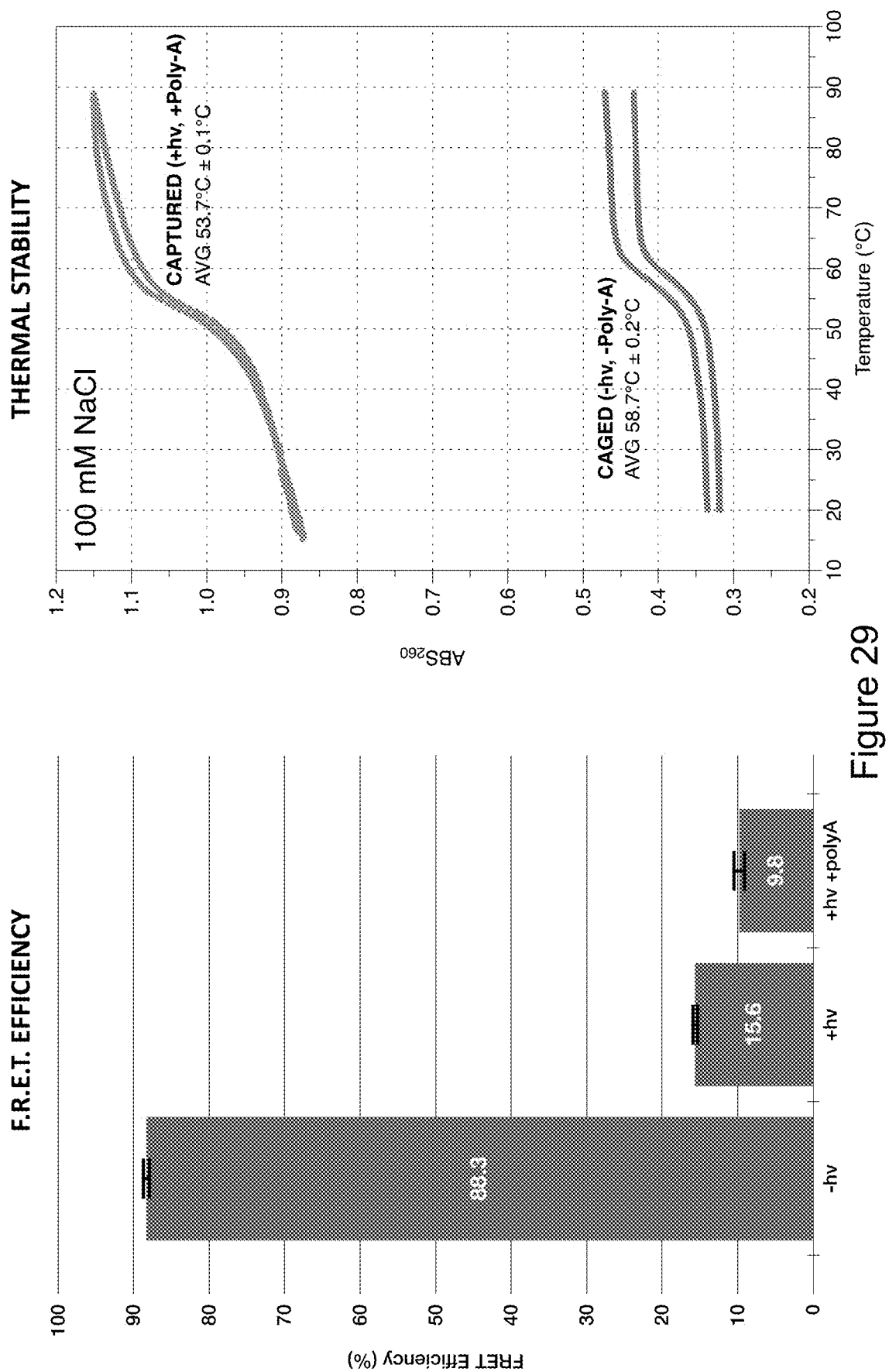
FIG. 29 is a set of graphs depicting the characterization of a TISA-tag. FRET efficiency (left) and thermal stability (right) were investigated for TISA-tag in their caged and captured conformations.

Purification and characterization of this TISA-tag, having the 8 base index and blocking strand comprising 3 nucleotides that hybridize to the index, is shown in FIG. 28 and FIG. 29. FIG. 28 depicts the purification of the TISA-tag. After automated synthesis, deprotection, and cleavage, the TISA tag was purified by RP-HPLC by collecting the fraction at ~30 minutes and then concentrated in a vacufuge. During concentration some of the 5' protecting group, DMT, fell off, resulting in two main peaks (25 min and 28 min) upon reinjection on an analytical column (dotted line). After a 1 hr RT treatment with 20% acetic acid the DMT group was fully removed, leaving a single product peak at 25 min. FRET efficiency of the TISA-tag was investigated in its caged conformation (−hv), uncaged conformation (+hv), and captured conformation (+hv and +polyA), demonstrating that uncaging results in the expected change in FRET signal (FIG. 29). Further, the thermal stability of the caged and captured conformation was investigated as shown in FIG. 29.

Figure 30:
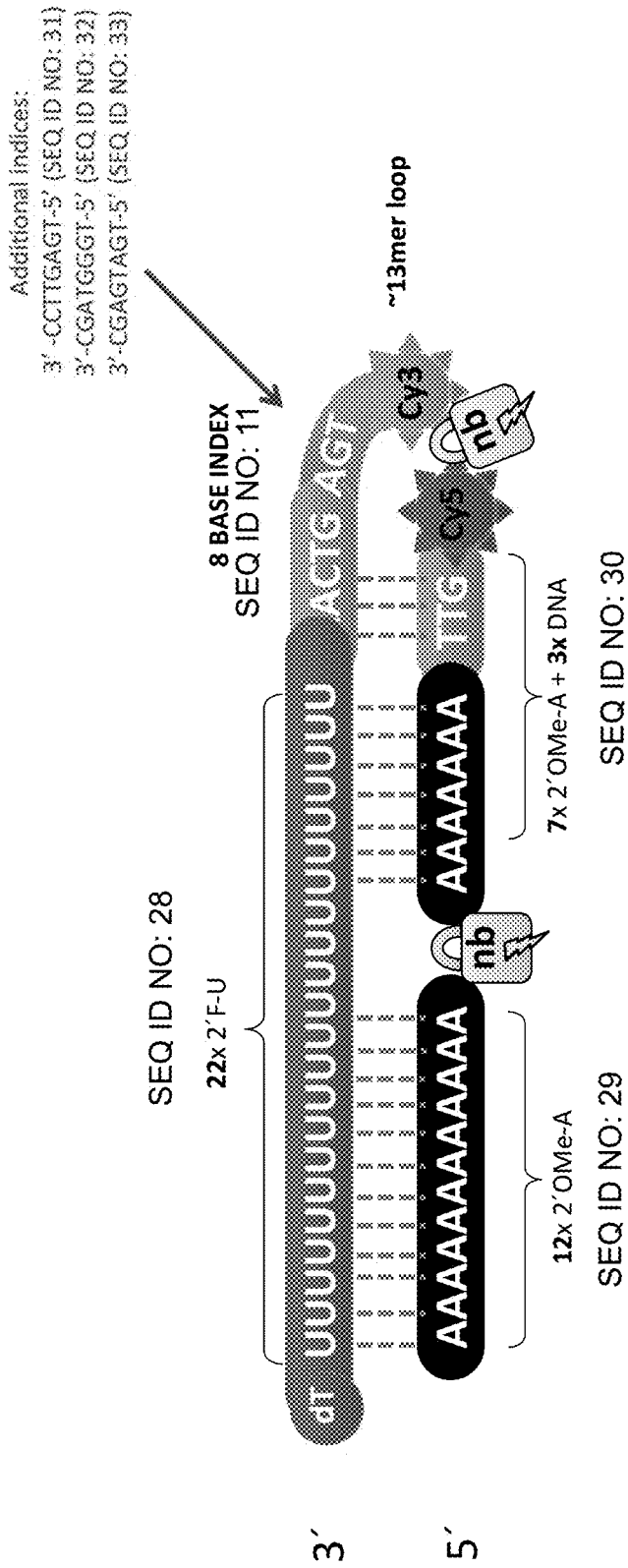
FIG. 30 depicts an exemplary TISA-tag comprising a 22mer poly-2'F-U capture strand, a terminal dT, and alternate 8 base index oligo. The blocking strand is extended to comprise nucleotides that hybridize to at least part of the 8 base index oligo.
Figure 31:
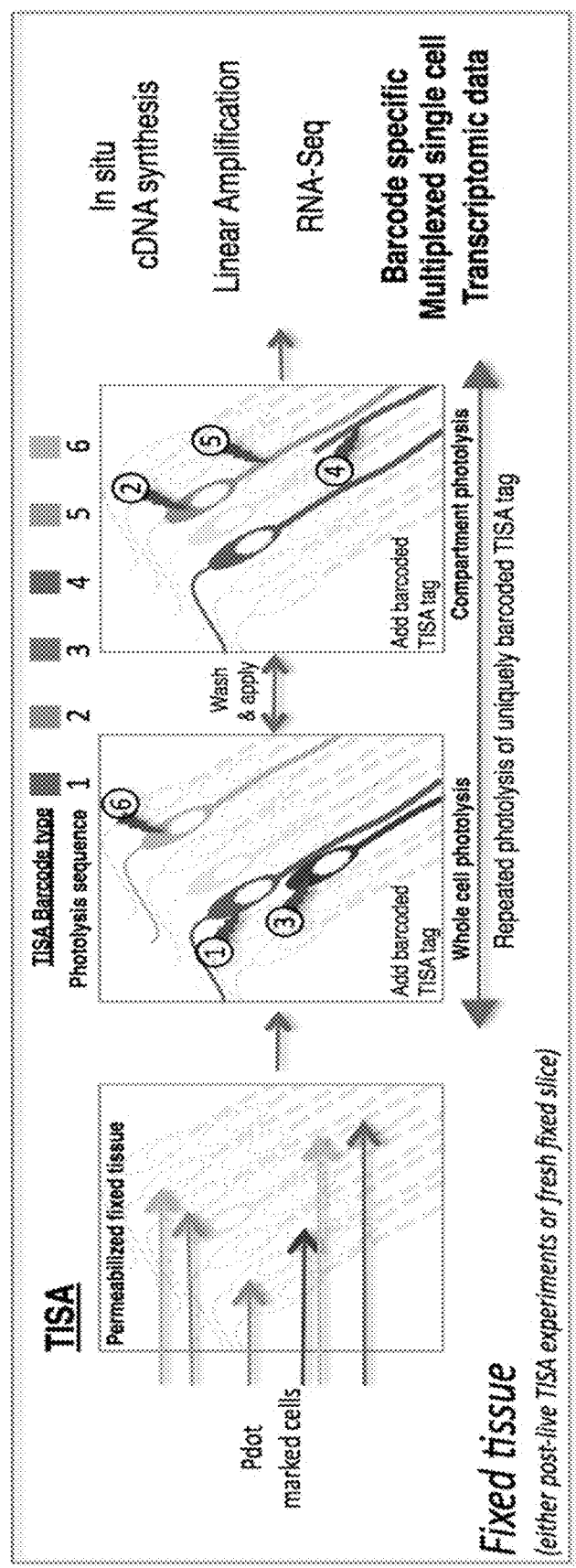
FIG. 31 is a schematic depicting the multiplexing ability of TISA-tags having different indices (barcodes) to analyze nucleic acid molecules in different cells and subcellular compartments.

FIG. 30 depicts a TISA-tag of similar design to that depicted in FIG. 27, except having a different 8 base index and wherein the blocking strand is modified such that it hybridizes with the different index. These exemplary alterations employing unique indices allow for multiplexing such that they can be used to isolate mRNA from multiple spatially resolved ells in the sample or in different subcellular compartments (FIG. 31). In certain cases, the photocleavable nb moieties can be replaced with a Ru-photolinker or other photolinker.

Figure 32:
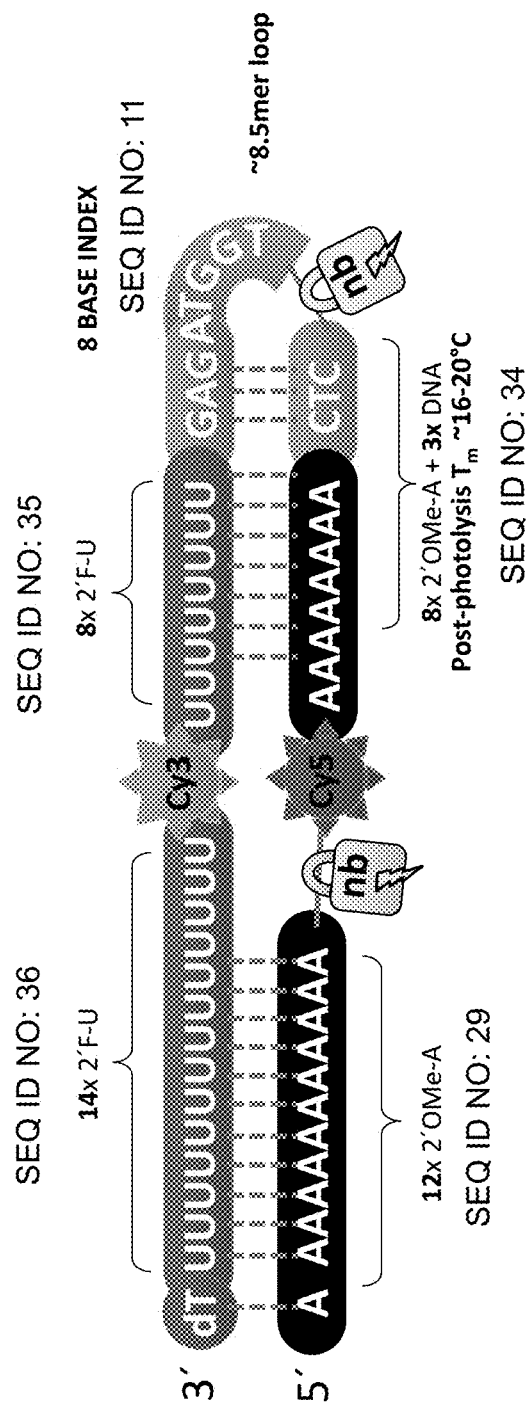
FIG. 32 depicts an exemplary TISA-tag comprising a capture strand divided by a Cy3 fluorophore. The TISA-tag comprises a terminal dT, and an 8 base index oligo. The blocking strand is extended to comprise nucleotides that hybridize to at least part of the 8 base index oligo.

FIG. 32 depicts a TISA-tag, which includes a poly-U capture strand comprising a 14mer 2'F-U and a 8mer 2'F-U separated by a Cy3. The capture strand also comprises a 3'dT to prime cDNA synthesis. It was verified that DNA polymerase I is sufficiently processive to read through a cyanine dye. Thus, in this design, the FRET pair is moved into the hairpin duplex far enough to better report on hybridization state but far enough from the hairpin terminus to maintain stable binding of the 3' dT to target mRNA poly-A tail. The TISA-tag also comprises a blocking strand comprising a 12mer 2'OMe-A oligonucleotide and a 8mer 2'OMe-A oligonucleotide. The blocking strand also comprises a Cy5 and a photocleavable nb moiety between the 12mer 2'OMe-A oligonucleotide and 8mer 2'OMe-A oligonucleotide. The poly-A stretches of the blocking strand hybridizes with the poly-U and dT of the capture strand. The capture strand is connected to the block strand via a 8 base index and a photocleavable nb moiety The 8 base index (e.g. 5'-TGGTAGAG-3' (SEQ ID NO: 11)) can be used to identify transcripts isolated using this TISA tag. The index thus allows for multiplexing, when multiple TISA tags are employed, each with a different index. To improve stability, the blocking strand further comprises three nucleotides which hybridize to the first 3 nucleotides of the 8 base index.

Figure 33:
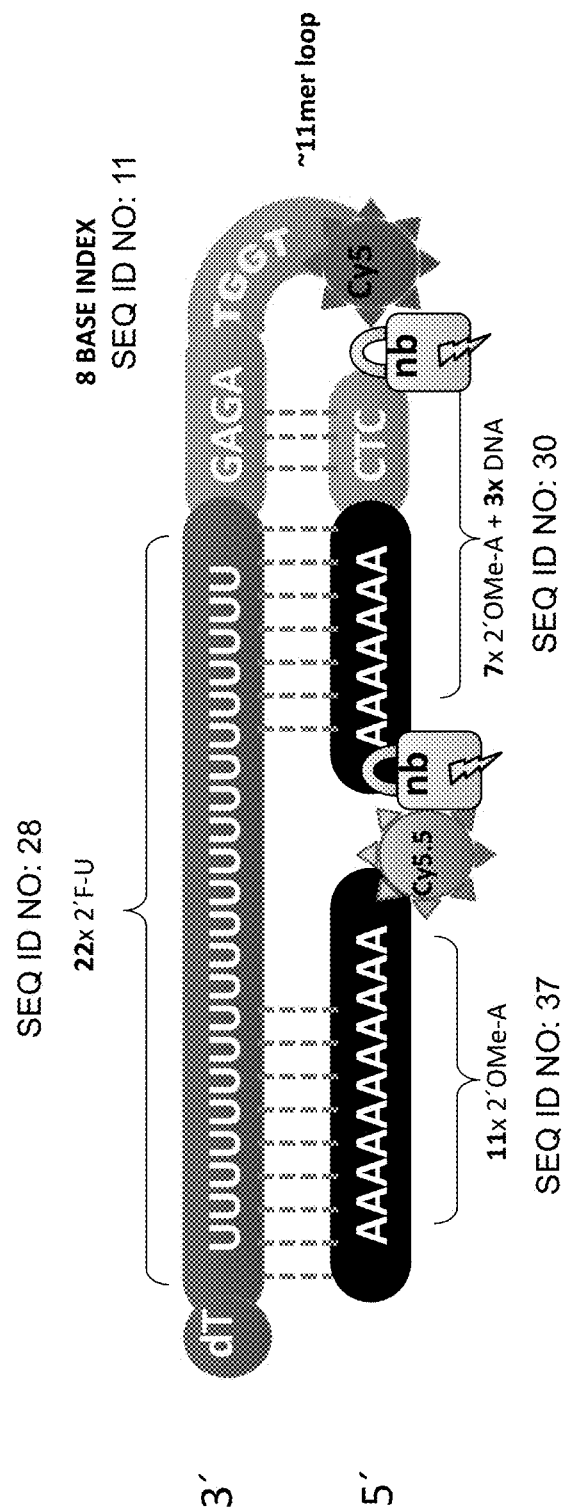
FIG. 33 depicts an exemplary TISA-tag comprising a 22mer poly-2'F-U capture strand, a terminal dT, and an 8 base index oligo. The blocking strand is extended to comprise nucleotides that hybridize to at least part of the 8 base index oligo. The TISA-tag comprises a Cy5/Cy5.5 FRET pair.

FIG. 33 depicts a TISA-tag, which includes a poly-U capture strand (22mer of 2'F-U), with a 3'dT to prime cDNA synthesis. The TISA-tag also comprises a blocking strand comprising a 11mer 2'OMe-A oligonucleotide and a 7mer 2'OMe-A oligonucleotide. The blocking strand also comprises a Cy5.5. and a photocleavable nb moiety between the 11mer 2'OMe-A oligonucleotide and 7mer 2'OMe-A oligonucleotide. The poly-A stretches of the blocking strand hybridizes with the poly-U of the capture strand. The capture strand is connected to the block strand via a 8 base index, a Cy5, a photocleavable nb moiety, and a Cy5. The 8 base index (e.g. 5'-TGGTAGAG-3' (SEQ ID NO: 11)) can be used to identify transcripts isolated using this TISA tag. The index thus allows for multiplexing, when multiple TISA tags are employed, each with a different index. To improve stability, the blocking strand further comprises three nucleotides which hybridize to the first 3 nucleotides of the 8 base index.

Figure 34:
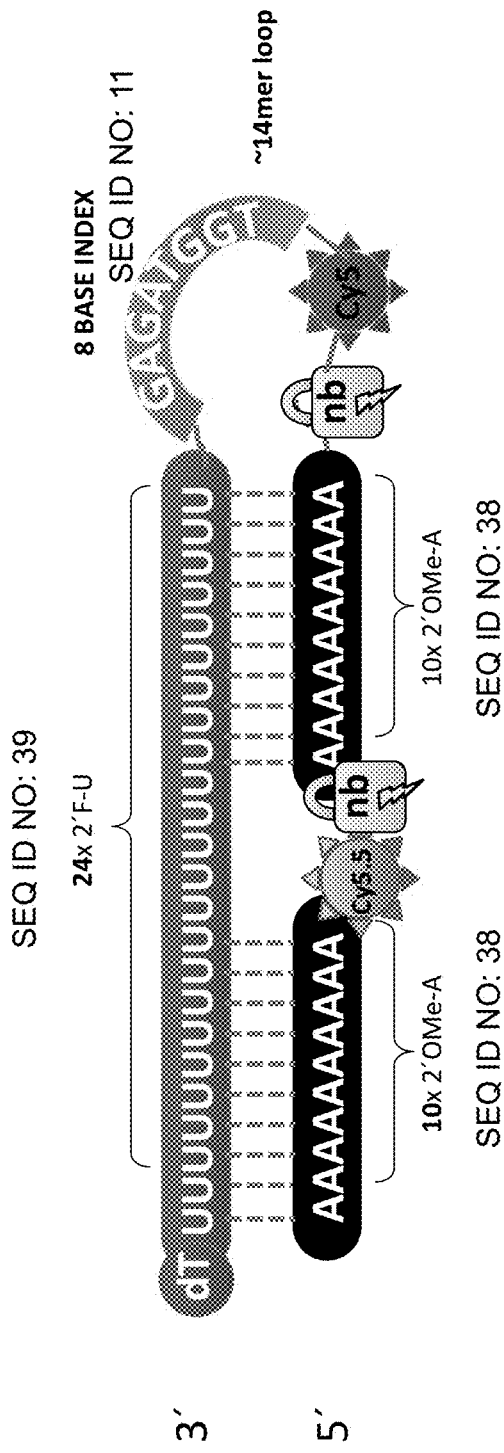
FIG. 34 depicts an exemplary TISA-tag comprising a 24mer poly-2'F-U capture strand, a terminal dT, and a 6 base index oligo. The TISA-tag comprises a Cy5/Cy5.5 FRET pair.

FIG. 34 depicts a TISA-tag, which includes a poly-U capture strand (24mer of 2'F-U), with a 3'dT to prime cDNA synthesis. The TISA-tag also comprises a blocking strand comprising two 10mer 2'OMe-A oligonucleotides. The blocking strand also comprises a Cy5.5 and photocleavable nb moiety between the two 10mer 2'Ome-A oligonucleotides. The poly-A stretches of the blocking strand hybridizes with the poly-U of the capture strand. The capture strand is connected to the block strand via a 8 base index, a Cy5, and a photocleavable nb moiety. The 8 base index (e.g. 5'-TGGTAGAG-3' (SEQ ID NO: 11)) can be used to identify transcripts isolated using this TISA tag. The index thus allows for multiplexing, when multiple TISA tags are employed, each with a different index.

Figure 35:
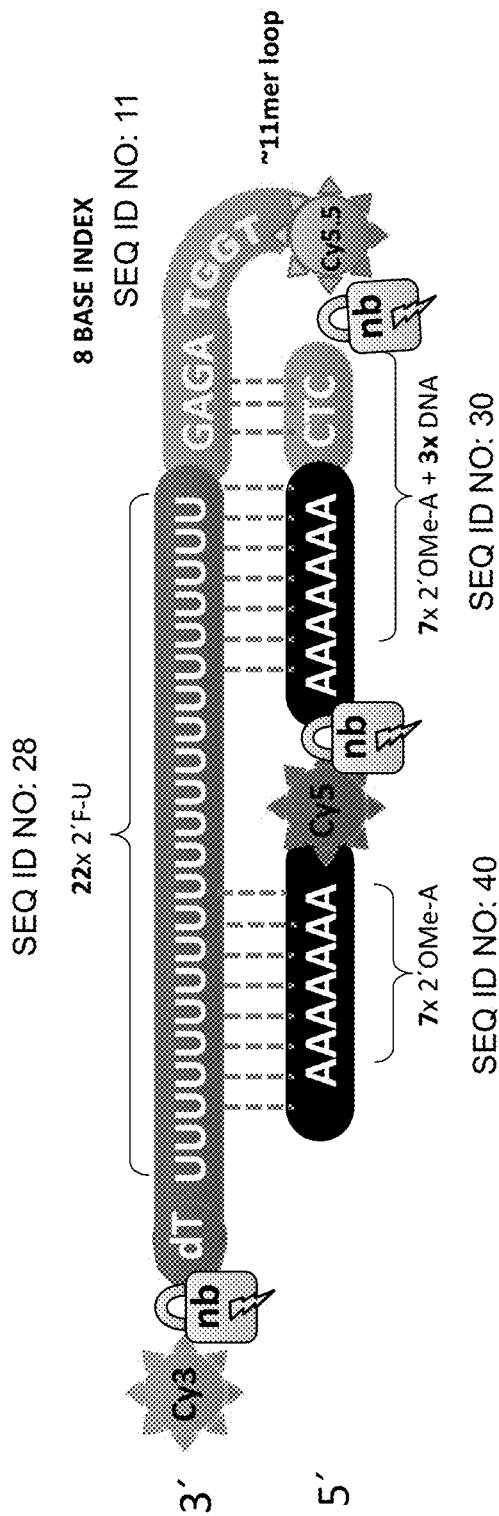
FIG. 35 depicts an exemplary TISA-tag comprising a 22mer poly-2'F-U capture strand, a terminal dT, and an 8 base index oligo. The TISA-tag comprises a Cy5, Cy5.5, and Cy3 fluorophores. The blocking strand is extended to comprise nucleotides that hybridize to at least part of the 8 base index oligo.

FIG. 35 depicts a TISA-tag, which includes a poly-U capture strand (22mer of 2'F-U), with a 3'dT to prime cDNA synthesis. The tag also comprises a Cy3 and a photocleavable nb moiety on the 3' end of the capture strand. The TISA-tag also comprises a blocking strand comprising two 7mer 2'Ome-A oligonucleotides. The blocking strand also comprises a Cy5 and photocleavable nb moiety between the two 7mer 2'Ome-A oligonucleotides. The poly-A stretches of the blocking strand hybridizes with the poly-U of the capture strand. The capture strand is connected to the block strand via a 8 base index, a Cy5.5, and a photocleavable nb moiety. The 8 base index (e.g. 5'-TGGTAGAG-3' (SEQ ID NO: 11)) can be used to identify transcripts isolated using this TISA tag. The index thus allows for multiplexing, when multiple TISA tags are employed, each with a different index. To improve stability, the blocking strand further comprises three nucleotides which hybridize to the first 3 nucleotides of the 8 base index.

Figure 36B:
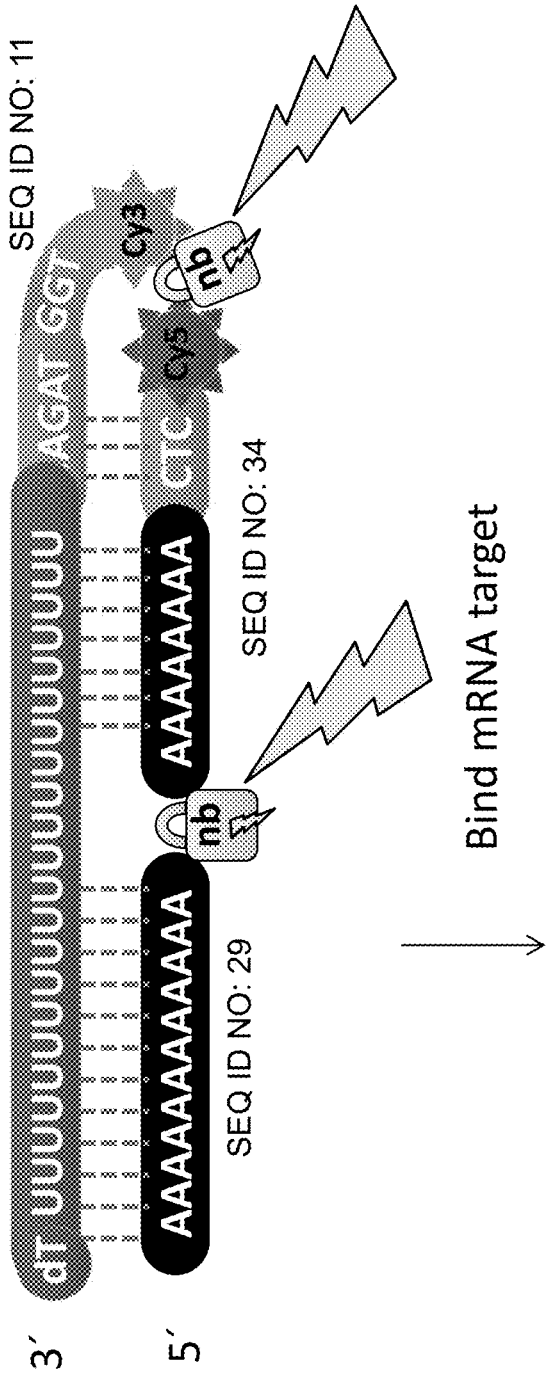
Figure 36B:
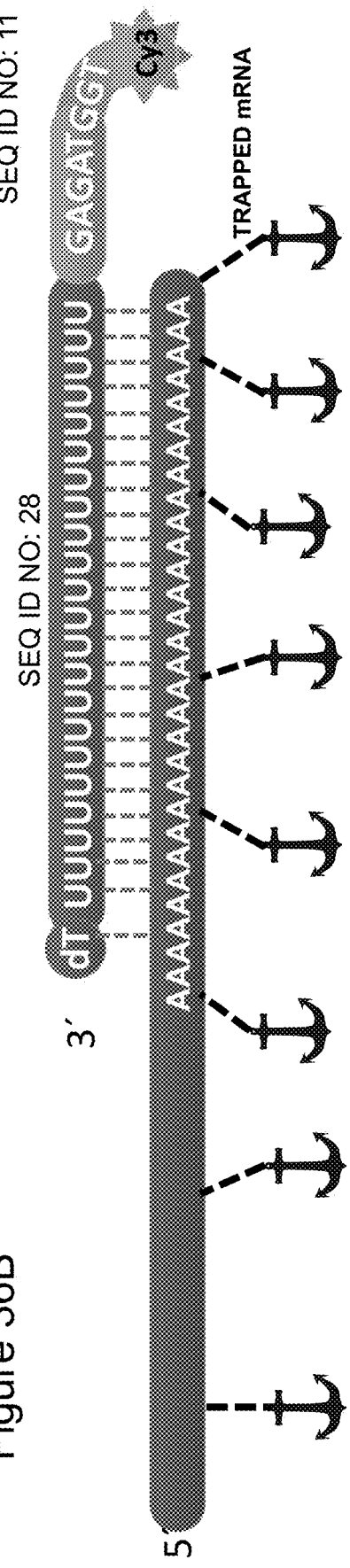

FIG. 36 depicts an exemplary protocol using the TISA-tags described above. Following application of the TISA-tag to the sample of interest, the photocleavable nb moieties are cleaved upon laser irradiation (FIG. 36A), thereby uncaging the TISA-tag. Uncaging results in the two oligonucleotides of the blocking strand to dissociate from the capture strand, thereby allowing the poly-U of the capture strand to bind to a polyA tail of mRNA in the sample (FIG. 36B) The TISA-tag may be selectively uncaged in one or more targeted cells of interest, thereby selectively capturing mRNA from cells of interest, while not capturing mRNA from other, non-irradiated, cells. Thus, specific cells from a fixed tissue sample may be analyzed.

The captured mRNA is then amplified using antisense RNA (aRNA) amplification as follows. Reverse transcriptase and dNTPs are added to the sample (FIG. 36C), and the reverse transcriptase is able to use the 3'dT to prime cDNA synthesis from the captured mRNA (FIG. 36D). The cDNA of the cDNA-mRNA hybrid molecule is released via denaturing or RNA hydrolysis (e.g. NaOH). Random primers, DNA polymerase I, and T4 DNA polymerase are then added (FIG. 36E). The random primers are used to prime second cDNA strand synthesis from the first strand cDNA using the polymerases (FIG. 36F). The resultant double-stranded cDNA molecule comprises a 8 base index on each strand. The double-stranded cDNA molecule is denatured and an index-T7 oligo, DNA polymerase I and T4 DNA polymerase are applied (FIG. 36G). The index-T7 oligo comprises a polyT region, which binds to the polyA of the second strand DNA; an index-binding region, which binds to the index of the second strand DNA; and a T7 promoter region. The index-binding region of the oligo ensures that endogenously primed RNA from non-TISA-targeted cells are not amplified, which would otherwise contaminate data from the TISA-targeted cell(s).

In certain instances, the oligo further comprises a spacer region between the promoter and the index-binding region, to ensure efficient transcription of the index. In certain instances, the oligo further comprises a plurality of bases 5' to the promoter region, which ensures efficient binding of the T7 RNA polymerase to the promoter region.

The index-T7 oligo thus binds to the second strand cDNA and a double-stranded cDNA molecule is synthesized using the polymerases (FIG. 36H). The resultant double-stranded cDNA is then amplified using in vitro transcription, where T7 RNA polymerase is able to bind to the T7 promoter region and transcribe an RNA molecule comprising the antisense RNA of the captured RNA and the index, thus allowing for in situ transcription from the cDNA strand. The RNA may be further amplified using the index-T7 oligo in subsequent rounds of aRNA amplification as necessary to generate sufficient material for various detection methods (e.g., PCR, RNA sequencing, etc.)

Example 8: TISA in Fixed Pancreatic Tissue

Described herein is an experiment using TISA-tags to capture and amplify mRNA in a specific subset of pancreatic cells (alpha cells) from a fixed sample of pancreatic tissue. It is demonstrated that TISA is able to selectively capture alpha cell-specific transcripts while not capturing beta cell-specific transcripts.

Figure 37:
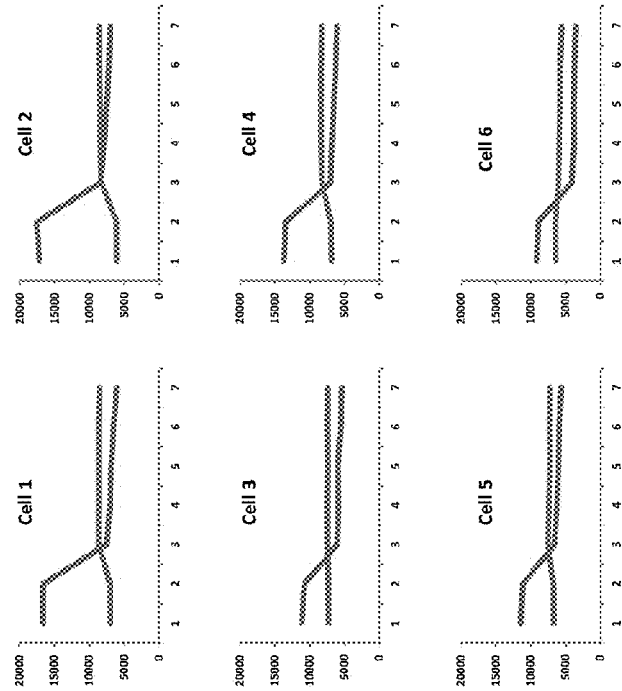
FIG. 37 depicts the results of example experiments depicting the specific uncaging of TISA-tag in fixed and stained pancreatic tissue. The tissue was stained for insulin and glucagon and specifically uncaged in glucagon positive alpha cells, which resulted in the capture of alpha cell specific or enriched markers.
Figure 37:
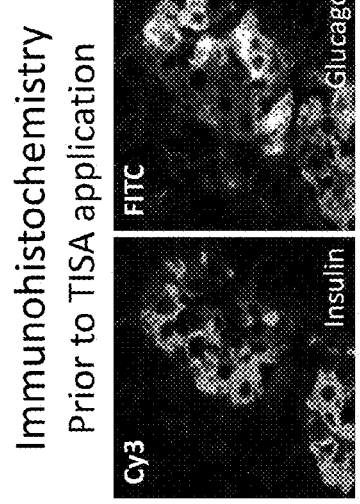
Figure 37:
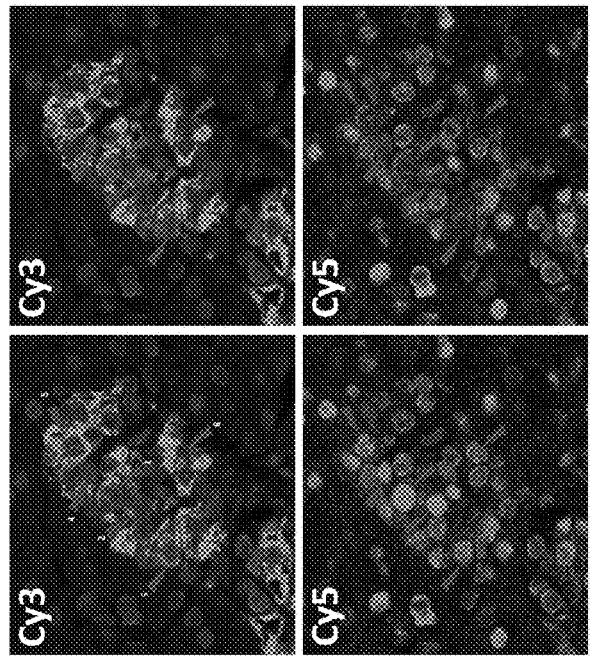

A human pancreatic biopsy sample was obtained. The sample was sectioned and fixed with paraformaldehyde. The fixed section was immunostained for glucagon, an alpha cell-specific marker; and insulin, a beta cell-specific marker (FIG. 37).

The TISA-tag depicted in FIG. 27 was perfused on the fixed section. Using a confocal microscope, the TISA-tag was specifically uncaged in the cell bodies of multiple glucagon positive cells by photolysis of the photocleavable moieties. FIG. 37 depicts the change in FRET signal in the irradiated cells. Following washing, first strand cDNA synthesis was performed by applying a solution comprising SuperscriptIII (RNA transcriptase), dNTPs, RNasin, DDT, and first strand buffer to the sample. The sample was incubated for 30 minutes at 42° C. in a humidified chamber. cDNA is released using alkaline hydrolysis of RNA. The cDNA is then collected from the fixed section and moved into a reaction tube.

The cDNA was purified with ethanol purification and was random primed for second stranded synthesis using DNA polymerase I and T4 DNA polymerase. The double-stranded cDNA was denatured and the index-T7 oligo was hybridized and second strand synthesis was repeated. The material was subsequently amplified using aRNA amplification using the index-T7 oligo at each round of amplification.

Libraries were made from the amplified transcripts using the Illumina TruSeq stranded mRNA kit. The libraries were sequenced on Illumina HiSeq 2500. The reads were mapped on the STAR aligner and quantified and normalized using HTSeq and DESeq.

When not accounting for the presence of the index, 28,037 unique transcripts were identified. When stratified based on the presence of the index, 14,122 unique transcripts were identified. Thus, verification using the index of the TISA-tag demonstrated that the TISA protocol was able to capture 14,122 unique transcripts. It was observed that these transcripts were enriched in alpha cell-specific markers but not beta cell-specific markers (Table 3) demonstrating that the TISA protocol can specifically identify transcripts from targeted cells.

TABLE 3

| Gene | Total Reads | |
|------|-------------|---|
| GCG | 2 | alpha cell marker |
| PCSK2 | 138 | prohormone convertase- processes pro-glucagon into glucagon in alpha cells |
| GRIN3A | 83 | alpha cell enriched |
| POPDC3 | 16 | alpha cell enriched |
| STK32B | 150 | alpha cell enriched |
| TTR | 13 | alpha cell enriched |
| ARX | 6 | alpha cell marker |
| INS | 0 | beta cell marker |
| ADRBK1 | 0 | beta cell marker |
| ECHS1 | 0 | beta cell marker |
| PPP1R1A | 0 | beta cell marker |
| PSMC5 | 0 | beta cell marker |
| SFTPA1 | 0 | beta cell enriched |

Example 9: TISA Bandaid

A TISA-bandaid molecule was designed and generated as depicted in FIG. 38. The molecule is partially double-stranded comprising two hybridized oligonucleotides. The capture oligo comprises a Cy3, an index, a T7 promoter region and a capture region. The capture region comprises a polyT stretch and two guanine residues within the polyT stretch. In one embodiment, the capture oligo comprises a 5' Cy3 (FIG. 38A). In one embodiment, the capture oligo comprises an internal Cy3 (FIG. 38B).

The blocking oligo comprises a Cy5 and a blocking region comprising a polyA stretch. The blocking region comprises two cytosine residues within the polyA stretch. The blocking oligo also comprises two photocleavable nb moieties.

The cytosines of the blocking region and the guanines of the capture region are incorporated to ensure proper alignment and therefore complete blocking of the polyT stretch.

An experiment was performed using the capture oligo to detect and amplify mRNA from a reference RNA sample. The capture strand was incubated with 1ng of human brain reference RNA (Agilent 740000). The captured material (poly A+) was amplified using standard aRNA amplification with the modification that the index-T7 oligo was used for each round of amplification. When not accounting for the presence of the index, 28,628 unique transcripts were identified. When stratified based on the presence of the index, 16,547 unique transcripts were identified.

Example 10: Photo-Activated Chain Terminator TISA

A photo-activated chain terminator TISA molecule was designed and generated as depicted in FIG. 39. The molecule comprises a single-strand oligonucleotide comprising a T7 promoter site to prime for aRNA amplification, an index, and a capture region. The index is used to identify TISA mediated amplification, to eliminate the confounder that is endogenous priming, and to allow for multiplexing. In the exemplary molecule depicted in FIG. 39A-FIG. 39C, the capture region comprises a polyT stretch. The oligonucleotide comprises a 3' photo-activatable dideoxynucleotide. The photo-activatable dideoxynucleotide blocks strand synthesis until photoactivated. In the instance where the capture region comprises a polyT stretch, the photo-activatable dideoxynucleotide is one of ddATP, ddCTP, or ddGTP, such that the polyT stretch is more likely to hybridize to the terminal polyA tail. In certain instances the molecule comprises one or more fluorophores, such as a FRET pair. As depicted in FIG. 39, the molecule may comprise, for example a Cy3 at the 5' end (FIG. 39A), a Cy5.5. within the polyT stretch (FIG. 39B), or a Cy5.5 at the 5'end of the polyT stretch (FIG. 39C). These fluorophores can form a FRET pair with a Cy5 fluorophore positioned on the photoactivatable dideoxynucleotide.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A caged nucleic acid molecule comprising: a first, second, and third oligonucleotide, wherein the first oligonucleotide is linked to the second oligonucleotide through a first photocleavable linker and the second oligonucleotide is linked to the third oligonucleotide through a second photocleavable linker, wherein the first oligonucleotide comprises one or more terminal deoxynucleotides, wherein the first oligonucleotide comprises 2'-fluoro uridine, and wherein the one or more terminal deoxynucleotides comprises one or more thymidines.

2. The molecule of claim 1, wherein the second oligonucleotide and third oligonucleotide each comprise a nucleotide sequence that is complementary to the first oligonucleotide, thereby forming a hairpin where the first oligonucleotide hybridizes to both the second oligonucleotide and third oligonucleotide.

3. The molecule of claim 2, wherein the first photocleavable linker and the second photocleavable linker comprise nitrobenzyl.

4. The molecule of claim 1, wherein the first oligonucleotide comprises an antisense oligonucleotide comprising a nucleic acid sequence that is complementary to the polyA tail of an mRNA.

5. The molecule of claim 4, wherein irradiation of the photocleavable linkers exposes the antisense oligonucleotide thereby allowing the antisense oligonucleotide to hybridize with a target nucleic acid, wherein the antisense oligonucleotide is complementary to the target nucleic acid.

6. The molecule of claim 5, wherein the first oligonucleotide and one or more terminal deoxynucleotides serve as a primer to synthesize cDNA from the target nucleic acid.

7. The molecule of claim 1, wherein the molecule further comprises an index oligonucleotide.

8. The molecule of claim 1, further comprising one or more fluorophores.

9. The molecule of claim 8, wherein the one or more fluorophores is a FRET pair.

* * * * *